United States Patent
Nielson et al.

(10) Patent No.: US 9,951,377 B2
(45) Date of Patent: Apr. 24, 2018

(54) METHODS, KITS AND COMPOSITIONS PERTAINING TO THE SUPPRESSION OF THE DETECTABLE PROBE BINDING TO RANDOMLY DISTRIBUTED REPEAT SEQUENCES IN GENOMIC NUCLEIC ACID

(71) Applicant: 1.) Applied Biosystems, LLC 2.) Dako Denmark A/S, Carlsbad, CA (US)

(72) Inventors: Kirsten Vang Nielson, Bronshoj (DK); Jens Hyldig-Nielsen, Moss Beach, CA (US); Brett F. Williams, Eugene, OR (US)

(73) Assignees: APPLIED BIOSYSTEMS, LLC, Carlsbad, CA (US); DAKO DENMARK A/S, Glostrup (DK)

( * ) Notice: Subject to any disclaimer, the term of this patent is extended or adjusted under 35 U.S.C. 154(b) by 224 days.

(21) Appl. No.: 14/304,796

(22) Filed: Jun. 13, 2014

(65) Prior Publication Data

US 2014/0378326 A1    Dec. 25, 2014

Related U.S. Application Data

(60) Division of application No. 13/368,732, filed on Feb. 8, 2012, now Pat. No. 8,754,191, which is a continuation of application No. 12/619,664, filed on Nov. 16, 2009, now abandoned, which is a continuation of application No. 10/255,434, filed on Sep. 24, 2002, now abandoned.

(60) Provisional application No. 60/324,499, filed on Sep. 24, 2001.

(51) Int. Cl.
*C12Q 1/68*    (2006.01)

(52) U.S. Cl.
CPC ......... *C12Q 1/6832* (2013.01); *C12Q 1/6837* (2013.01); *C12Q 1/6876* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,225,326 A * | 7/1993 | Bresser | C12Q 1/6886 424/1.49 |
| 5,447,841 A | 9/1995 | Gray et al. | |
| 5,830,670 A | 11/1998 | de la Monte et al. | |
| 6,171,860 B1 | 1/2001 | Baker et al. | |
| 6,184,212 B1 | 2/2001 | Miraglia et al. | |
| 6,232,462 B1 | 5/2001 | Collins et al. | |
| 6,492,181 B1 | 12/2002 | Monia et al. | |

FOREIGN PATENT DOCUMENTS

| | | | |
|---|---|---|---|
| WO | WO 98/24933 | * | 6/1998 |
| WO | WO-1998/024933 | | 6/1998 |
| WO | WO-2001/038586 | | 5/2001 |

OTHER PUBLICATIONS

Batzer et al. (GATA 11(2):34-38, 1994).*
Jurka et al. (J Mol Evol. (1991) 32:105-121).*
Baldini, Antonio et al., "In Situ Hybridization Banding of Human Chromosomes with Alu-PCR Products: A Simultaneous Karyotype for Gene Mapping Studies", *Genomics*, vol. 9, 1991, 770-774.
Batzer, Mark A. et al., "A Consensus Alu Repeat Probe for Physical Mapping", *GATA* vol. 11, Issue 2, 1994, 34-48.
Boffa, L. C. et al., "Isolation of Active Genes Containing CAG repeats by DNA Strand Invasion by a Peptide Nucleic Acid", *Proc. Natl. Acad. Sci. USA*, vol. 92, 1995, 1901-1905.
Fiandaca, et al., "PNA blocker probes enhance specificity in probe assays", Nielsen and Egholm, Bedford, MA01730, XP001160705, 1999.
Suzuki, et al., "*Homo sapiens* cDNA clone", *Database EBI* [Online] Apr. 5, 2000 (Apr. 5, 2000), XP002248346 Database accession No. AU105620, Apr. 5, 2000.
Taneja, et al., *Genes, Chromosome, & Cancer*, vol. 30, 2001, 57-63.
Thisted, M. et al., "Application of Peptide Nucleic Acid Probes for In Situ Hybridization", *Peptide Nucleic Acids: Protocols and Applications*, ed. by Nielsen and Egholm, 1999, 99-118.

* cited by examiner

*Primary Examiner* — Juliet C Switzer

(57) ABSTRACT

This invention is directed to methods, kits, non-nucleotide probes as well as other compositions pertaining to the suppression of binding of detectable nucleic acid probes to undesired nucleotide sequences of genomic nucleic acid in assays designed to determine target genomic nucleic acid.

7 Claims, 21 Drawing Sheets

Illustration of the localization of non-nucleotide probes on ds-target for blocking.

| | A | G | A | T | C | G | C | C | A | C | T | G | C | A | C | T | C | C | A | G | C | C | T | G | G | G | C | G | | |
|---|---|---|---|---|---|---|---|---|---|---|---|---|---|---|---|---|---|---|---|---|---|---|---|---|---|---|---|---|---|---|
| | | | | | | | | | 250 | | | | | | | | | | 260 | | | | | | | | 270 | | Majority | |
| 233 | A | G | A | T | C | G | C | C | C | A | C | T | G | C | A | C | T | C | C | A | G | C | C | T | G | G | G | C | G | HSU14574.seq Sx |
| 233 | A | G | A | T | C | C | G | C | C | A | C | T | T | G | C | A | C | T | C | C | A | G | C | C | T | G | G | G | C | A | HSU14573.seq Sq |
| 233 | A | G | A | T | C | G | C | C | C | A | T | T | G | C | A | C | T | C | C | A | G | C | C | T | G | G | G | C | A | HSU14572.seq Sp |
| 231 | A | G | A | T | C | G | C | C | C | A | C | T | G | C | A | C | T | C | C | A | G | C | C | T | G | - | G | C | G | HSU14571.seq Sc |
| 233 | T | G | A | T | C | G | C | C | C | A | T | T | G | C | A | C | T | C | C | A | G | C | C | T | G | G | G | C | G | HSU14567.seq J |

| | A | C | A | - | G | G | C | G | A | G | A | C | T | C | C | G | T | C | T | C | A | A | A | A | A | A | | |
|---|---|---|---|---|---|---|---|---|---|---|---|---|---|---|---|---|---|---|---|---|---|---|---|---|---|---|---|---|
| | | | | 280 | | | | | | | | | | | | | 290 | | | | | | | | | | Majority | |
| 263 | A | C | A | - | G | A | G | G | A | G | A | C | T | C | C | G | T | C | T | C | A | A | A | A | A | A | HSU14574.seq Sx |
| 263 | A | C | A | - | G | A | G | G | A | A | A | C | T | C | C | G | T | C | T | C | A | A | A | A | A | A | HSU14573.seq Sq |
| 263 | A | C | A | - | G | A | G | G | A | G | A | C | T | C | C | G | T | C | T | C | A | A | A | A | A | A | HSU14572.seq Sp |
| 260 | A | C | A | - | G | A | G | G | A | G | A | C | T | C | C | G | T | C | T | C | A | A | A | A | A | A | HSU14571.seq Sc |
| 263 | A | C | A | - | G | A | G | G | A | G | A | C | T | C | C | G | T | C | T | C | A | A | A | A | A | A | HSU14567.seq J |

Examples of PNA oligo constructs that obtained a high score in the R-banding approach
Figure 3A-1
Seq. Id. No. 4 (PNA No. 15)
Figure 3A-2
Seq. Id. No. 10 (PNA No. 61)
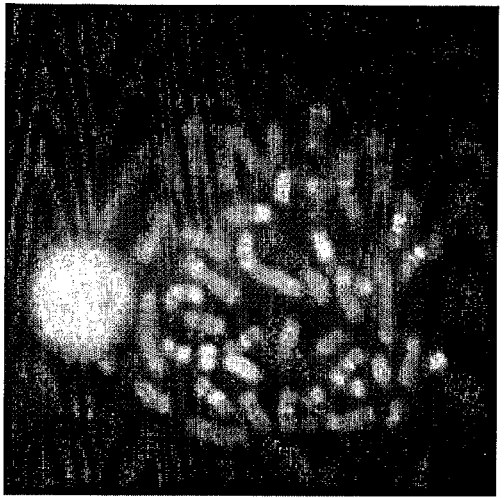
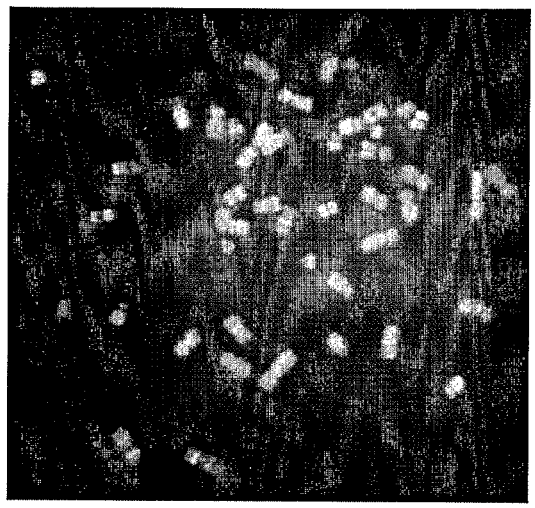
Examples of constructs that only just passed the defined limit value
Figure 3B-1
Seq. Id. No. 7 (PNA No. 46)
Figure 3B-2
Seq. Id. No. 12 (PNA No. 75)
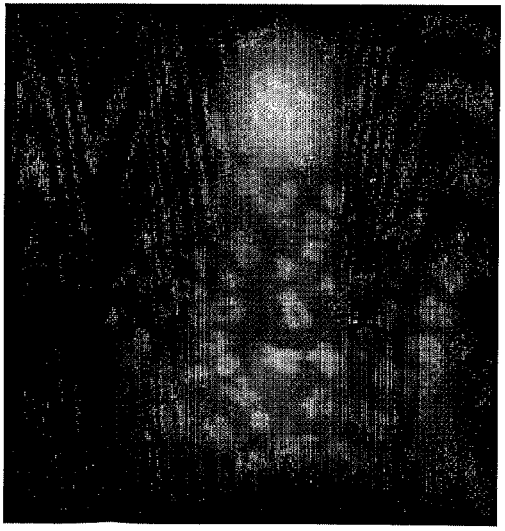

Figure 4-A
Seq. Id. No. 6 (J and S family consensus)

Figure 4-B
Seq. Id. No. 37 (Y family consensus)

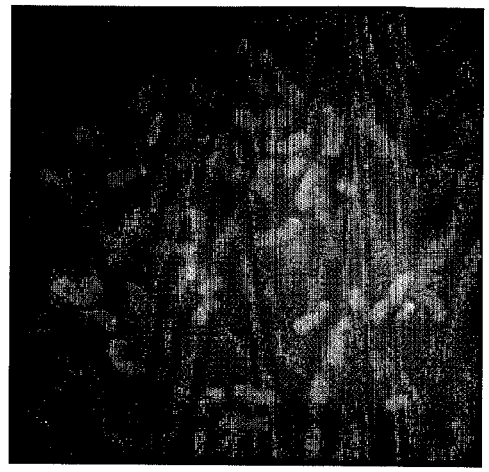

Figure 4-C
Seq. Id. No. 11 (J and S family consensus)

Figure 4-D
Seq. Id. No. 40 (Y family consensus)

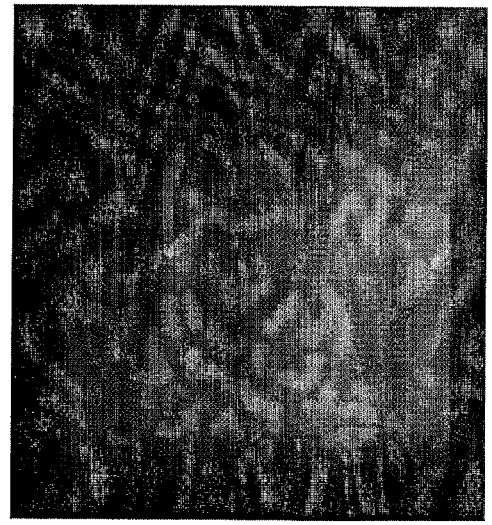

Illustration of the reduction in Alu-banding that appear when PNA oligo constructs designed from the consensus sequence of the Y family branch rather than the consensus of the J and S family branches are used for hybridization to metaphase spreads.

HER2 probe + PNA oligo mixture

HER2 probe + Cot1 DNA

HER2 probe without a blocking agent

MLL probes + PNA oligo mixture

MLL probes + Cot1 DNA

MLL probes without a blocking agent

Rhodamine labeled HER2 probe hybridized to paraffin embedded sections of a mamma carcinoma. 100 x.

HER2 probe + PNA oligo mixture

HER2 probe+ Cot1 DNA

HER2 probe without a blocking agent

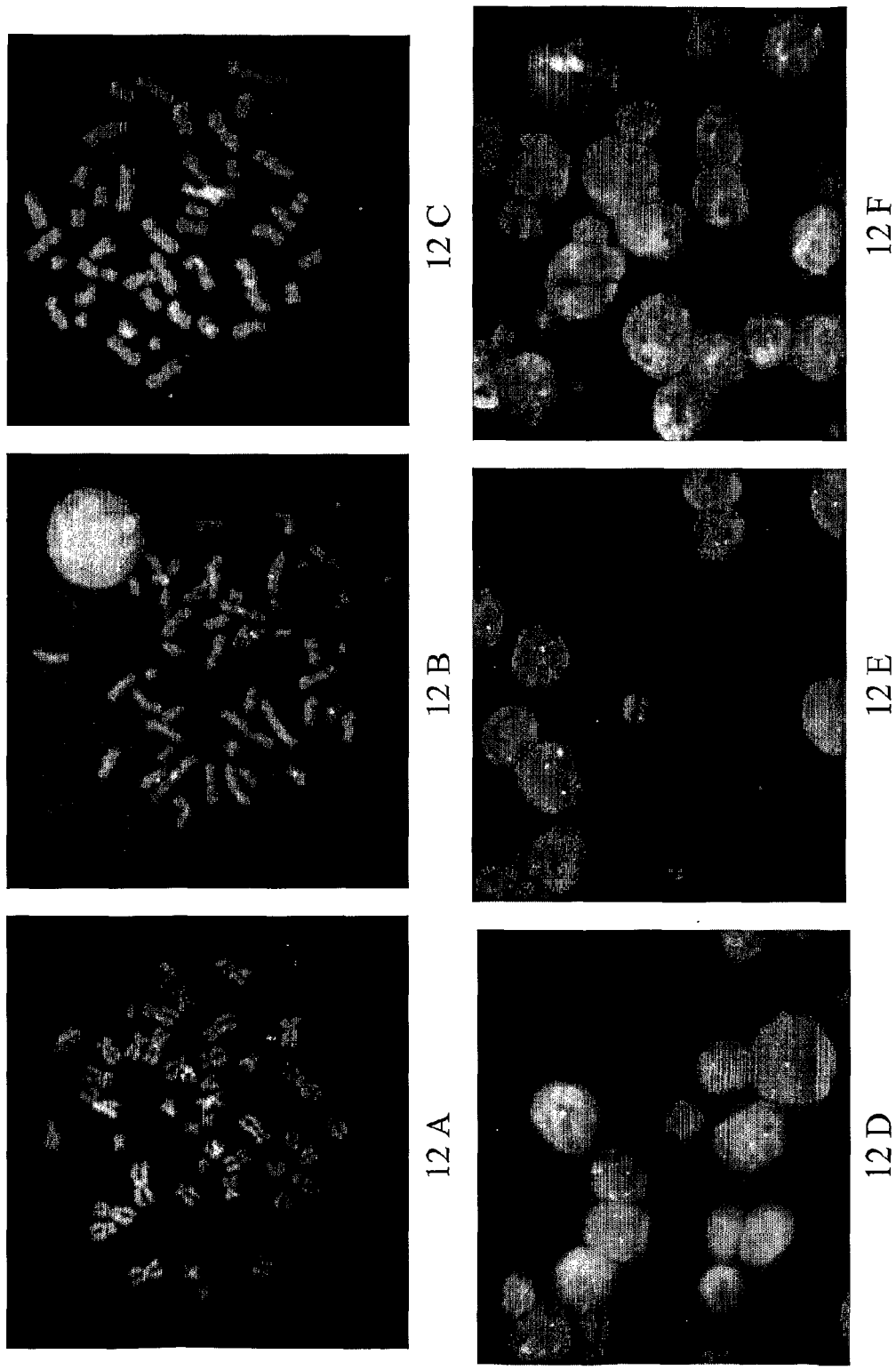

Figure 12 (Cont)
12 I
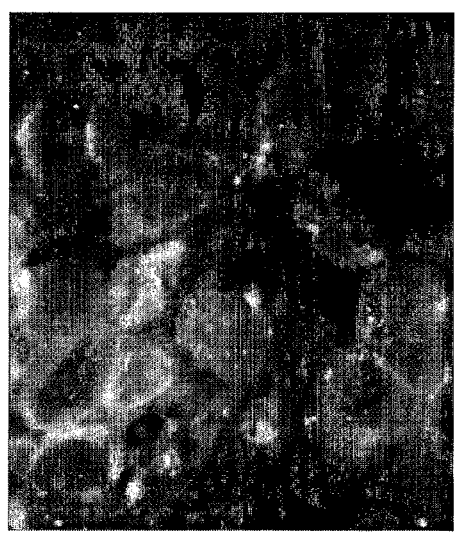
12 H
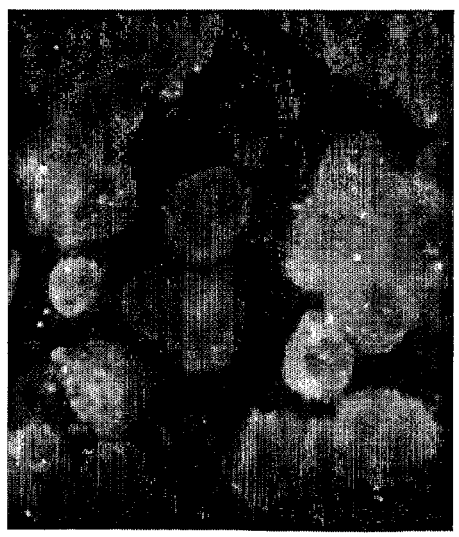
12 G

Figure 17
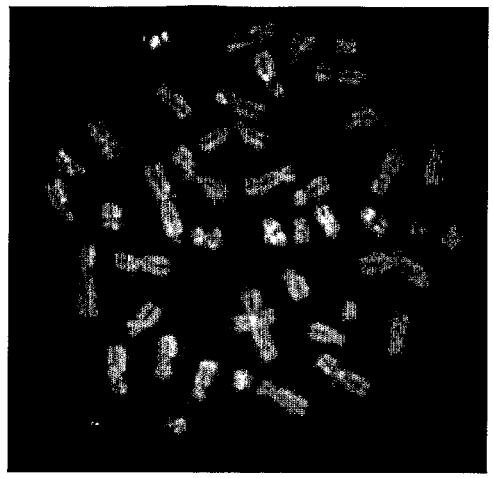
17C
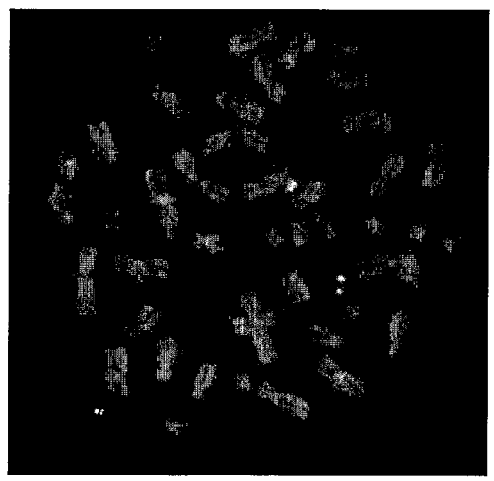
17B
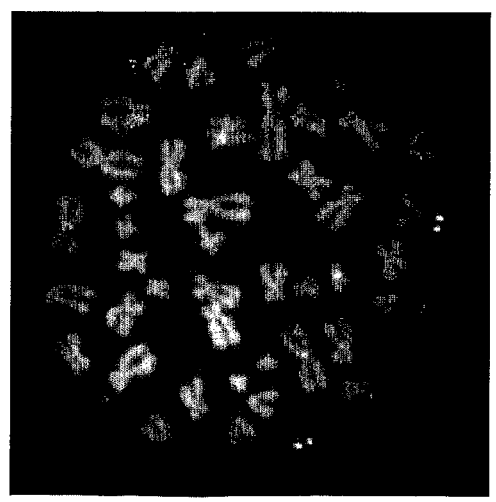
17A

METHODS, KITS AND COMPOSITIONS PERTAINING TO THE SUPPRESSION OF THE DETECTABLE PROBE BINDING TO RANDOMLY DISTRIBUTED REPEAT SEQUENCES IN GENOMIC NUCLEIC ACID

CROSS-REFERENCE TO RELATED APPLICATIONS

This application is a divisional of U.S. application Ser. No. 13/368,732, filed Feb. 8, 2012, now U.S. Pat. No. 8,754,191, which is a continuation of U.S. application Ser. No. 12/619,664, filed Nov. 16, 2009, now abandoned, which is a continuation of U.S. application Ser. No. 10/255,434, filed Sep. 24, 2002, now abandoned, and claims the benefit of U.S. application No. 60/324,499, filed on Sep. 24, 2001, the disclosures of each of which is herein incorporated by reference in its entirety.

BACKGROUND

1. Field of the Invention

This invention pertains to the field of molecular cytogenetics and more specifically this invention pertains methods, kits and compositions being used to suppress the binding of detectable nucleic acid probes to undesired sequences, such as randomly distributed repeat sequences, in genomic nucleic acid.

2. Background

Nucleic acid hybridization is a fundamental process in molecular biology. Probe-based assays are useful in the detection, identification, quantitation and/or analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, nucleic acid probe-based assays have been slow to achieve commercial success. This lack of commercial success is, at least partially, the result of difficulties associated with specificity, sensitivity and/or reliability.

Fluorescence in-situ hybridization (FISH) has become an important tool for determining the number, size and/or location of specific DNA sequences in mammalian cells. Typically, the hybridization reaction fluorescently stains the target sequences so that their location, size and/or number can be determined using fluorescence microscopy, flow cytometry or other suitable instrumentation. DNA sequences ranging from whole genomes down to several kilobases can be studied using current hybridization techniques in combination with commercially available instrumentation.

In Comparative Genomic Hybridization (CGH) whole genomes are stained and compared to normal reference genomes for the detection of regions with aberrant copy number. In the m-FISH technique (multi color FISH) each separate normal chromosome is stained by a separate color (Eils et al, Cytogenetics Cell Genet 82: 160-71 (1998)). When used on abnormal material, the probes will stain the aberrant chromosomes thereby deducing the normal chromosomes from which they are derived (Macville M et al., Histochem Cell Biol. 108: 299-305 (1997)). Specific DNA sequences, such as the ABL gene, can be reliably stained using probes of only 15 kb (Tkachuk et al., Science 250: 559-62 (1990)). FISH-based staining is sufficiently distinct such that the hybridization signals can be seen both in metaphase spreads and in interphase nuclei. Single and multicolor FISH, using nucleic acid probes, have been applied to different clinical applications generally known as molecular cytogenetics, including prenatal diagnosis, leukemia diagnosis, and tumor cytogenetics.

A large component of the human genome comprises repeat sequences. Heat denaturation and reannealing studies on DNA of higher organisms have distinguished three populations of eukaryotic DNA; a quickly reannealing component representing 25% of total DNA, an intermediate component that represents 30% of the total DNA, and a slow component that represents 45% of the total DNA (Britten et al., Science 161: 529-540 (1968)). Sequence analysis has shown that the slow component is made up by single-copy sequences, which include protein encoding genes, while the fast and intermediate components represents repetitive sequences. The fast component contains small (a few nucleotides long), highly repetitive DNA sequences, which are usually found in tandem while the intermediate component contain the interspersed repetitive DNA (Novick et al., Human Genome Bioscience, 46(1): 32-41 (1996) and Brosius J., Science 251: 753 (1991)). The repetitive units of the intermediate component are interspersed within the genome and is the major reason that large genomic nucleic acid probes (i.e. >100 bp) derived from genomic nucleic acid are not well suited for hybridization analysis.

Interspersed repeated sequences are classified as either SINEs (short interspersed repeated sequences) or LINEs (Kroenberg et al., Cell, 53: 391-400 (1988)). In primates, each of these classes are dominated by a single DNA sequence family, both of which are classified as retrosponos (Rogers J., International Review of Cytology, 93: 187-279 (1985)). The major human SINEs are the Alu-repeat DNA sequence family. The Alu-repeat DNA family members are characterized by a consensus sequence of approximately 280 to 300 bp which consist of two similar sequences arranged as a head to tail dimer. Approximately one million copies of the Alu repeat sequence are estimated to be present per haploid human genome, thereby representing about ten percent of the genome (Ausubel et al., Current Protocols In Molecular Biology, John Wiley & Sons, Inc., 1996)). That estimate is consistent with the recent sequence determination of the human chromosome 21 and 22. These reports demonstrate that Alu repeats cover 9.48% and 16.80% of the DNA, respectively (Hattori et al. Nature, 405: 311-319 (2000) and Dunham I. et al., Nature, 402: 489-495 (1999)).

Alu elements have amplified in the human genome through retroposition over the past 65 million years and have been organized into a wealth of overlapping subfamilies based on diagnostic mutations shared by subfamily members (See For Example: Batzer et al., J. Mol. Evol., 42: 3-6 (1996)). Batzer et al. described a consensus nomenclature for Alu repeats sequences; representing the oldest (J), intermediate (S) and young (Y) family branches. Only the Y family branch is still transcriptional active but it is very small as each of the defined a5, a8 and b8 subfamily members have produced less than 2000 elements (Sherry et al., Genetics, 147: 1977-1982 (1997)). It has been calculated that of the primate Alu repeat family branches, approximately one-fifth belong to the J family and four-fifths to the S family (Britten, R. J., Proc. Natl. Acad. Sci. USA, 91: 6148-6150 (1994). The S family is dominated by the Sx subfamily as it represents more than 50% of the total S family branch.

In addition to SINEs and LINEs, there are several other types of repeats that are known to exist in genomic nucleic acid of humans as well as in other organisms. Chromosome telomeres are repeat sequences that appear to exist only, or else predominately, at the termini of all chromosomes. They are believed to shorten during the life of an organism and may play a role in the aging of an organism (See: Landsorp, P., WIPO Patent Application No. WO97/14026). Likewise, chromosome centromeres contain distinct repeat sequences that exist only, or else predominately, in the central (centromere) region of a chromosome. Certain of the centromere repeat sequences can be detected in all chromosomes of an organism whilst other repeat sequences are unique to a particular chromosome and can be used to identify specific chromosomes (Taneja et al., *Genes, Chromosomes & Cancer*, 30: 57-63 (2001)).

Telomere and centromere repeat sequences differ from interspersed repetitive sequence, such as SINE and LINEs, in that the telomere and centromere repeat sequences are localized within a certain region of the chromosome. By comparison, SINEs and LINEs, which are referred to herein as randomly distributed repeat sequences, are dispersed randomly throughout the entire genome (Ullu E., *TIBS:* 216-219 (June, 1982)). Thus, as used herein, the term "randomly distribute repeat sequence" is intended to refer to repeat sequences that occur randomly within all, or essentially all, genomic nucleic acid of an organism. These include, but are not limited to, Alu-repeats, Kpn-repeats, di-nucleotide repeats, tri-nucleotide repeats, tetra-nucleotide repeats, penta-nucleotide repeats, hexa-nucleotide repeats, all of which are more generally classified as SINEs or LINEs.

Detection of specific nucleic acid sequences by in situ hybridization using non-radioactive labels has been applied for almost twenty years. As stated above however, the randomly distributed repeat sequences, such as SINEs and LINEs, are particularly problematic for the production of specific nucleic acid probes that are derived from large clones because the probes will inevitably comprise randomly distributed repeat sequence. The problem arises because the nucleic acid probes will have the randomly distributed repeat sequence contained therein, thereby facilitating hybridization between the randomly distributed repeat sequences of the probes and natural genomic nucleic acid found within all chromosomes. Because the detectable probes hybridize specifically to the target, as well as to repeat sequence that is randomly found in the genomic nucleic acid, there is a high degree of background signal that is produced.

Refinement of non-radioactive detection and visualization methods resulted in improved detection limits and thereby allowed the localization of large single-copy sequences (Landegent et al., *Nature,* 317: 175-177 (1985)). In this study it was necessary to construct a mixture of seven subclones (a total of 22.3 kb derived from a cosmid DNA clone containing the 3' end of the Tg gene) in order to eliminate highly repeated sequences present in the original genomic cosmid DNA. Although this was an improvement, a more attractive strategy, based on direct use of large genomic cloned segments in combination with Cot1 DNA, has been described. The use of Cot1 DNA eliminates background signal, caused by highly repetitive sequences, by introducing a competitive hybridization process (Landegent et al., *Hum. Genet.,* 77: 366-370 (1987); U.S. Pat. No. 5,447,841, issued to Gray et al.; and U.S. Pat. No. 6,203,977 B1 issued to Ward et al.).

Cot1 DNA is a heterogeneous mixture of genomic nucleic acid that is prepared by degrading total human DNA and processing the resulting material to thereby select for genomic nucleic acid fragments that are enriched in the repeat sequences (Britten et el., *Methods Enzymol* 29: 363-418 (1986)). Although the use of Cot1 DNA has been proven to be effective in suppressing undesired binding of detectable nucleic acid fragments of greater that 100 bp to target genomic nucleic acid, there are several disadvantages to this method. One such disadvantage pertains to the preparation of the Cot1 DNA itself. Specifically, because the process relies on the availability of total human DNA, the starting material is itself not highly defined and is likely to vary from sample to sample. Moreover, the processing methods are likely to produce material that varies from batch to batch; this result being somewhat dependent upon the variability of the starting material and somewhat dependent upon the variability of the production process itself. Additionally, the Cot1 DNA is a heterogeneous mixture of fragments that is impossible to completely characterize and define. Hence, the batch to batch variability, as well as the inability to characterize the Cot1 DNA product, leaves substantial room for improvement. The present invention addresses these, as well as other, limitations of the art.

Despite its name, Peptide Nucleic Acid (PNA) is neither a peptide, a nucleic acid nor is it an acid. Peptide Nucleic Acid (PNA) is a non-naturally occurring polyamide (pseudopeptide) that can hybridize to nucleic acid (DNA and RNA) with sequence specificity (See: U.S. Pat. No. 5,539,082 and Egholm et al., *Nature* 365: 566-568 (1993)). Because they hybridize to nucleic acid with sequence specificity, PNA oligomers have become commonly used in probe based applications for the analysis of nucleic acids.

Being a non-naturally occurring molecule, unmodified PNA is not known to be a substrate for the enzymes that are known to degrade peptides or nucleic acids. Therefore, PNA should be stable in biological samples, as well as have a long shelf-life. Unlike nucleic acid hybridization, which is very dependent on ionic strength, the hybridization of a PNA with a nucleic acid is fairly independent of ionic strength and is favored at low ionic strength, conditions that strongly disfavor the hybridization of nucleic acid to nucleic acid (Egholm et al., *Nature, at p.* 567). Because of their unique properties, it is clear that PNA is not the equivalent of a nucleic acid in either structure or function.

Labeled PNA probes have been used for the analysis of rRNA in ISH and FISH assays (See: WO95/32305 and WO97/18325). Labeled PNA probes have also been used in the analysis of mRNA (e.g. Kappa & Lambda Light Chain; Thisted M. et al., *Cell Vision* 3: 358-363 (1996)) and viral nucleic acid (e.g. EBV; Just T et al., *J. Vir. Methods:* 73: 163-174 (1998)). A labeled PNA probe has also been used to detect human X chromosome specific sequences in a PNA-FISH format (See: WO97/18325, now U.S. Pat. No. 5,888,733). The analysis of chromosome aberrations using PNA probes has also been disclosed (See: WO99/57309). The ISH based analysis of eukaryotic chromosomes and cells, using polyamide nucleic acids, has also been suggested (See: U.S. Pat. No. 5,888,734).

Labeled peptide nucleic acids have been described for the analysis of both telomere and centromere repeat sequences in genomic nucleic acid (Lansdorp, P., WO97/14026). Likewise, labeled peptide nucleic acid oligomers have been used in the analysis of individual human chromosomes in a multiplex PNA-FISH assay (Taneja et al., *Genes, Chromosomes & Cancer,* 30: 57-63 (2001). Similarly, the analysis of trinucleotide repeats in chromosomal DNA, using appropriate labeled PNA probes, has also been suggested (See: WO97/14026). Subsequently, DNA and PNA probes were used to examine cells for genetic defects associated with the expansion of trinucleotide repeats that manifest as the disease known as human myotonic dystrophy (See: Taneja,

*Biotechniques*, 24: 472-476 (1998)). In all cases, labeled PNA probes were used to detect the specific target nucleic acid repeat sequences.

PNA oligomers comprising the triplet repeat sequence CAG have also been used for the selective isolation of transcriptionally active chromatin restriction fragments (See: Boffa et al., Proc. Nat'l. Acad. Sci. USA, 92: 1901-1905 (1995)).

Peptide nucleic acid oligomers have also been used to suppress the binding of detectable probes to non-target sequences (See: U.S. Pat. No. 6,110,676). Importantly however, there is no specific description, suggestion or teaching of using peptide nucleic acid oligomers to suppress the binding of detectable nucleic acid probes to undesired randomly distributed repeat sequences of genomic nucleic acid.

SUMMARY OF THE INVENTION

Generally, this invention is directed to methods, kits, non-nucleotide probes as well as other compositions pertaining to the suppression of binding of detectable nucleic acid probes to undesired nucleotide sequences of genomic nucleic acid in assays designed to determine target genomic nucleic acid. In many cases, the most problematic undesired nucleotide sequences are SINEs and LINEs (i.e. randomly distributed repeat sequence), which include, but are not limited to, Alu-repeats, Kpn-repeats, di-nucleotide repeats, tri-nucleotide repeats, tetra-nucleotide repeats, penta-nucleotide repeats and hexa-nucleotide repeats.

In one embodiment, this invention pertains to a non-nucleotide probe of at least sixteen nucleobase containing subunits in length having an aggregate nucleobase sequence that is at least eighty percent homologous to a sixteen nucleotide segment of randomly distributed repeat sequence of genomic nucleic acid. By homologous, we mean nucleobase sequence homology. By aggregate nucleobase sequence we mean the nucleobase sequence comprising the aggregate of nucleobase containing subunits of the probe even if separated by one or more linkers. The nucleobase sequence of the non-nucleotide probe can be substantially or completely homologous to a fraction, or part, of either: (i) a known unit repeat of Alu-repeat sequence; or (ii) a consensus sequence of a known unit repeat of Alu-repeat sequence. The nucleobase sequence of the non-nucleotide probe can be at least eighty percent homologous to a sixteen nucleotide segment of the consensus unit repeat of Alu-repeat selected from the group consisting of: Seq. Id. No. 1 and Seq. Id. No. 2 (See: Table 1). The non-nucleotide probe can be a peptide nucleic acid.

In another embodiment, this invention pertains to a non-nucleotide probe containing an aggregate nucleobase sequence of at least ten consecutive nucleobases that is at least eighty percent homologous to the nucleobase sequences selected from the group consisting of: Seq. Id. No. 3, Seq. Id. No. 4, Seq. Id. No. 5, Seq. Id. No. 6, Seq. Id. No. 7, Seq. Id. No. 8, Seq. Id. No. 9, Seq. Id. No. 10, Seq. Id. No. 11, Seq. Id. No. 12, Seq. Id. No. 13, Seq. Id. No. 14, Seq. Id. No. 15, Seq. Id. No. 16, Seq. Id. No. 17, Seq. Id. No. 18, Seq. Id. No. 19, Seq. Id. No. 20, Seq. Id. No. 21, Seq. Id. No. 22, Seq. Id. No. 23, Seq. Id. No. 24, Seq. Id. No. 25 and Seq. Id. No. 26 (See: Table 1). These particular sequences, or their complements, have been determined to be highly effective at suppressing the binding of a detectable nucleic acid probe to undesired chromosomes or chromosome regions in an assay for detecting the ERBB2 (alias HER2) or MLL target nucleic acid sequence in genomic nucleic acid (See: Examples 4 and 5). The ten consecutive nucleobases can be either: (i) at least ninety percent homologous to the identified sequences; or (ii) exactly homologous to the identified sequences. The probe can be identical in nucleobase sequence to any one of the identified sequences. The non-nucleotide probe can be a peptide nucleic acid oligomer.

In still another embodiment, this invention pertains to a mixture of two or more non-nucleotide probes wherein each probe contains an aggregate nucleobase sequence that is at least eighty percent homologous to a sixteen nucleotide segment of randomly distributed repeat sequence of genomic nucleic acid. The randomly distributed repeat sequence can be a SINE or LINE. SINEs and LINEs can be selected from the group consisting of: Alu-repeats, Kpn-repeats, di-nucleotide repeats, tri-nucleotide repeats, tetra-nucleotide repeats, penta-nucleotide repeats and hexa-nucleotide repeats. The non-nucleotide probes can be peptide nucleic acid oligomers. The mixture of probes can further comprise one or more detectable nucleic acid probes.

In yet another embodiment, this invention pertains to a composition comprising genomic nucleic acid containing one or more segments of randomly distributed repeat sequence. The randomly distributed repeat sequence can be a SINE or LINE. SINEs and LINES can be selected from the group consisting of: Alu-repeats, Kpn-repeats, di-nucleotide repeats, tri-nucleotide repeats, tetra-nucleotide repeats, penta-nucleotide repeats and hexa-nucleotide repeats. The composition can further comprise two or more different non-nucleotide probes that sequence specifically hybridized to at least a fraction, or part, of the one or more segments of randomly distributed repeat sequence of the genomic nucleic acid. Hence, the composition can be the hybrid of the segment of randomly distributed repeat sequence and the two or more non-nucleotide probes. The non-nucleotide probes can be peptide nucleic acid oligomers.

Because it may be desirable to provide the mixture of non-nucleotide probes in the same container as the detectable nucleic acid probes, and because the detectable nucleic acid probes can possess segments of nucleobase sequence that are derived from the randomly distributed repeat sequences, this invention is further directed to a composition comprising a detectable nucleic acid probe of at least 100 bp that has been derived from genomic nucleic acid and that contains one or more segments of randomly distributed repeat sequence. The randomly distributed repeat sequences can be SINEs or LINEs. The SINEs or LINEs can be selected from the group consisting of: Alu-repeats, Kpn-repeats, di-nucleotide repeats, tri-nucleotide repeats, tetra-nucleotide repeats, penta-nucleotide repeats and hexa-nucleotide repeats. The composition can further comprise two or more different non-nucleotide probes sequence specifically hybridized to at least a fraction of the one or more segments of randomly distributed repeat sequence of the detectable nucleic acid probe. The non-nucleotide probes can be peptide nucleic acid oligomers.

In still another embodiment, this invention is directed to a method for suppressing the binding of one or more detectable nucleic acid probes, that are greater than 100 bp and that have been derived from genomic nucleic acid, to one or more undesired sequences in an assay for determining target genomic nucleic acid of a sample. The method comprises contacting the sample with a mixture of two or more non-nucleotide probes wherein each probe contains an aggregate nucleobase sequence that is at least eighty percent homologous to a segment of randomly distributed repeat sequence of genomic nucleic acid. According to the method, the sample is also contacted with the one or more detectable nucleic acid probes. The target genomic nucleic acid of the sample can then determined by determining the hybridization of the one or more detectable nucleic acid probes to the target genomic nucleic acid of the sample wherein the presence, absence or amount of hybridization of the detectable nucleic acid probe to the target genomic nucleic acid is representative of the presence, absence or amount of target genomic nucleic acid in the sample. The non-nucleotide probes can be peptide nucleic acid oligomers.

Thus, in yet another embodiment, this invention pertains to comparing a sample of genomic nucleic acid with that of a control sample using a genomic nucleic acid reference array. The method comprises providing a sample of genomic nucleic acid to be tested, providing a control of genomic nucleic acid, wherein the control and the sample are differentially labeled, providing a genomic nucleic acid reference array, and providing a mixture of two or more non-nucleotide probes wherein each probe contains an aggregate nucleobase sequence that is at least eighty percent homologous to a sixteen nucleotide segment of randomly distributed repeat sequence of genomic nucleic acid. The method further comprises treating the sample and control genomic nucleic acid, the array or both the sample and control genomic nucleic acid and the array with the mixture of non-nucleotide probes under suitable hybridization conditions. The array can then be contacted with the treated mixture of sample and control genomic nucleic acid under suitable hybridization conditions. The intensities of the signals from the differential labels on the array, caused by hybridization of the probes to genomic nucleic acid, can then be compared to thereby determine one or more variations in copy numbers of sequences in the sample as compared with the relative copy numbers of substantially identical sequences in the control.

In still another embodiment, this invention is directed to a method for determining non-nucleotide probes that hybridize to randomly distributed repeat sequences and that are suitable for suppressing the binding of a detectable nucleic acid probe, that is greater than 100 bp in length and that is derived from genomic nucleic acid, to one or more undesirable sequences in an assay for determining target genomic nucleic acid of a sample. The method comprises designing possible nucleobase sequences of non-nucleotide probes using sequence alignment of known randomly distributed repeat sequences and then preparing labeled non-nucleotide probes having said possible nucleobase sequences. According to the method, genomic nucleic acid of a sample that contains the target genomic nucleic acid can be treated with the labeled non-nucleotide probes under suitable hybridization conditions. The relative signal of the hybridized labeled probes of the many different possible nucleobase sequences can then be determined. Based upon the signal intensity data, the probe or probes that exhibit the strongest signal, as a result of binding to the genomic nucleic acid, can be selected and tested to thereby determine whether or not they are suitable for suppressing the binding of a detectable nucleic acid probe of greater than 100 bp in length that is derived from genomic nucleic acid to one or more non-target sequences in an assay for determining target genomic nucleic acid of a sample. In order to test the probe or probes, they can be re-synthesized in unlabeled form and then tested using the method for suppressing the binding of detectable probes to undesired sequences as described above. The non-nucleotide probes can be peptide nucleic acid oligomers.

In still another embodiment, this invention is directed to a reagent kit comprising a mixture of two or more non-nucleotide probes containing at least sixteen consecutive nucleobases that are at least eighty percent homologous to a fraction of the unit repeat Alu-repeat consensus sequence selected from the group consisting of: Seq. Id. No. 1 or Seq. Id. No. 2. The kit further comprises other reagents, compositions and/or instructions suitable for performing an assay to thereby determine genomic nucleic acid of a sample. The reagent kit can further comprise one or more detectable nucleic acid probes of greater than 100 bp in length and that are derived from genomic nucleic acid. The one or more detectable nucleic acid probes can be provided in the container that contains the mixture of two or more non-nucleotide probes.

In yet still another embodiment, this invention is directed to a kit comprising a mixture of two or more non-nucleotide probes wherein at least one probe contains a segment of at least ten consecutive nucleobases that are at least eighty percent homologous to the Alu-repeat sequences selected from the group consisting of: Seq. Id. No. 3, Seq. Id. No. 4, Seq. Id. No. 5, Seq. Id. No. 6, Seq. Id. No. 7, Seq. Id. No. 8, Seq. Id. No. 9, Seq. Id. No. 10, Seq. Id. No. 11, Seq. Id. No. 12, Seq. Id. No. 13, Seq. Id. No. 14, Seq. Id. No. 15, Seq. Id. No. 16, Seq. Id. No. 17, Seq. Id. No. 18, Seq. Id. No. 19, Seq. Id. No. 20, Seq. Id. No. 21, Seq. Id. No. 22, Seq. Id. No. 23, Seq. Id. No. 24, Seq. Id. No. 25 and Seq. Id. No. 26 (See: Table 1). The kit further comprises other reagents, compositions and/or instructions for performing a assay to thereby determine genomic nucleic acid of a sample. The kit can further comprise one or more detectable nucleic acid probes of greater than 100 bp in length and that are derived from genomic nucleic acid. In a most preferred embodiment, one or more detectable nucleic acid probes can be provided in the container that contains the mixture of two or more non-nucleotide probes.

BRIEF DESCRIPTION OF THE DRAWINGS

FIGS. 2-1, 2-2 and 2-3 are together output from sequence alignment software with the five Alu sequences HSU14574.seq Sx (Seq. Id. No. 30), HSU14573.seq Sq (Seq. Id. No. 31), HSU14572.seq Sp (Seq. Id. No. 32), HSU14571.seq Sc (Seq. Id. No. 33), and HSU14567.seq J (Seq. Id. No. 34)) and the Majority consensus sequence (SEQ ID NO. 29).

FIGS. 3A-1, 3A-2, 3B-1 and 3B-2 are microscope generated images of interphase nuclei and metaphase spread of human chromosomes treated with labeled PNA oligomers that either obtained a high R-banding score (3A-1 & 3A-2) or that just passed the defined lower limit for a suitable R-banding pattern score (3B-1 & 3B-2).

FIGS. 4A, 4B, 4C and 4D are microscope generated images of a metaphase spread of human chromosomes treated with labeled PNA oligomers designed from the J and S family consensus (4A & 4B) or the Y family consensus (4C & 4D).

FIGS. 12A, 12B, 12C, 12D, 12E, 12F, 12G, 12H and 12I are microscope generated images of interphase nuclei and metaphase spreads treated to determine the TOP2A deletion.

FIGS. 17A, 17B and 17C are microscope generated images of interphase nuclei and metaphase spreads treated to determine the IGL gene.

DETAILED DESCRIPTION OF THE INVENTION

1. Definitions

Figure 1:
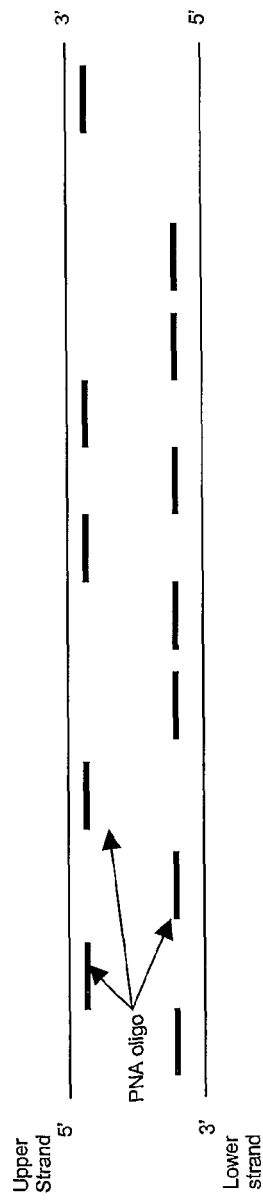
FIG. 1 is an illustration of the positioning of probes on the individual strands within complementary strands of a unit repeat of an Alu-repeat consensus sequence.

For the purposes of interpreting this specification the following definitions shall apply and whenever appropriate, terms used in the singular shall also include the plural and vice versa.

a. As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobases include those nucleobases illustrated in FIGS. 2(A) and 2(B) of Buchardt et al. (U.S. Pat. No. 6,357,163).

b. As used herein, "sequence specifically" means hybridization by base pairing through hydrogen bonding. Non-limiting examples of standard base pairing includes adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: 2-aminopurine, N9-(2-amino-6-chloropurine) or N9-(2,6-diaminopurine); and N8-(7-deaza-8-aza-adenine), being a universal base, base pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine) or N9-(7-deaza-8-aza-guanine) (See: Seela et al., Nucl. Acids, Res.: 28(17): 3224-3232 (2000)).

c. As used herein, "nucleobase sequence" means all or a segment of nucleobase-containing subunits in an oligomer or polymer. Non-limiting examples of suitable polymers or polymers segments that comprise "nucleobase sequence" or "nucleobase sequences" include oligodeoxynucleotides (e.g. DNA), oligoribonucleotides (e.g. RNA), peptide nucleic acids (PNA), nucleic acid analogs and/or nucleic acid mimics.

d. As used herein, "target sequence" or "target genomic nucleic acid" is a nucleobase sequence sought to be determined. The nucleobase sequence can be a subsequence of a nucleic acid molecule of interest (e.g. a chromosome).

e. As used herein, "nucleic acid" is a nucleobase sequence-containing oligomer, polymer, or polymer segment, having a backbone formed solely from nucleotides, or analogs thereof. Preferred nucleic acids are DNA and RNA. For the avoidance of doubt, a peptide nucleic acid (PNA) oligomer is not a nucleic acid since it is not formed from nucleotides or analogs thereof.

f. As used herein, "nucleotide" means any of several compounds that consist of a ribose or deoxyribose sugar joined to a purine or pyrimidine base and to a phosphate group. Nucleotides are the basic structural subunits of nucleic acids (e.g. RNA and DNA).

g. As used herein, "analog" or "nucleic acid analog" means an oligomer, polymer, or polymer segment composed of at least one modified nucleotide, or subunits derived directly a modification of nucleotides.

h. As used herein, "mimic" of "nucleic acid mimic" means a non-nucleotide polymer.

i. As used herein, a "non-nucleotide polymer" or "non-nucleotide probe" is a nucleobase sequence-containing oligomer, polymer, or polymer segment that does not comprise nucleotides. A most preferred non-nucleotide polymer is a peptide nucleic acid (PNA) oligomer.

j. As used herein, "peptide nucleic acid" or "PNA" means any oligomer or polymer comprising two or more PNA subunits (residues), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163;

all of which are herein incorporated by reference. The term "peptide nucleic acid" or "PNA" shall also apply to any oligomer or polymer segment comprising two or more subunits of those nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:5 55-560 (1997); Howarth et al., *J. Org. Chem.* 62: 5441-5450 (1997); Altmann, K-H et al., *Bioorganic & Medicinal Chemistry Letters*, 7: 1119-1122 (1997); Diederichsen, U., *Bioorganic & Med. Chem. Lett.*, 8: 165-168 (1998); Diederichsen et al., *Angew. Chem. Int. Ed.*, 37: 302-305 (1998); Cantin et al., *Tett. Lett.*, 38: 4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000.

In certain embodiments, a "peptide nucleic acid" or "PNA" is an oligomer or polymer segment comprising two or more covalently linked subunits of the formula:

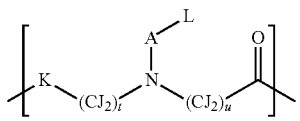

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms that may optionally contain a heteroatom or a substituted or unsubstituted aryl group. Each A is selected from the group consisting of a single bond, a group of the formula; —$(CJ_2)_s$- and a group of the formula; —$(CJ_2)_sC(O)$—, wherein, J is defined above and each s is a whole number from one to five. Each t is 1 or 2 and each u is 1 or 2. Each L is the same or different and is independently selected from: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), other naturally occurring nucleobase analogs or other non-naturally occurring nucleobases.

In certain other embodiments, a PNA subunit consists of a naturally occurring or non-naturally occurring nucleobase attached to the N-α-glycine nitrogen of the N-[2-(aminoethyl)]glycine backbone through a methylene carbonyl linkage; this currently being the most commonly used form of a peptide nucleic acid subunit.

k. As used herein, the terms "label", "reporter moiety" or "detectable moiety" are interchangeable and refer to moieties that can be attached to an oligomer or polymer to thereby render the oligomer or polymer detectable by an instrument or method.

l. As used herein, "stained" means that individual organisms, chromosomes or chromosome fragments or segments are directly or indirectly marked with a detectable moiety as a result of the sequence specific hybridization thereto of one or more detectable probes.

m. As used herein, "unit repeat" means the basic unit of nucleobase sequence that is repeated in a randomly distributed repeat sequence.

n. As used herein, "block", "oligomer block" or "block oligomer" are interchangeable and all mean a PNA oligomer that is designed and available to be ligated to a second appropriately modified PNA oligomer to thereby prepare an elongated PNA oligomer. Oligomers or blocks that are ligated/condensed may be unlabeled, labeled with one or more reporter moieties and/or comprise one or more protected or unprotected functional groups. With respect to an elongated oligomer, "block" can also be used to refer to a part of the elongated oligomer that originates from an oligomer block used to form the elongated oligomer. The elongated oligomer also may be used as a block in a ligation/condensation reaction that further elongates the PNA oligomer.

2. Description of the Invention

I. General

Production, Purification & Labeling of Detectable Nucleic Acid Probes

To amplify a specific DNA sequence by cloning, the DNA can be inserted into a vector and both insert and vector can then be amplified inside appropriate host cells. The amplified DNA can then extracted. Commonly used vectors include bacterial plasmids, cosmids, PACs, BACs, and YACs.

The purified DNA can be labeled with different methods, e.g. enzymatic or chemical. The most frequently used method is Nick translation. The Nick translation reaction can employ two enzymes, Dnase I which produces the "nicks" in the double-stranded DNA and DNA polymerase, which incorporates labeled nucleotides along both strands of the DNA duplex. Any labeling method known to those in the art can be used for labeling the nucleic acid probe as used in this invention.

PNA Synthesis:

Methods for the chemical assembly of PNAs are well known (See: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,201,103, 6,228,982 and 6,357,163; all of which are herein incorporated by reference (Also see: PerSeptive Biosystems Product Literature)). As a general reference for PNA synthesis methodology also please see: Nielsen et al., *Peptide Nucleic Acids; Protocols and Applications*, Horizon Scientific Press, Norfolk England (1999).

Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that is condensed with the next synthon to be added to the growing polymer.

PNA may be synthesized at any scale, from submicromole to millimole, or more. PNA can be conveniently synthesized at the 2 µmole scale, using Fmoc (Bhoc), tBoc/Z, or MmT protecting group monomers on an Expedite Synthesizer (Applied Biosystems) using a XAL or PAL support. Alternatively the Model 433A Synthesizer (Applied Biosystems) with MBHA support can be used. Moreover, many other automated synthesizers and synthesis supports can be utilized. Because standard peptide chemistry is utilized, natural and non-natural amino acids can be routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA oligomers can also be prepared by the ligation of shorter oligomers, with (See: WO02/072865) or without (See: U.S. Ser. No. 60/409,220) the introduction of a linker contained therebetween the oligomer blocks.

PNA Labeling/Modification:

Non-limiting methods for labeling PNAs are described in U.S. Pat. No. 6,110,676, U.S. Pat. No. 6,280,964, U.S. Pat. No. 6,355,421, WO99/21881, U.S. Pat. No. 6,361,942, WO99/49293 and U.S. Pat. No. 6,441,152 (all of which are herein incorporated by reference), the examples section of this specification or are otherwise well known in the art of PNA synthesis and peptide synthesis. Methods for labeling PNA are also discussed in Nielsen et al., *Peptide Nucleic Acids; Protocols and Applications*, Horizon Scientific Press, Norfolk, England (1999). Non-limiting methods for labeling PNA oligomers are discussed below.

Because the synthetic chemistry of assembly is essentially the same, any method commonly used to label a peptide can often be adapted to effect the labeling a PNA oligomer. Generally, the N-terminus of the oligomer or polymer can be labeled by reaction with a moiety having a carboxylic acid group or activated carboxylic acid group. One or more spacer moieties can optionally be introduced between the labeling moiety and the nucleobase containing subunits of the oligomer. Generally, the spacer moiety can be incorporated prior to performing the labeling reaction. If desired, the spacer may be embedded within the label and thereby be incorporated during the labeling reaction.

Typically the C-terminal end of the polymer can be labeled by first condensing a labeled moiety or functional group moiety with the support upon which the PNA oligomer is to be assembled. Next, the first nucleobase containing synthon of the PNA oligomer can be condensed with the labeled moiety or functional group moiety. Alternatively, one or more spacer moieties (e.g. 8-amino-3,6-dioxaoctanoic acid; the "O-linker") can be introduced between the label moiety or functional group moiety and the first nucleobase subunit of the oligomer. Once the molecule to be prepared is completely assembled, labeled and/or modified, it can be cleaved from the support deprotected and purified using standard methodologies.

For example, the labeled moiety or functional group moiety can be a lysine derivative wherein the $\epsilon$-amino group is a protected or unprotected functional group or is otherwise modified with a reporter moiety. The reporter moiety could be a fluorophore such as 5(6)-carboxyfluorescein, Dye1, Dye2 or a quencher moiety such as 4-((4-(dimethylamino) phenyl)azo)benzoic acid (dabcyl). Condensation of the lysine derivative with the solid support can be accomplished using standard condensation (peptide) chemistry. The $\alpha$-amino group of the lysine derivative can then be deprotected and the nucleobase sequence assembly initiated by condensation of the first PNA synthon with the $\alpha$-amino group of the lysine amino acid. As discussed above, a spacer moiety may optionally be inserted between the lysine amino acid and the first PNA synthon by condensing a suitable spacer (e.g. Fmoc-8-amino-3,6-dioxaoctanoic acid) with the lysine amino acid prior to condensation of the first PNA synthon.

Alternatively, a functional group on the assembled, or partially assembled, polymer can be introduced while the oligomer is still support bound. The functional group will then be available for any purpose, including being used to either attached the oligomer to a support or otherwise be reacted with a reporter moiety, including being reacted post-ligation (by post-ligation we mean at a point after the oligomer has been fully formed by the performing of one or more condensation/ligation reactions). This method, however, requires that an appropriately protected functional group be incorporated into the oligomer during assembly so that after assembly is completed, a reactive functional can be generated. Accordingly, the protected functional group can be attached to any position within the oligomer or block, including, at the oligomer termini, at a position internal to the oligomer.

For example, the $\epsilon$-amino group of a lysine could be protected with a 4-methyl-triphenylmethyl (Mtt), a 4-methoxy-triphenylmethyl (MMT) or a 4,4'-dimethoxytriphenylmethyl (DMT) protecting group. The Mtt, MMT or DMT groups can be removed from the oligomer (assembled using commercially available Fmoc PNA monomers and polystyrene support having a PAL linker; PerSeptive Biosystems, Inc., Framingham, Mass.) by treatment of the synthesis resin under mildly acidic conditions. Consequently, a donor moiety, acceptor moiety or other reporter moiety, for example, can then be condensed with the $\epsilon$-amino group of the lysine amino acid while the polymer is still support bound. After complete assembly and labeling, the polymer can then cleaved from the support, deprotected and purified using well-known methodologies.

By still another method, the reporter moiety can be attached to the oligomer or oligomer block after it is fully assembled and cleaved from the support. This method is preferable where the label is incompatible with the cleavage, deprotection or purification regimes commonly used to manufacture the oligomer. By this method, the PNA oligomer can be labeled in solution by the reaction of a functional group on the polymer and a functional group on the label. Those of ordinary skill in the art will recognize that the composition of the coupling solution will depend on the nature of oligomer and label, such as for example a donor or acceptor moiety. The solution may comprise organic solvent, water or any combination thereof. Generally, the organic solvent will be a polar non-nucleophilic solvent. Non limiting examples of suitable organic solvents include acetonitrile (ACN), tetrahydrofuran, dioxane, methyl sulfoxide, N,N'-dimethylformamide (DMF) and 1-methylpyrrolidone (NMP).

The functional group on the polymer to be labeled can be a nucleophile (e.g. an amino group) and the functional group on the label can be an electrophile (e.g. a carboxylic acid or activated carboxylic acid). It is however contemplated that this can be inverted such that the functional group on the polymer can be an electrophile (e.g. a carboxylic acid or activated carboxylic acid) and the functional group on the label can be a nucleophile (e.g. an amino acid group).

Non-limiting examples of activated carboxylic acid functional groups include N-hydroxysuccinimidyl esters. In aqueous solutions, the carboxylic acid group of either of the PNA or label (depending on the nature of the components chosen) can be activated with a water soluble carbodiimide. The reagent, 1-ethyl-3-(3-dimethylamino-propyl)carbodiimide hydrochloride (EDC), is a commercially available reagent sold specifically for aqueous amide forming condensation reactions. Such condensation reactions can also be improved when 1-Hydroxy-7-azabenzotriazole (HOAt) or 1-hydroxybenzotriazole (HOBt) is mixed with the EDC.

The pH of aqueous solutions can be modulated with a buffer during the condensation reaction. For example, the pH during the condensation can be in the range of 4-10. Generally, the basicity of non-aqueous reactions will be modulated by the addition of non-nucleophilic organic bases. Non-limiting examples of suitable bases include N-methylmorpholine, triethylamine and N,N-diisopropyl-ethylamine. Alternatively, the pH can be modulated using biological buffers such as (N-[2-hydroxyethyl]piperazine-N'-[2-ethanesulfonic acid) (HEPES) or 4-morpholineethanesulfonic acid (MES) or inorganic buffers such as sodium bicarbonate.

Labeled Oligomers & Oligomer Blocks:

As discussed above, PNA oligomers can be labeled with reporter moieties. Non-limiting examples of reporter moieties (labels) suitable for directly labeling oligomers or oligomer blocks include: a quantum dot, a minor groove binder, a dextran conjugate, a branched nucleic acid detection system, a chromophore, a fluorophore, a quencher, a spin label, a radioisotope, an enzyme, a hapten, an acridinium ester and a chemiluminescent compound. Quenching moieties are also considered labels. Other suitable labeling reagents and preferred methods of attachment would be recognized by those of ordinary skill in the art of PNA, peptide or nucleic acid synthesis. Non-limiting examples are described or referred to above.

Non-limiting examples of haptens include 5(6)-carboxyfluorescein, 2,4-dinitrophenyl, digoxigenin, and biotin.

Non-limiting examples of fluorochromes (fluorophores) include 5(6)-carboxyfluorescein (Flu), 2',4',1,4-tetrachlorofluorescein; and 2',4',5',7',1,4-hexachlorofluorescein, other fluorescein dyes (See: U.S. Pat. Nos. 5,188,934; 6,008,379; 6,020,481, incorporated herein by reference), 6-((7-amino-4-methylcoumarin-3-acetyl)amino)hexanoic acid (Cou), 5(and 6)-carboxy-X-rhodamine (Rox), other rhodamine dyes (See: U.S. Pat. Nos. 5,366,860; 5,847,162; 5,936,087; 6,051,719; 6,191,278; 6,248,884, incorporated herein by reference), benzophenoxazines (See: U.S. Pat. No. 6,140,500, incorporated herein by reference) Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), other cyanine dyes (Kubista, WO 97/45539), 6-carboxy-4',5'-dichloro-2',7'-dimethoxyfluorescein (JOE), 5(6)-carboxy-tetramethyl rhodamine (Tamara), Dye 1 (FIG. 7), Dye2 (FIG. 7) or the Alexa dye series (Molecular Probes, Eugene, Oreg.).

Non-limiting examples of enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

Non-limiting examples of quenching moieties include diazo-containing moieties such as aryldiazo compounds, e.g. dabcyl and dabsyl, homologs containing one more additional diazo and/or aryl groups; e.g. Fast Black, (Nardone, U.S. Pat. No. 6,117,986), and substituted compounds where Z is a substituent such Cl, F, Br, $C_1$-$C_6$ alkyl, $C_5$-$C_{14}$ aryl, nitro, cyano, sulfonate, $NR_2$, —OR, and $CO_2H$, where each R is independently H, $C_1$-$C_6$ alkyl or $C_5$-$C_{14}$ aryl according to the structures:

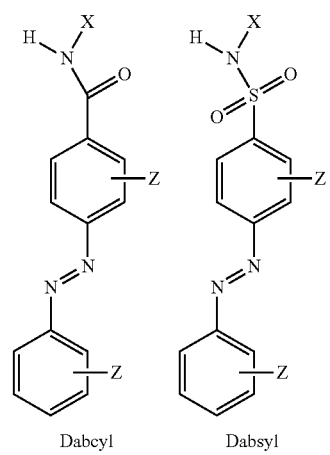

Dabcyl      Dabsyl cyanine dyes (Lee, U.S. Pat. No. 6,080,868), including the exemplary structure:

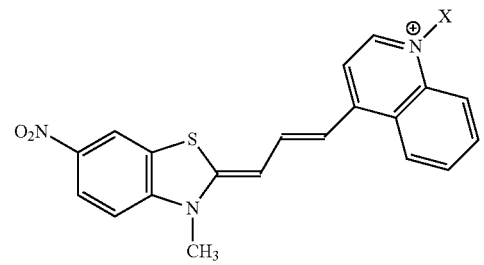

and other chromophores such as anthraquinone, malachite green, nitrothiazole, and nitroimidazole compounds and the like wherein the group X is the covalent attachment site of a bond or linker to the oligomers of the invention.

A non-limiting example of a minor groove binder is $CDPI_3$, represented by the structure:

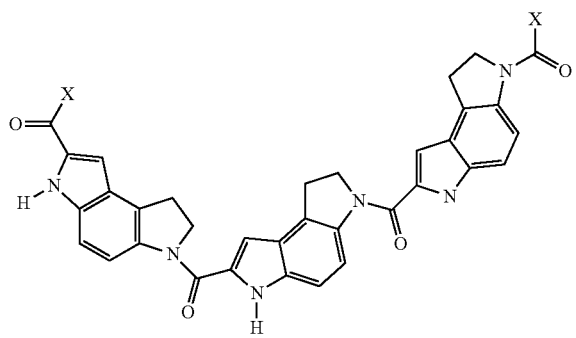

where X are exemplary attachment sites to a oligomer (Dempcy, WO 01/31063).

Non-radioactive labeling methods, techniques, and reagents are reviewed in: *Non-Radioactive Labeling, A Practical Introduction*, Garman, A. J. Academic Press, San Diego, Calif. (1997).

Detectable and Independently Detectable Moieties/Multiplex Analysis:

In preferred embodiments of this invention, a multiplex hybridization assay is performed. In a multiplex assay, numerous conditions of interest are simultaneously or sequentially examined. Multiplex analysis relies on the ability to sort sample components or the data associated therewith, during or after the assay is completed. In one embodiments, one or more distinct independently detectable moieties can be used to label two or more different detectable nucleic acid probes used in an assay. The ability to differentiate between and/or quantitate each of the independently detectable moieties provides the means to multiplex a hybridization assay because the data correlates with the hybridization of each of the distinct, independently labeled oligomer to a particular target sequence sought to be detected in the sample. Consequently, the multiplex assays of this invention may be used to simultaneously or sequentially detect the presence, absence, number, position and/or identity of two or more target sequences in the same sample and/or in the same assay.

Spacer/Linker Moieties:

Generally, spacers are used to minimize the adverse effects that bulky labeling reagents might have on the hybridization properties of probes or primers. A linker is used to link two or more segments of an oligomer or polymer. Non-limiting examples of spacer/linker moieties used in this invention consist of: one or more aminoalkyl carboxylic acids (e.g. aminocaproic acid) the side chain of an amino acid (e.g. the side chain of lysine or ornithine) one or more natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the oligomer (For example see: Gildea et al., *Tett. Lett.* 39: 7255-7258 (1998)).

Hybridization Conditions/Stringency:

Those of ordinary skill in the art of hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target sequence combination is often found by the well-known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more carefully stringency must be controlled. Suitable hybridization conditions will thus comprise conditions under which the desired degree of discrimination is achieved such that an assay generates an accurate (within the tolerance desired for the assay) and reproducible result. Nevertheless, aided by no more than routine experimentation and the disclosure provided herein, those of skill in the art will easily be able to determine suitable hybridization conditions for performing assays utilizing the methods and compositions described herein.

Probing Nucleobase Sequence:

The probing nucleobase sequence of probe is the specific sequence recognition portion of the construct. Therefore, the probing nucleobase sequence is an aggregate nucleobase sequence of the probe that is designed to hybridize to a specific target sequence of interest in a sample. By aggregate nucleobase sequence, we refer to the totality of the nucleobase subunits that bind to the target sequence without regard to whether or not they comprise one or more linkages atypical to the backbone of the polymer (e.g. two segments of continuous nucleobase sequence containing subunits separated by a linker). The target sequence can be a sequence that identifies a gene such as for example, the CyclinD1 gene, the c-MYC gene, the EGFR gene, the TEL gene, the E2A gene, the BCR gene, the IGH gene, the IGL gene or the IGK gene.

Advantages of the Present Invention:

The non-nucleotide probes of this invention can be chemically synthesized and purified in a manner that provides for low cost and proper characterization. Consequently, the unlabeled non-nucleotide probes (e.g. peptide nucleic acid oligomers) can be individually prepared, characterized and quantitated before preparing a mixture of probes for a blocking application. Hence, the mixture of probes itself can therefore be more carefully controlled, characterized and reproduced than are the Cot1 DNA probes of the prior art. Since one possible application for such a the mixture of probes is their possible use in a diagnostic assay, the ability to more easily characterize and reproduce, in a cost effective manner, the exact composition of the mixture from one batch to the next is potentially advantageous.

Applications for the Present Invention:

The suppression methods described herein can be useful in analyzing cells for the occurrence of chromosomes, chromosome fragments, genes, or chromosome aberrations (e.g. translocations, deletions, amplifications) associated with a condition or disease. Any method that can detect, identify and/or quantify selected target genomic nucleic acid in metaphase spreads, interphase nuclei, tissue sections, and extracted DNA from these cells can potentially take advantage of the present method as a substitute for the conventional Cot-1 DNA blocking. These methods include, but are not limited to, CISH (chromogen in situ hybridization), FISH, multi-color FISH, Fiber-FISH, CGH, chromosome paints and the analysis of BAC clones and arrays.

TABLE 1

| Nucleobase Sequence | Seq. Id. No. |
|---|---|
| GGCGGGCGGAGGCCGGGCGCGGTGGCTCA CGCCTGTAATCCCAGCACTTTGGGAGGCC GAGGCGGGCGGATCACCTGAGGTCAGGAG TTCGAGACCAGCCTGGCCAACATGGTGAA ACCCCGTCTCTACTAAAAATACAAAAATT AGCCGGGCGTGGTGGCGCGCGCCTGTART CCCAGCTACTCGGGAGGCTGAGGCAGGAG AATCGCTTGAACCCGGGAGGCGGAGGTTG CAGTGAGCCGAGATCGCGCCACTGCACTC CAGCCTGGGCRACAAGAGCGARACTCCGT CTCAAAAAAAA | 1 |

TABLE 1-continued

| Nucleobase Sequence | Seq. Id. No. |
|---|---|
| TTTTTTTTGAGACGGAGTYTCGCTCTTGT YGCCCAGGCTGGAGTGCAGTGGCGCGATC TCGGCTCACTGCAACCTCCGCCTCCCGGG TTCAAGCGATTCTCCTGCCTCAGCCTCCC GAGTAGCTGGGAYTACAGGCGCGCGCCAC CACGCCCGGCTAATTTTTGTATTTTTAGT AGAGACGGGGTTTCACCATGTTGGCCAGG CTGGTCTCGAACTCCTGACCTCAGGTGAT CCGCCCGCCTCGGCCTCCCAAAGTGCTGG GATTACAGGCGTGAGCCACCGCGCCCGGC CTCCGCCCGCC | 2 |
| GGCCGGGCGCGGTGGCT | 3 |
| GCTGGGATTACAGGCGTG | 4 |
| GGGAGGCCGAGGCGGG | 5 |
| GCCAGGCTGGTCTCGAACTCC | 6 |
| GAAACCCCGTCTCTACTAAAA | 7 |
| GCCGGGCGTGGTGGCG | 8 |
| TAGCTGGGATTACAGGCG | 9 |
| GGGAGGCTGAGGCAGGA | 10 |
| CCTCCCGGGTTCAAGCGATTC | 11 |
| TTGCAGTGAGCCGAGAT | 12 |
| TGCACTCCAGCCTGGGCGACA | 13 |
| **TT(k)TTTTT(k)TTTLysOLysOTTT(k)TTTTT(k)TT | |
| AGCCACCGCGCCCGGCC | 15 |
| CACGCCTGTAATCCCAGC | 16 |
| CCCGCCTCGGCCTCCC | 17 |
| GGAGTTCGAGACCAGCCTGGC | 18 |
| TTTTAGTAGAGACGGGGTTTC | 19 |
| CGCCACCACGCCCGGC | 20 |
| CGCCTGTAATCCCAGCTA | 21 |
| TCCTGCCTCAGCCTCCC | 22 |
| GAATCGCTTGAACCCGGGAGG | 23 |
| ATCTCGGCTCACTGCAA | 24 |
| TGTCGCCCAGGCTGGAGTGCA | 25 |
| AA(k)AAAAA(k)AAA-Lys-O-Lys-O-AAA(k)AAAAA(k)AA | |

Note:
k = D-lysine;
Lys = L-lysine;
O = 8-amino-3,6-dioxaoctanoic acid;

II. Embodiments of the Invention

Generally, this invention pertains to methods, kits, non-nucleotide probes as well as other compositions for the suppression of binding of detectable nucleic acid probes to undesired nucleotide sequences of genomic nucleic acid in assays designed to determine target genomic nucleic acid. In many cases, the most problematic undesired nucleotide sequences are those known in the art as randomly distributed repeat sequences, which include, but are not limited to, Alu-repeats, Kpn-repeats, di-nucleotide repeats, tri-nucleotide repeats, tetra-nucleotide repeats, penta-nucleotide repeats, hexa-nucleotide repeats, SINEs and LINEs. These are referred to as randomly distributed repeat sequences since they are not prevalent in any particular section of the genetic material, such as in a centromere or telomere region, but rather are randomly distributed within all of the chromosomes of an organism.

Non-Nucleotide Probes:

In one embodiment, this invention pertains to a non-nucleotide probe of at least sixteen nucleobase containing subunits in length having an aggregate nucleobase sequence that is at least eighty percent homologous to a sixteen nucleotide segment of randomly distributed repeat sequence of genomic nucleic acid. The segment of randomly distributed repeat sequence can be a SINE or LINE. SINEs and LINEs can be selected from the group consisting of: Alu-repeats, Kpn-repeats, di-nucleotide repeats, tri-nucleotide repeats, tetra-nucleotide repeats, penta-nucleotide repeats and hexa-nucleotide repeats.

The nucleobase sequence of the non-nucleotide probe can be chosen to be substantially, or completely, homologous to a fraction, or part, of either: (i) a known unit repeat of a Alu-repeat sequence; or (ii) a consensus sequence of a unit repeat of a known Alu-repeat sequence. For example, the segment can contain at least ten consecutive nucleobases that are at least eighty percent homologous to the unit repeat consensus Alu-repeat sequences selected from the group consisting of: Seq. Id. No. 1 and Seq. Id. No. 2 (See Table 1). The ten consecutive nucleobases can be at least ninety percent homologous to the identified Alu-repeat consensus sequences or they can be exactly homologous to the identified Alu-repeat consensus sequences. The non-nucleotide probe can be from about 16 to about 50 nucleobase containing subunits in length. The non-nucleotide probe can be a peptide nucleic acid oligomer.

In another embodiment, this invention pertains to a non-nucleotide probe containing an aggregate nucleobase sequence of at least ten consecutive nucleobases that is at least eighty percent homologous to the sequences selected from the group consisting of: Seq. Id. No. 3, Seq. Id. No. 4, Seq. Id. No. 5, Seq. Id. No. 6, Seq. Id. No. 7, Seq. Id. No. 8, Seq. Id. No. 9, Seq. Id. No. 10, Seq. Id. No. 11, Seq. Id. No. 12, Seq. Id. No. 13, Seq. Id. No. 14, Seq. Id. No. 15, Seq. Id. No. 16, Seq. Id. No. 17, Seq. Id. No. 18, Seq. Id. No. 19, Seq. Id. No. 20, Seq. Id. No. 21, Seq. Id. No. 22, Seq. Id. No. 23, Seq. Id. No. 24, Seq. Id. No. 25 and Seq. Id. No. 26. Certain of these particular sequences have been determined to be highly effective at suppressing the binding of a detectable nucleic acid probe to undesired chromosomes in an assay for detecting the HER-2 or MLL target nucleic acid sequences in genomic nucleic acid (See: Examples 4 and 5). Complementary sequences to the tested nucleobase sequences are included because these non-nucleotide probes are directed to genomic nucleic acid that is typically present in double stranded form. Hence, the target sequences for these probe sequences, as well as their complements, can be present in samples containing the complementary strands of genomic nucleic acid.

The ten consecutive nucleobases can be either: (i) at least ninety percent homologous to the identified sequences; or (ii) exactly homologous to the identified sequences. The probe can be identical in nucleobase sequence to any one of the identified sequences. The non-nucleotide probe can be from about 10 to about 50 nucleobase containing subunits in length. The non-nucleotide probe can be a peptide nucleic acid oligomer.

The aforementioned non-nucleotide probes will either be labeled or unlabeled. The exact configuration of the probe will usually depend upon its intended use. For example, if the probe is being screened in order to determine whether or not it may be useful in binding to undesired sequence in genomic nucleic acid, as described in more detail below, it is likely to be labeled. Conversely, if the probe is being used in a method to suppress the binding of detectable nucleic acid probe to undesired sequence in genomic nucleic acid, as described in more detail below, it is likely to be unlabeled.

Probe Mixtures:

In still another embodiment, this invention pertains to a mixture of two or more non-nucleotide probes wherein each probe contains an aggregate nucleobase sequence that is at least eighty percent homologous to a sixteen nucleotide segment of randomly distributed repeat sequence of genomic nucleic acid. The mixture can comprise from about 5 to about 50 probes of different nucleobase sequence. The mixture can comprise from about 10 to about 25 probes of different nucleobase sequence. The individual probes of the mixture can comprise from about 10 to about 50 nucleobase containing subunits in length.

Any of the aforementioned non-nucleotide probes can be suitable for use in the non-nucleotide probe mixture. The non-nucleotide probes can be peptide nucleic acid oligomers. The mixture of probes can further comprise one or more detectable nucleic acid probes. The mixture of probes can further comprise genomic nucleic acid of a sample to be tested.

Probes & Probe Mixtures:

The non-nucleotide probes or mixture of non-nucleotide probes of this invention can be manufacture and purified using conventional methods, including without limitation, those previously described herein. They may be provided, used, handled and/or dispensed either as a dry (lyophilized) powder, dissolved or suspended in a solvent or mixed with a dry carrier. Mixtures of non-nucleotide probes can be, but are not necessarily, produced by first manufacturing and purifying the component probes followed by a step of mixing the probes in the desired ratio to thereby produce the mixture. Suitable solvents and carriers for the non-nucleotide probes are known in the art and include, without limitation, solutions of water that optionally comprise an organic modifier, such as N,N'-dimethylformamide (DMF) or 1-Methyl-2-pyrrolidone (NMP), and/or buffer.

Hybrid Compositions:

In yet another embodiment, this invention pertains to a composition comprising genomic nucleic acid containing one or more segments of randomly distributed repeat sequence selected from the group consisting of: SINEs and LINEs. The SINEs and LINEs can be selected from the group consisting of: Alu-repeats, Kpn-repeats, di-nucleotide repeats, tri-nucleotide repeats, tetra-nucleotide repeats, penta-nucleotide repeats and hexa-nucleotide repeats. The one or more segments of randomly distributed repeat sequence can be a fraction, or part, of a unit repeat of either: i) an Alu-repeat sequence; or ii) a consensus sequence of a Alu-repeat sequence. The composition further comprises two or more non-nucleotide probes of different nucleobase sequence hybridized to at least a fraction, or part, of the one or more segments of randomly distributed repeat sequence of the genomic nucleic acid. Hence, the composition is the hybrid of the segment of randomly distributed repeat sequence and the two or more non-nucleotide probes. The non-nucleotide probes can suppress the binding of detectable nucleic acid probe to the randomly distributed repeat sequence of the genomic nucleic acid.

Any of the aforementioned non-nucleotide probes, including preferred embodiments thereof, are suitable for use in producing the hybrid. The non-nucleotide probes can be peptide nucleic acid oligomers.

The genomic nucleic acid of the hybrid can comprise complementary strands of randomly distributed repeat sequence. The genomic nucleic acid can be contained within a fixed tissue or a cell. The genomic nucleic acid can be contained within metaphase spreads, interphase nuclei or the nuclei of paraffin embedded tissue material or frozen tissue sections. The nucleic acid can also be extracted from any of the aforementioned samples.

An illustration of an exemplary construct of this hybrid is found in FIG. 1. The design of the aforementioned construct is intended to allow the non-nucleotide probes to hybridize to the complementary strands of genomic nucleic acid in such a manner as to cover as much as possible of one or the other of the complementary strands of the genomic nucleic acid. This approach can also serve to keep the strands separated. The ability to lock the complementary strands of nucleic acid into an open conformation under hybridization conditions is surprising in view of the teachings of Perry-O'Keefe et al. (Proc. Natl. Acad. Sci. USA, 93: 14670-14675 (1996)) who specifically teach that DNA reannealing will expel bound PNA probe that is much shorter. Because the PNA oligomers are short, as compared with the complementary strands of genomic nucleic acid, the PNA oligomers are expected to be expelled and thereby should not act to block the hybridization of the longer detectable nucleic acid probes to these undesired sequences.

Because it may be desirable to provide a mixture of non-nucleotide probes in the same container as the detectable nucleic acid probes, and because the detectable nucleic acid probes can possess segments of sequence that are derived from the randomly distributed repeat sequences, this invention is still further directed to a composition comprising a detectable nucleic acid probe of at least 100 bp that has been derived from genomic nucleic acid and that contains one or more segments of randomly distributed repeat sequence selected from the group consisting of: SINEs and LINEs. The SINEs and LINEs can be selected from the group consisting of: Alu-repeats, Kpn-repeats, di-nucleotide repeats, tri-nucleotide repeats, tetra-nucleotide repeats, penta-nucleotide repeats and hexa nucleotide repeats. The composition further comprises two or more non-nucleotide probes of different nucleobase sequence hybridized to at least a fraction of the one or more segments of randomly distributed repeat sequence of the detectable nucleic acid probe. Hence, the composition is the hybrid of the detectable nucleic acid probe hybridized to the two or more non-nucleotide probes.

Any of the aforementioned non-nucleotide probes can be suitable for producing the hybrid. The non-nucleotide probes can be peptide nucleic acid oligomers.

Method for the Suppression of Undesired Detectable Probe Binding:

In still another embodiment, this invention is directed to a method for suppressing the binding of one or more detectable nucleic acid probes, that are greater than 100 bp and that have been derived from genomic nucleic acid, to one or more undesired sequences in an assay for determining target genomic nucleic acid of a sample. The method comprises contacting the sample with a mixture of two or more non-nucleotide probes wherein each probe contains an aggregate nucleobase sequence that is at least eighty percent homologous to a segment of randomly distributed repeat sequence of genomic nucleic acid. According to the method, the sample is also contacted with the one or more detectable nucleic acid probes. The target genomic nucleic acid of the sample can then be determined by determining the hybridization of the one or more detectable nucleic acid probes to the target genomic nucleic acid of the sample wherein the presence, absence or amount of hybridization of the detectable nucleic acid probe to the target genomic nucleic acid can be representative of the presence, absence or amount of target genomic nucleic acid in the sample.

The randomly distributed repeat sequences can be selected from the group consisting of: SINEs and LINES. The SINEs and LINEs can be selected from the group consisting of; Alu-repeats, Kpn-repeats, di-nucleotide repeats, tri-nucleotide repeats, tetra-nucleotide repeats, penta-nucleotide repeats and hexa-nucleotide repeats. The nucleobase sequence of SINEs and LINEs can be used as the basis for producing probes that are suitable to suppress undesired binding since Applicants have shown that blocking of the Alu-repeat sequences are particularly useful in lowering the background signal that is otherwise present in such assays (See: Example 4).

According to the method, the nucleobase sequence of the non-nucleotide probe can be selected to be at least eighty percent homologous to a part of a consensus sequence of a randomly distributed repeat sequence. The nucleobase sequence of the non-nucleotide probe can contain a segment of at least ten consecutive nucleobases that is at least eighty percent homologous to a fraction, or part, of the consensus unit repeat Alu-repeat sequences selected from the group consisting of: Seq. Id. No. 1 and Seq. Id. No. 2. The ten consecutive nucleobases can be at least ninety percent homologous to the identified consensus sequences. The ten consecutive nucleobases can be exactly homologous to the identified consensus sequences.

Any of the aforementioned non-nucleotide probes can be suitable for use in producing the hybrid that suppresses the binding of the detectable nucleic acid probes to the undesired sequence. The two or more non-nucleotide probes can be about 10 to about 50 nucleobase containing subunits in length. The non-nucleotide probes can be peptide nucleic acid oligomers.

According to the method, the genomic nucleic acid can comprise complementary strands of randomly distributed repeat sequence. The genomic nucleic acid can be contained in a fixed tissue or a cell. The genomic nucleic acid can be contained in metaphase spreads, interphase nuclei or the nuclei of paraffin embedded tissue material or frozen tissue sections. The nucleic acid can also be extracted from the cells or tissues.

Genomic Arrays:

(i) Array Comparative Genomic Hybridization (Array CGH)

Chromosomal comparative genomic hybridization (CGH) allows a comprehensive analysis of multiple DNA gains and losses in entire genomes within a single experiment. Genomic DNA from the tissue to be investigated, such as fresh or paraffin-embedded tumor tissue and normal reference DNA, are differentially labeled and simultaneously hybridized in situ to normal metaphase chromosomes. Array-based Comparative Genomic Hybridization (array CGH) provides a higher-resolution and more quantitative alternative to chromosome CGH for the assessment of genomic copy number abnormalities. Instead of hybridizing to individual chromosomes (as occurs in a ISH or FISH assay) with array CGH copy number abnormalities are mapped onto arrays of cloned DNA sequences such as P1s, BACs or cDNAs with the fluorescence ratios at the arrayed DNA elements providing a locus-by-locus measure of DNA copy-number variation. The basic assumption of a CGH experiment is that the ratio of the binding of test and control DNA is proportional to the ratio of the concentrations of sequences in the two samples.

(ii) Methodology of CGH

For CGH or array CGH, whole-genomic DNA is isolated from a tumor by standard extraction protocols. Control or reference DNA is isolated from an individual who has either a normal 46, XX karyotype or a normal 46, XY karyotype. There is also a sample that is to be analyzed by comparison to the control or reference DNA. The control and sample DNA that has been extracted from the two genomes is differentially labeled (for example fluorescein conjugated to dUTP for the tumor genome and Cy3 conjugated to dUTP for the normal genome). The sample and control DNA samples are combined, and an excess of unlabelled blocking reagent (e.g. a mixture of non-nucleic acid probes as described herein) is added into the hybridization mixture, to suppress the repetitive sequences that are present in both genomes. The blocking reagent is useful because hybridization of the repetitive DNA would impair the evaluation of the unique sequences that are either over represented or underrepresented in the sample genome. This probe mixture is hybridized to normal human reference metaphase chromosomes or arrays of cloned DNA sequences in the case of array CGH. The relative color intensities of the two fluorochromes reflect DNA copy-number alterations in the tumor genome. In this way it is possible to determine whether or not the sample DNA is normal (where the color intensities of the two fluorophores is the same) or abnormal (where the color intensities of the two samples differs). The degree of difference in the color intensities for the two fluorophores can also a measure of the severity or identity of a disease state.

(iii) Array Based Embodiments of the Invention

Thus, in yet another embodiment, this invention pertains to comparing a sample of genomic nucleic acid with that of a control sample using a genomic nucleic acid reference array. The method comprises providing a sample of genomic nucleic acid to be tested, providing a control of genomic nucleic acid, wherein the control and the sample are differentially labeled. The method further comprises providing a genomic nucleic acid reference array, and providing a mixture of two or more non-nucleotide probes wherein each probe contains an aggregate nucleobase sequence that is at least eighty percent homologous to a sixteen nucleotide segment of randomly distributed repeat sequence of genomic nucleic acid. The method further comprises treating the sample and control genomic nucleic acid, the array or both the sample and control genomic nucleic acid and the array with the mixture of non-nucleotide probes under suitable hybridization conditions. The array is then contacted with the treated mixture of sample and control genomic nucleic acid under suitable hybridization conditions. The intensities of the signals from the differential labels on the array, caused by hybridization of the probes to genomic nucleic acid, are then compared to thereby determine one or more variations in copy numbers of sequences in the sample as compared with the relative copy numbers of substantially identical sequences in the control.

Method for Determining Non-Nucleotide Probes:

In still another embodiment, this invention is directed to a method for determining non-nucleotide probes that hybridize to randomly distributed repeat sequences and that are suitable for suppressing the binding of a detectable nucleic acid probe, that is greater than 100 bp in length and that is derived from genomic nucleic acid, to one or more undesirable sequences in an assay for determining target genomic nucleic acid of a sample. The method comprises designing possible nucleobase sequences of non-nucleotide probes using sequence alignment of available sequence data for randomly distributed repeat sequences and then preparing labeled non-nucleotide probes having said possible nucleobase sequences. According to the method, genomic nucleic acid of a sample that contains the target genomic nucleic acid is treated with the labeled non-nucleotide probes under suitable hybridization conditions. The relative signal of the hybridized labeled probes of the many different possible nucleobase sequences is then determined. Based upon the signal intensity data, the probe or probes that exhibit the strongest signal, as a result of binding to the genomic nucleic acid, are selected and tested to thereby determine whether or not they are suitable for suppressing the binding of a detectable nucleic acid probe of greater than 100 bp in length that is derived from genomic nucleic acid to one or more non-target sequences in an assay for determining target genomic nucleic acid of a sample. In order to test the one or more selected non-nucleotide probes, each probe can be re-synthesized in unlabeled form and then tested using the method for suppressing the binding of detectable probes to undesired sequences as described above. Once tested, the best probes can be used to produce a mixture that can be used in an assay to suppress the binding of detectable nucleic acid probes to undesired target sequence. The non-nucleotide probes can be peptide nucleic acid oligomers.

Those of skill in the art will appreciate that sequence alignment is a process that can be performed using a database of sequence information that is analyzed using a computer and software designed to analyze the database in accordance with a particular set of input parameters. In the context of the present invention, the sequence of available randomly distributed repeat sequences would be provided in the database. From this database, potential probe sequences can be selected in accordance with the output provided from the software program operating by computer analysis of the database in view of the input parameters. The input parameters can be directed toward providing a consensus sequence where there are sequence variations known to exist among the various randomly distributed repeats sequences. Whether using a known randomly distributed repeat sequence, or a consensus sequence as can be seen from the data in Example 3, one should broadly choose all possible nucleobase sequences and then screen the candidates since small variations of one or two nucleobases can substantially alter the hybridization performance of the non-nucleotide probes.

As illustrated by the Examples of this specification, this method has been shown to be very useful in selecting probes that can be effectively used to "block" or suppress the binding of detectable nucleic acid probes to undesired sequences in genomic nucleic acid. Although this method has been shown to be effective with respect to randomly distributed repeat sequences, it is anticipated that said method can be equally useful in the design of probes or probe mixtures that aid in the suppression of binding of detectable probe to other undesired sequences of genomic nucleic acid. In order to extend the aforementioned method to other problematic sequences it is only required that one identify a potentially problematic sequence or sequences from which potentially useful blocking probes can be generated for screening purposes in accordance with the aforementioned method.

Kits:

In still another embodiment, this invention is directed to a reagent kit comprising a mixture of two or more non-nucleotide probes containing at least sixteen consecutive nucleobases that are at least eighty percent homologous to a fraction of the unit repeat Alu-repeat consensus sequence selected from the group consisting of: Seq. Id. No. 1 or Seq. Id. No. 2. The kit further comprises one or more other reagents, compositions and or instructions suitable for performing an assay to thereby determine genomic nucleic acid of a sample. For example, the reagent kit can further comprise one or more detectable nucleic acid probes of greater than 100 bp in length and that are derived from genomic nucleic acid. The one or more detectable nucleic acid probes can be provided in the container that contains the mixture of two or more non-nucleotide probes.

In yet still another embodiment, this invention is directed to a kit comprising a mixture of two or more non-nucleotide probes wherein at least one probe contains a segment of at least ten consecutive nucleobases that are at least eighty percent homologous to the Alu-repeat sequences selected from the group consisting of: Seq. Id. No. 3, Seq. Id. No. 4, Seq. Id. No. 5, Seq. Id. No. 6, Seq. Id. No. 7, Seq. Id. No. 8, Seq. Id. No. 9, Seq. Id. No. 10, Seq. Id. No. 11, Seq. Id. No. 12, Seq. Id. No. 13, Seq. Id. No. 14, Seq. Id. No. 15, Seq. Id. No. 16, Seq. Id. No. 17, Seq. Id. No. 18, Seq. Id. No. 19, Seq. Id. No. 20, Seq. Id. No. 21, Seq. Id. No. 22, Seq. Id. No. 23, Seq. Id. No. 24, Seq. Id. No. 25 and Seq. Id. No. 26. The kit further comprises at least one other reagent, composition and/or set of instructions for performing a assay to thereby determine genomic nucleic acid of a sample. For example, the kit can further comprise one or more detectable nucleic acid probes of greater than 100 bp in length and that are derived from genomic nucleic acid. The one or more detectable nucleic acid probes can be provided in the container that contains the mixture of two or more non-nucleotide probes.

Said kits are particularly useful since they provide reagents suitable to perform a specific type of assay in convenient packaging thereby eliminating the need to devise an assay and then prepare the necessary reagents. The kits can provide the necessary reagents to perform an assay for detecting the HER-2 or MLL target sequence in a sample containing human genomic nucleic acid.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

This invention is now illustrated by the following examples that are not intended to be limiting in any way.

General Information on PNA Oligomer Synthesis

All PNA Oligomers were prepared from commercial reagents and instrumentation obtained from Applied Biosystems, Foster City, Calif. using manufacturer published procedures, other well-known procedures or those disclosed in U.S. Pat. Nos. 5,888,733, 5,985,563, 6,110,676, 6280, 946, 6,287,772, 6,326,479, 6,355,421, 6,361,942 and 6,441,152 (all of which are herein incorporated by reference). All PNA oligomers were purified by reversed-phase high performance liquid chromatography using well-known methods. Table 2 lists PNA oligomers used in Examples 4-5, described below.

TABLE 2

| Probe No. | Label | Position | N-term | Sequence | C-term | Seq. Id. No. |
|---|---|---|---|---|---|---|
| 1 | | # | | CAGGCCGGGTGCAGTGGC | | 35 |
| 2 | fluorescein | # | Lys (Flu) | CAGGCCGGGTGCAGTGGC | | |
| 3 | | 9-25 | | GGCCGGGCGCGGTGGCT | | 3 |
| 4 | fluorescein | 9-25 | Lys (Flu) | GGCCGGGCGCGGTGGCT | | |
| 5 | | 9-25 | EE | GGCCGGGCGCGGTGGCT | EE | |
| 6 | fluorescein | 9-25 | Flu-OEE | GGCCGGGCGCGGTGGCT | EE | |
| 7 | fluorescein | 9-25 | FluOLysLys | GGCCGGGCGCGGTGGCT | LysLys | |
| 8 | biotin | 10-24 | Bio-OEE | GCCGGGCGYGGTGGC | EE | 36 |
| 9 | | 10-24 | EE | GCCGGGCGYGGTGGC | EE | |
| 10 | fluorescein | 10-24 | Flu-OEE | GCCGGGCGYGGTGGC | EE | |
| 11 | | 26-43 | | GCTGGGATTACAGGCGTG | | 4 |
| 12 | fluorescein | 26-43 | Lys (Flu) | GCTGGGATTACAGGCGTG | | |
| 13 | | 26-43 | Lys-Lys | GCTGGGATTACAGGCGTG | Lys-Lys | |
| 14 | | 26-43 | EE | GCTGGGATTACAGGCGTG | EE | |
| 15 | fluorescein | 26-43 | Flu-OEE | GCTGGGATTACAGGCGTG | EE | |
| 16 | biotin | 28-43 | Bio-OEE | GCTGGGAYTACAGGCG | EE | 37 |
| 17 | | 32-48 | | TGTAATCCCAGCACTTT | | 38 |
| 18 | fluorescein | 32-48 | Lys (Flu) | TGTAATCCCAGCACTTT | | |
| 19 | fluorescein | 42-56 | Lys (Flu)-Lys (Flu) | GCACTTTGGGAGGCC | | 39 |
| 20 | fluorescein | 42-56 | Lys (Flu)-Lys (Flu) | GGCCTCCCAAAGTGC | | 40 |
| 21 | biotin | 49-54 | Bio-OEE | CCTCCC-EOE-CCCTCC | EE | |
| 22 | biotin | 49-63 | Bio-OEE | GGGAGGCYGAGGCGG | EE | 42 |
| 23 | | 49-64 | | GGGAGGCCGAGGCGGG | | 5 |
| 24 | fluorescein | 49-64 | Flu-O | GGGAGGCCGAGGCGGG | | |
| 25 | fluorescein | 49-64 | FluOLysLys | GGGAGGCCGAGGCGGG | LysLys | |
| 26 | | 49-64 | EE | GGGAGGCCGAGGCGGG | EE | |
| 27 | fluorescein | 49-64 | Flu-OEE | GGGAGGCCGAGGCGGG | EE | |
| 28 | | # | | ACTTTGGGAGGAAGATCACC | | 43 |
| 29 | fluorescein | # | Flu-Lys | ACTTTGGGAGGAAGATCACC | | |
| 30 | | 70-84 | | CACCTGAGGTCAGGA | | 44 |
| 31 | fluorescein | 70-84 | Flu-OE | CACCTGAGGTCAGGA | E | |

TABLE 2-continued

| Probe No. | Label | Position | N-term | Sequence | C-term | Seq. Id. No. |
|---|---|---|---|---|---|---|
| 32 | | 82-102 | | GCCAGGATGGTCTCGATCTCC | | 27 |
| 33 | fluorescein | 82-102 | Lys (Flu) | GCCAGGATGGTCTCGATCTCC | | |
| 34 | | 82-102 | | GCCAGGCTGGTCTCGAACTCC | | 6 |
| 35 | fluorescein | 82-102 | Lys (Flu) | GCCAGGCTGGTCTCGAACTCC | | |
| 36 | | 82-102 | Lys-Lys | GCCAGGCTGGTCTCGAACTCC | Lys-Lys | |
| 37 | | 82-102 | EE | GCCAGGCTGGTCTCGAACTCC | EE | |
| 38 | fluorescein | 82-102 | Flu-OEE | GCCAGGCTGGTCTCGAACTCC | EE | |
| 39 | | 98-113 | | TGGCCAACATGGTGA | | 45 |
| 40 | fluorescein | 98-113 | Flu-OE | TGGCCAACATGGTGA | E | |
| 41 | | 112-132 | | GAAACCCGTCTCTACTAAAA | | 7 |
| 42 | fluorescein | 112-132 | Lys (Flu) | GAAACCCGTCTCTACTAAAA | | |
| 43 | | 112-132 | Lys | GAAACCCGTCTCTACTAAAA | Lys | |
| 44 | | 112-132 | Lys-Lys | GAAACCCGTCTCTACTAAAA | Lys-Lys | |
| 45 | | 112-132 | EE | GAAACCCGTCTCTACTAAAA | EE | |
| 46 | fluorescein | 112-132 | Flu-OEE | GAAACCCGTCTCTACTAAAA | EE | |
| 47 | | 145-160 | | GCCGGGCGTGGTGGCG | | 8 |
| 48 | fluorescein | 145-160 | Lys (Flu) | GCCGGGCGTGGTGGCG | | |
| 49 | | 145-160 | EE | GCCGGGCGTGGTGGCG | EE | |
| 50 | fluorescein | 145-160 | Flu-OEE | GCCGGGCGTGGTGGCG | EE | |
| 51 | fluorescein | 145-160 | FluOLysLys | GCCGGGCGTGGTGGCG | LysLys | |
| 52 | | 163-180 | | TAGCTGGGATTACAGGCG | Lys | 9 |
| 53 | fluorescein | 163-180 | Lys (Flu) | TAGCTGGGATTACAGGCG | Lys | |
| 54 | | 163-180 | Lys-Lys | TAGCTGGGATTACAGGCG | Lys-Lys | |
| 55 | | 163-180 | EE | TAGCTGGGATTACAGGCG | EE | |
| 56 | fluorescein | 163-180 | Flu-OEE | TAGCTGGGATTACAGGCG | EE | |
| 57 | | 184-200 | | GGGAGGCTGAGGCAGGA | Lys | 10 |
| 58 | fluorescein | 184-200 | Lys (Flu) | GGGAGGCTGAGGCAGGA | Lys | |
| 59 | | 184-200 | Lys-Lys | GGGAGGCTGAGGCAGGA | Lys-Lys | |
| 60 | | 184-200 | EE | GGGAGGCTGAGGCAGGA | EE | |
| 61 | fluorescein | 184-200 | Flu-OEE | GGGAGGCTGAGGCAGGA | EE | |
| 62 | | 186-200 | | GAGGCTGAGGCAGGA | | 46 |
| 63 | fluorescein | 186-200 | Lys (Flu) | GAGGCTGAGGCAGGA | | |

TABLE 2-continued

| Probe No. | Label | Position | N-term | Sequence | C-term | Seq. Id. No. |
|---|---|---|---|---|---|---|
| 64 | | 201-221 | | CCTCCCGGGTTCACGCCATTC | | 47 |
| 65 | fluorescein | 201-221 | Lys (Flu) | CCTCCCGGGTTCACGCCATTC | | |
| 66 | | 201-221 | | CCTCCCGGGTTCAAGCGATTC | Lys | 11 |
| 67 | fluorescein | 201-221 | Lys (Flu) | CCTCCCGGGTTCAAGCGATTC | Lys | |
| 68 | | 201-221 | EE | CCTCCCGGGTTCAAGCGATTC | EE | |
| 69 | fluorescein | 201-221 | Flu-OEE | CCTCCCGGGTTCAAGCGATTC | EE | |
| 70 | fluorescein | 201-221 | FluOLysLys | CCTCCCGGGTTCAAGCGATTC | LysLys | |
| 71 | | 228-244 | Lys | TTGCAGTGAGCCGAGAT | | 12 |
| 72 | fluorescein | 228-244 | Lys (Flu) | TTGCAGTGAGCCGAGAT | | |
| 73 | fluorescein | 228-244 | FluOLysLys | TTGCAGTGAGCCGAGAT | LysLys | |
| 74 | | 228-244 | EE | TTGCAGTGAGCCGAGAT | EE | |
| 75 | fluorescein | 228-244 | Flu-OEE | TTGCAGTGAGCCGAGAT | EE | |
| 76 | fluorescein | 228-244 | Flu-OPP | TTGCAGTGAGCCGAGAT | PP | |
| 77 | fluorescein | 228-244 | Flu-OOO | TTGCAGTGAGCCGAGAT | OO | |
| 78 | fluorescein | 228-244 | Flu-OGluGlu | TTGCAGTGAGCCGAGAT | GluGlu | |
| 79 | fluorescein | 228-244 | Lys (Flu) | DUCUCGGCUCDCUGCDD | Lys | 48 |
| 80 | fluorescein | 228-244 | Lys (Flu) | UUGCDGUGDGCCGDGDU | Lys | 49 |
| 81 | | 249-273 | | CCACTGCACTCCAGCCTGGGCGACA | | 50 |
| 82 | fluorescein | 249-273 | Lys (Flu) | CCACTGCACTCCAGCCTGGGCGACA | | |
| 83 | | 253-269 | Lys | TGCACTCCAGCCTGGGC | | 51 |
| 84 | fluorescein | 253-269 | Lys (Flu) | TGCACTCCAGCCTGGGC | | |
| 85 | | 253-273 | | TGCACTCCAGCCTGGGCGACA | | 13 |
| 86 | fluorescein | 253-273 | Lys (Flu) | TGCACTCCAGCCTGGGCGACA | | |
| 87 | | 253-273 | Lys-Lys | TGCACTCCAGCCTGGGCGACA | Lys-Lys | |
| 88 | | 253-273 | EE | TGCACTCCAGCCTGGGCGACA | EE | |
| 89 | fluorescein | 253-273 | Flu-OEE | TGCACTCCAGCCTGGGCGACA | EE | |
| 90 | | # | | TTTGAGACAGAGTCTCGC | | 52 |
| 91 | fluorescein | # | Lys (Flu) | TTTGAGACAGAGTCTCGC | | |
| 92 | | 275-294 | | TTTGAGACGGAGTCTCGCTC | Lys | 53 |

TABLE 2-continued

| Probe No. | Label | Position | N-term | Sequence | C-term | Seq. Id. No. |
|---|---|---|---|---|---|---|
| 93 | fluorescein | 275-294 | Lys (Flu) | TTTGAGACGGAGTCTCGCTC | Lys | |
| 94 | fluorescein | 292-298 | FluLys (Flu)OO | TTTTTTT-O-Lys-O-Lys-O-TTTTTTT | Lys | |
| 95 | | 292-298 | FluLysOO | TTkTTTTT-O-Lys-O-Lys-O-TTkTTTTT | Lys | |
| 96 | fluorescein | 292-298 | FluLys (Flu)OO | TTkTTTTT-O-Lys-O-Lys-O-TTkTTTTT | Lys | |
| 97 | | PolyA tail | Lys | TTkTTTTTkTTTLysOLysOTT TkTTTTTkTT | Lys | |
| 98 | fluorescein | PolyA tail | FluOLys | TTkTTTTTkTTTLysOLysOTT TkTTTTTkTT | Lys | |
| 99 | fluorescein | PolyA tail | FluO | TTkTTTTTkTTTOOOTTTkTTT TTkTT | | | fluorescein or Flu = 5(6)-carboxyfluorescein;
Lys = the amino acid L-lysine,
k = the amino acid D-lysine;
0 8-amino-3,6-dioxaoctanoic acid;
E = the modification resulting from use of compound 4 as described in Gildea et al., *Tett. Lett.* 39: 7255-7258 (1998)),
Bio = biotin;
Glu = the amino acid glutamic acid;
d = the product of using piperazine-N,N' diacetic acid-mono (2-Boc-aminoethylamide) as a monomer;
: alu sequence, but not consensus sequence;
*: score not comparable to directly labeled oligomers General Information on Nucleic Acid Oligomers Those of skill in the art will appreciate that detectable nuclei acid probes can be produced by selection of a clone covering the desired region of interest from a public library of clones (e.g. Resourcezemtrum in Deutchen Humangenomprojekt, RZPD). The DNA from such a clone can then be cultured within a host organism, extracted from the host, purified, and labeled. To amplify a specific DNA sequence by cloning, the DNA can be inserted into a vector and both insert and vector were amplified inside appropriate host cells. The amplified DNA can then be extracted. Commonly used vectors include bacterial plasmids, cosmids, PACs, BACs, and YACs, all of which are well known to one or ordinary skill in the art.

The purified DNA is then labeled by the Nick translation. The Nick translation reaction employs two enzymes, Dnase I which produces the "nicks" in the double-stranded DNA and DNA polymerase, which incorporate labeled nucleotides along both strands of the DNA duplex. It will be appreciated that using no more that routine experimentation and information known to those of ordinary skill in the art that any known labeling method can be used for labeling the nucleic acid probes used in the embodiments and/or description of this invention.

In Examples 4 and 5, fluorescence labeled COS or PAC based DNA probes were produced by culturing the COS or PAC containing *E. coli* and harvesting the human DNA from the cultures. The COS or PAC DNA was purified using Qiagen large construct kit (Qiagen, Kebolab A/S, Copenhagen, Denmark). The clones were checked by restriction enzyme digestion. From each of the clones, the DNA was labeled by conventional Nick translation using a monomer labeled with either fluorescein, Cy3, or Rhodamine, as appropriate. The Nick translation was performed using well known methods.

General Information on Preferred Method for Cytogenetic Preparations:

Metaphase spreads and interphase nuclei were prepared from human peripheral blood lymphocytes. A blood sample of 0.5 mL was added to 10 mL culture medium (RPMI 1640 medium supplemented with 20% fetal calf serum, 2 mM Glutamine, 100 U/mL Penicillin/Streptomycin, 1% Phytohemagglutine, and 50 U/mL Heparin) and cultured for 72 hours at 37° C. For metaphase arrest the culture was incubated with 0.1 µg/mL Colcemid (Gibco, BRL) for 90 min at 37° C. The culture was then centrifuged at 500×g for 10 min. The supernatant was removed leaving 1 mL for resuspension in 8 mL 60 mM KCl. After incubation for 30 min at room temperature (RT), the cells were pre-fixated by adding 1 mL freshly made Fixative (3+1 v/v methanol/acetic acid) on top of the hypotonic suspension, and mixed carefully by turning the tube. After 10 min at RT, the suspension was pelleted by centrifugation at 500×g for 10 min. The supernatant was then removed leaving 1 mL that was resuspended in 10 mL Fixative added slowly with gentle agitation. The fixation was repeated twice with at 10 min incubation at RT between each fixation. After the third fixation the cells were resuspended in 1 mL Fixative. The cells were then dropped onto wet microscopic slides that have been cleaned in detergent and rinsed with water. The slides are left to air dry and stored at −20° C. until hybridization.

Example 1: Design of Non-Nucleotide Probes Directed Towards Repetitive Sequences For this Example, the nucleobase sequences of non-target hybridization probes directed toward Alu repeat consensus sequence were designed. It was envisioned that the probe sequences that would be best for suppressing the binding of detectable nucleic acid probes, generated from nick translation of cosmid nucleic acid, would be those nucleobase sequences possessing shared repeated sequences of Alu repeat sequence that are most prevalent in genomic nucleic acid. Hence, a consensus sequence of known Alu-repeat sequences was generated by performing an alignment analysis of five Alu consensus sequences representing the two family branches J and S (GenBank Acc. No. U14567 and U14571-14574) (Claverie, J-M and Makalowski, W. Science, 371; 752 (1994)), using the Clustal W algorithm. The three identified subfamilies of the Y family branch have not been included in the alignment shown in FIG. 2 as the relative frequency of Alu elements belonging to the Y family is very low (presumably less than 0.5% Sherry et al., Genetics, 147: 1977-1982 (1997). The consensus sequence, and its complement, that were determined using this approach are Seq. ID. No. 1 and Seq. Id No. 2. The raw alignment data output for Seq. ID No. 1 is also presented in FIG. 2.

From the consensus sequence data, the nucleobase sequence of numerous potential probes was determined. Generally however, the nucleobase sequence design of the various probes was selected to, as completely as possible when the probes were mixed together, blanket the upper and lower strand of the Alu consensus sequence, as illustrated in FIG. 1, in order to disrupt as much as possible the hybridization between the individual strands of the repeated (Alu) sequences of the genomic nucleic acid of a sample. Because disruption occurs if probe is bound to one strand, the position for hybridization of the various probes, when mixed together, was chosen such that the probes hybridizing to one of the two strands were substantially offset as compared with the probes hybridizing to the other strand. In this way the entire hybrid sequence was blanketed with as few probes as possible. This approach was taken to minimize the number of probes need; it however is not a limitation since additional probes or more extensive blanketing of the randomly distributed repeat sequence is acceptable. Moreover, it was believed that it was preferable to blanket at least fifty percent, and more preferably at least two thirds, of the linear double stranded molecule to thereby prevent the rehybridization of the two strands of genomic nucleic acid. Additionally, the probe candidates were checked for probe self dimers, probe pair dimers, and probe hairpins to minimize the hybridization reactivity with the probes themselves (i.e. intramolecular interactions) and with other probes in the mixture (e.g. intermolecular interactions).

Using these design parameters, the nucleobase sequences were chosen for the numerous probes that might, when mixed together, suppress the binding of detectable nucleic acid probes to undesired target genomic nucleic acid. These sequences were used to prepare non-nucleotide (i.e. PNA oligomer) probes for further testing and analysis.

Example 2: Evaluation of PNA Oligomer Candidates

Preferred Procedure for Performing In-Situ Hybridization Using Directly Labeled PNAs:

Slides for in-situ hybridization using directly labeled PNAs were prepared as described in the general information on preferred method for cytogenetic preparations as discussed above. For pre-treatment, the slide containing metaphase spreads and interphase nuclei was immersed shortly in TBS (Tris-buffered saline), followed by 3.7% formaldehyde in TBS for 2 min at RT, and twice in TBS for 5 min each. The slide was treated with Proteinase K (DAKO S3020, DAKO A/S, Glostrup, Denmark) diluted 1:2,000 in TBS for 10 min at RT, and rinsed twice in TBS for 5 min each, followed by dehydration in a cold ethanol series (70%, 85%, and 96%), 2 min each. The slide was then air-dried. For hybridization with the fluorescein labeled PNA probes, 10 µL hybridization buffer (70% formamide, 20 mM Tris pH 7.5, 10 mM NaCl, 10 mM phosphate buffer pH 7.5, 0.02% Ficoll, 0.02% polyvinylpyrrolidon, and 0.02% BSA (bovine serum albumin)) with 50 nM PNA probe was added to the pre-treated slide. An 18-mm$^2$ coverslip was applied to cover the hybridization mixture. The slide was denatured by incubation at 80° C. for 5 min and allowed to hybridize by incubation at RT for 30 min. The coverslip was removed in PBS (Phosphate-buffered saline) at RT. Excess of probe was removed by washing in preheated PBS with 1% Tween 20 at 60° C. for 25 min. Finally the slide was dehydrated in a cool ethanol series and air-dried at describe above. The slide was mounted in 10 µL anti-fade mounting medium (Vectashield H-1000, Vector Laboratories, Inc. Burlingame) supplemented with 0.1 µg/mL 4,6-diamoni-2phenyl-indole (DAPI, Sigma Chemicals) and sealed with a coverslip. Slides were then analyzed using a microscope equipped with a CCD digital camera.

Digital Imaging Microscopy:

Images reproduced in FIGS. 3-7 were obtained using a Leica fluorescent microscope equipped with a 100× immersion oil objective, a 10× ocular (total enlargement is 1,000 fold) and fluorescent filter cubes obtained either from Leica or Chroma (Chroma Technology Corp., Brattleboro, Vt., US). Electronic digital images were made of the slide using a Photometric Sensys CCD-camera and Leica QFISH software (Leica Imaging System Ltd, Cambridge, UK).

Experimental Design:

It is well established that the hybridization of labeled nucleic acid, containing Alu sequences, to metaphase spreads will produce a distinct and highly reproducible R-banding pattern (Kornberg and Rykowski, 1988; Baldini and Ward, 1991). These isolated nucleic acid fragments are typically greater than 100 bp in length. Thus, it seemed reasonable to prepare labeled non-nucleotide probes having the various chosen nucleobase sequences and then determine whether or not they would produce similar R-banding patterns as a way to test the binding affinity of these probes to randomly distributed repeat sequences in genomic nucleic acid and thereby score the result for each probe. Particularly because it was a consensus sequence that was being used to produce the PNA oligomers, and not one of the actual naturally occurring Alu-repeat sequences, testing was believed to be necessary to determine which of the nucleobase sequences hybridized most strongly to the Alu-repeat sequences of genomic nucleic acid.

For this purpose, a fluorescein labeled PNA oligomer was synthesized for each nucleobase sequence candidate (chosen candidates are listed in Table 2). The various PNA constructs were then evaluated in a PNA-FISH assay using the procedure discussed above. The most important of the parameters to be analyzed was the R-banding potential but the relative intensity of the R-banding signals was also examined. In each of the categories, the R-banding potential and signal intensity for each of the PNA oligomers was assigned a score from the minimum value of 0 to a maximum value of 6. To select for PNA oligomers that had the nucleobase sequences that were most suitable for use in probe mixture for blocking of the Alu repeats, all oligomers having an R-banding potential limit value of less than 3 where eliminated. The process was used to screen a total of 55 unique PNA oligomers, of which the 12 nucleobase sequences identified in Table 3 were found to be preferred because of their superior ability to bind to genomic nucleic acid.

TABLE 3

| Seq. Id. No. | Position[a] | Nucleobase Sequence | R-band Score | Signal Intensity |
|---|---|---|---|---|
| 3 | 9-25 | GGCCGGGCGCG GTGGCT | 4 | 5 |
| 4 | 26-43 | GCTGGGATTAC AGGCGTG | 5 | 6 |
| 5 | 49-64 | GGGAGGCCGAG GCGGG | 5 | 5 |
| 6 | 82-102 | GCCAGGCTGGT CTCGAACTCC | 4 | 4 |
| 7 | 112-132 | GAAACCCGTC TCTACTAAAA | 3 | 3 |
| 8 | 145-160 | GCCGGGCGTGG TGGCG | 5 | 4 |
| 9 | 163-180 | TAGCTGGGATT ACAGGCG | 6 | 5 |
| 10 | 184-200 | GGGAGGCTGAG GCAGGA | 6 | 6 |
| 11 | 201-221 | CCTCCCGGGTT CAAGCGATTC | 3 | 3 |
| 12 | 228-244 | TTGCAGTGAGC CGAGAT | 3 | 3 |
| 13 | 253-273 | TGCACTCCAGC CTGGGCGACA | 4 | 4 |
|  | 292[c] | [b]TT(k)TTTTT(k) TTTLysOLysOTTT (k)TTTTT(k)TT | 4 | 5 |

[a]Refers to the relative positions in the Alu consensus sequence depicted in FIG. 1.
[b]Triplex maker construct. k = D-Lysine; Lys = L-lysine; O = 8-amino-3,6-dioxaoctanoic acid.
[c]Hybridizes to the variable polyA tail of the alu sequence (Ullu E., TIBS: 216-219 (June, 1982)

Figures 1, 2:
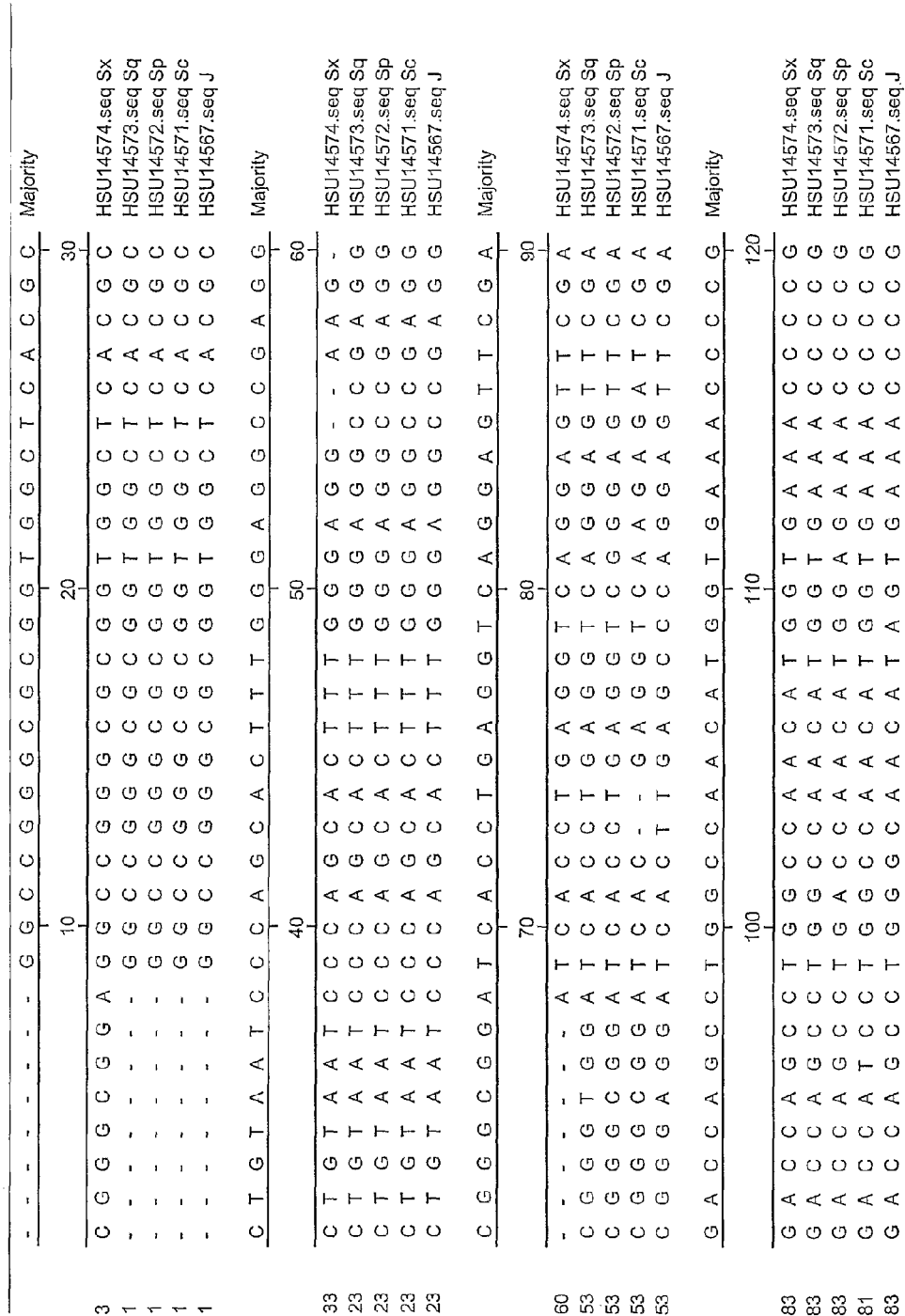

Results:

With reference to Table 3, there is data for each identified PNA oligomer that passed the limit value. For each entry, the relative position of the Alu consensus sequence, depicted in FIG. 2, is identified and the recorded R-banding value and Signal intensity score (average of 4-6 independent experiments) is reproduced. Representative examples of fluorescein labeled PNA oligomers that obtained a high score in the R-banding evaluation approach (Seq. Id No. 4 and Seq. Id. No. 10) and constructs that only just passed the limit value (Seq. Id. No. 7 and Seq. Id. No. 12) are shown in FIGS. 3A-1, 3A-2, 3B-1 and 3B-2, respectively. These images demonstrate that vast differences in performance exist for the various probes examined and therefore demonstrate that testing is a suitable way to determine which sequences were most effective at hybridizing to the randomly distributed repeat sequences of genomic nucleic acid.

Example 3: Effect of Sequence Variation

Experimental Design:

The Alu elements are dominated by the J and S family branches (Britten, R. J., Proc. Natl. Acad. Sci. USA, 91: 6148-6150 (1994); Batzer M A et al., J. Mol. Evol. (1996)). Especially noteworthy is the Sx subfamily, whereas the Y family branch constitute less than 0.5% of the total human Alu elements. In order to test the sensitivity by which the R-banding approach can detect the frequency of a specific sequence within the Alu elements, comparisons of almost identical PNA oligomer constructs were performed.

The constructs to be compared were directed towards identical positions within the Alu consensus sequence (FIG. 2) but the specific nucleobase sequence design was based on either the J and S family consensus or the Y family consensus. The images presented in FIG. 4 (A-D) were obtained using PNA oligomers that are complementary to positions 82-102 and 201-221 of the sequence shown in FIG. 2 (the PNA oligomer sequences are complimentary to the depicted consensus sequence). Within positions 82-102 the J and S consensus differ from the Y consensus by a T→A transversion at position 86 and a G→T transversion at position 96. Similarly, within position 201-221 a single point mutation (or single nucleotide polymorphism) correspondingly consists of a T→G transversion at position 208. The nucleobase sequence of the various PNA oligomer probes used in the experiments, as well as the respective R-band and Signal intensity scores of the examined oligomer constructs (FIG. 4), are presented in Table 4. R-band and Signal intensity scores represent average values from 8-10 independent experiments.

TABLE 4

| Seq. Id. No. | Alu consensus | Oligo sequence | Relative pos. in FIGS. 2-1-2-3 | R-band | Signal Intensity |
|---|---|---|---|---|---|
| 6 | J and S family | GCCAGGC TGGTCTC GAACTCC | 82-102 | 4 | 5 |
| 27 | Y family | GCCAGGA TGGTCTC GATCTCC | 82-102 | 2 | 2 |
| 11 | J and S family | CCTCCCG GGTTCAA GCGATTC | 201-221 | 3 | 3 |
| 28 | Y family | CCTCCCG GGTTCAC GCGATTC | 201-221 | 1 | 1 |

Results:

As can be seen by analysis of Table 4 and FIGS. 4 (A-D), these small changes (a single point mutation in one probe set and a double mutation in the other probe set) in the nucleobase sequence of the PNA oligomers significantly affects the efficiency by which the R-bands are formed. It is not known whether the R-band signals from hybridization experiments involving the Seq. Id. No. 27 and Seq. Id. No. 28 constructs (Y family consensus) reflect a low frequency of the corresponding genomic sequences, or rather that Seq. Id. No. 27 and Seq. Id. No. 28 hybridize to the consensus sequences of the J and S family with a reduced affinity. Nevertheless, this data reinforces the position that actual testing should be performed in order to determine which of all possible nucleobase sequences will produce the most complete hybridization to the randomly distributed repeat sequences and thereby presumably produce the most efficient blocking probes. Moreover, the aforementioned procedure appears to be well suited to determining the best candidates for further testing in a representative assay wherein there is substantial interfering cross reaction of a detectable probe to undesired sequence.

Example 4: Suppression of Undesired Signal Using a PNA Probe Mixture

Preparation of DNA Probe/Blocking Agent Mixture:

Fluorescence labeled COS or PAC based DNA probes were prepare made by culturing the COS or PAC containing E. coli and harvesting the human DNA from the cultures. The COS or PAC DNA was purified using Qiagen large construct kit (Qiagen, Kebolab A/S, Copenhagen, Denmark). The clones were checked by restriction enzyme digestion. From each clone, the DNA was labeled by conventional Nick translation using a monomer labeled with either fluorescein, Cy3, or Rhodamine. For the HER2 experiments illustrated in FIG. 5, the COSs were labeled with fluorescein; for the MLL experiments in FIG. 6, the two PAC clones flanking the breakpoint (van der Burg et al., Leukemia 13: 2107-2113 (1999)) were labeled in different colors, one with fluorescein the other with Cy3; for the HER2 experiments on tissue sections (FIG. 7) the COS clones were labeled with Rhodamine. In all experiments the labeled COS or PAC DNA probes were mixed with a blocking agent (PNA Oligomer Mixture or Cot-1 DNA) in DNA Hybridization Buffer (45% formamide, 300 mM NaCl, 5 mM $NaPO_4$, 10% Dextran sulphate). Each DNA probe was present at a final concentration of 2 ng/µL. When using the PNA Oligomer Mixture as a blocking agent, each PNA oligomer was present at a concentration of 5 µM in the hybridization buffer. With the Cot-1 DNA as blocking agent, a 100:1 weight ratio of Cot-1 DNA:total probe DNA was used in the assay.

Preferred Procedure for Performing In-Situ Hybridization Using Unlabelled PNAs as Blocking Agent:

Slides containing metaphase spreads and interphase nuclei were pre-treated as described above. The slide was immersed in TBS with 3.7% formaldehyde for 2 minutes at RT and PBS for 2 minutes at RT followed by dehydration in chilled (5° C.) ethanol series (70%, 85%, and 96%); 2 minutes each. On each pre-treated slide, 10 µL DNA of Hybridization Buffer with labeled DNA probe and unlabeled blocking agent (PNA Oligomer Mixture or Cot-1 DNA) is added and a 18 $mm^2$ coverslip is applied to cover the hybridization mixture. The edges of the coverslip were sealed with rubber cement and air-dried until the cement had set (around 5 min). The slide was denatured by incubation at 80° C. for 5 min. The slides were then hybridized O.N. at 37° C. (when Cot-1 DNA is used as blocking agent) or 45° C. (when PNA Oligomer Mixture is used as a blocking agent). After hybridization the coverslip was removed and the slide rinsed at RT in 0.1×SSC followed by wash for 2×10 minutes in 0.1×SSC at 55° C. (when Cot-1 DNA is used as the blocking agent) or 60° C. (when the PNA Oligomer Mixture is used as a blocking agent). Finally the slide was dehydrated in 70%, 85%, and 96% EtOH and air-dried as describe above. Each slide was mounted with 10 µL anti-fade solution, with 0.1 µg/mL 4,6-diamoni-2phenyl-indole (DAPI, Sigma Chemicals) and sealed with a coverslip. Slides were then analyzed using a microscope equipped with a CCD digital camera.

Experimental Design:

The Alu-banding approach (above) facilitated the identification of nucleobase sequences, within the Alu repeats, that seem to be present in the human genome with a high frequency. If Alu repeats are a major reason for non-target hybridization of large probes of genomic origin, a mixture of the identified PNA oligomer constructs should be able to suppress this undesired hybridization background. Therefore, unlabelled PNA oligomers having the preferred nucleobase sequences, as identified in Table 3, were prepared. These unlabeled and purified probes were mixed together and used in hybridization experiments as previously described (the "PNA Oligomer Mixture").

In addition to the unlabeled PNA probes, detectable nucleic acid probes of genomic origin were used in an assay to detect a genomic nucleic acid target. The detectable nucleic acid probes are COS clones covering around 100 kb of a region which include the HER-2 gene (17q21.1), or PAC clones covering 90 kb on each side of MLL gene (11q23) major breakpoint region (mbr). For this experiment, the detectable nucleic acid probes were labeled with fluorescein and the PNA oligomers were unlabeled.

Figure 5A:
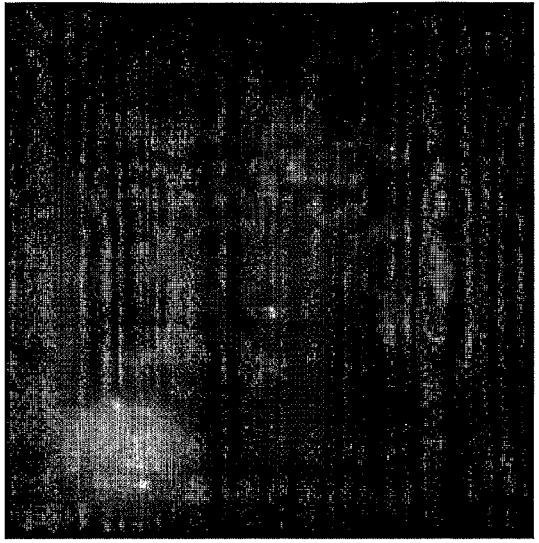
FIGS. 5A, 5B and 5C are microscope generated images of interphase nuclei and metaphase spread of human chromosomes treated with detectable HER-2 nucleic acid probe and either: 1) a blocking mixture of unlabeled PNA oligomers (5A); 2) Cot1 DNA blocker (5B) or is otherwise not treated with a blocking reagent (5C).
Figure 5B:
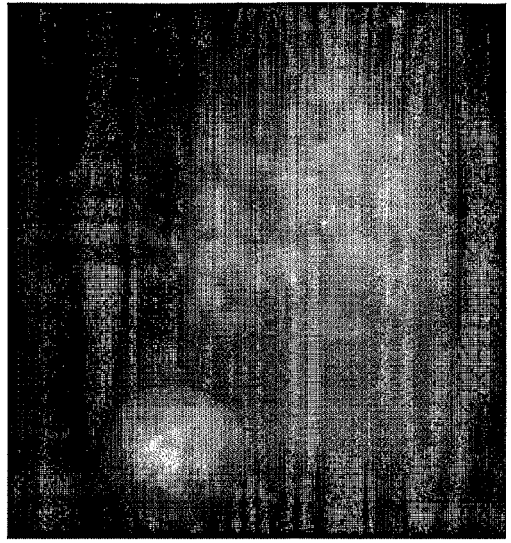
Figure 5C:
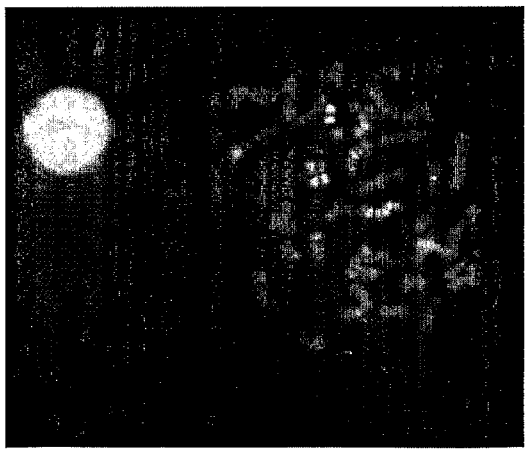

In one experiment, the fluorescein labeled HER-2 probes were hybridized to metaphase spreads and interphase nuclei. A representative microscope image of the resulting sample can be seen in FIG. 5A. This result was compared with the standard art recognized blocking reagent, Cot1 DNA (FIG. 5B: Human Cot-1 DNA from Gibco BRL, Life Technologies). In a separate sample, neither the PNA probe mixture nor the Cot1 DNA was added (FIG. 5C).

Figure 6A:
FIGS. 6A, 6B and 6C are microscope generated images of interphase nuclei and metaphase spread of human chromosomes treated with detectable MLL nucleic acid probe and either: 1) a blocking mixture of unlabeled PNA oligomers (6A); 2) Cot1 DNA blocker (6B) or is otherwise not treated with a blocking reagent (6C).
Figure 6B:
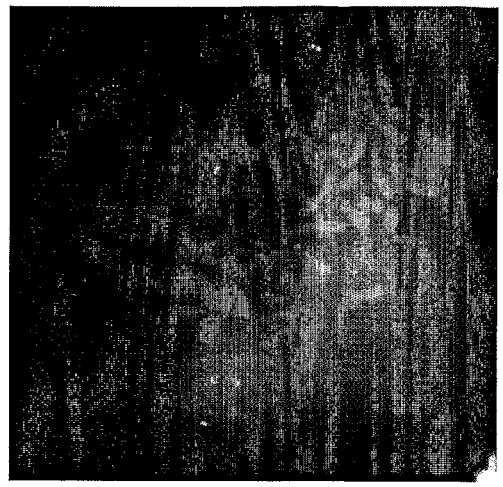
Figure 6C:
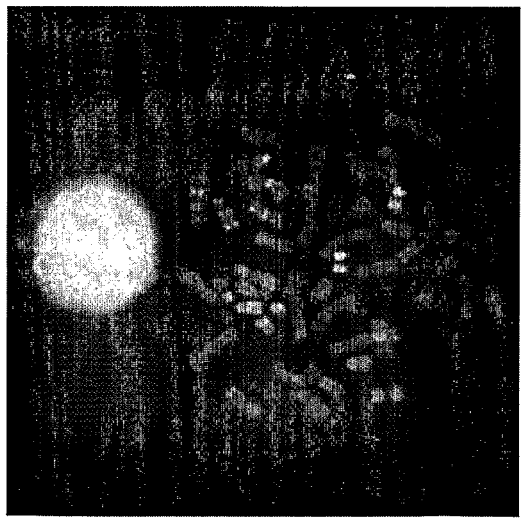

Translocations can be detected by a two color staining either by the "fusion" signal principle or the "split" signal principle. In the fusion signal principle the two genes involved in the translocation are labeled in each a separate color. In cells where a translocation has taken place the two colors will come together as a "fusion" signal. In the "split" signal principle the two differently labeled probes are localized around the breakpoint in one of the genes participating in the translocation (van der Burg et al., Leukemia 13: 2107-2113 (1999)). Thus, in abnormal cells the two probes will split as a result of the translocation. Similarly, the MLL probes labeled with fluorescein or Cy3 were hybridized to metaphase spreads and interphase nuclei using the same procedure as used for the HER 2 probes. A representative microscope image of the resulting sample can be seen in FIG. 6A. This result was compared with the standard art recognized blocking reagent, Cot1 DNA (FIG. 6B). In a separate sample, neither the PNA probe mixture nor the Cot1 DNA was added (FIG. 6C).

With reference to FIGS. 5 A-C and 6 A-C, it is apparent that in both cases the mixture of PNA probes appears to work as well as, if not better than, the industry standard, Cot1 DNA. It is also noteworthy that the absence of any blocking agent (e.g. PNA probe mixture or the Cot1 DNA) results in the formation of a hybridization background with a R-banding pattern, thereby indicating that non-target hybridization is caused by the presence of Alu repeats or other randomly distributed repeat sequence. The intensity of this background also seriously hinders the visualization of the single locus specific signals such that it must be removed in order to facilitate the performance of an accurate and reproducible assay.

Example 5: Suppression of Undesired Background in Tissue Sections Using the PNA Probe Mixture The PNA blocking mixture was used to suppress the undesired background staining from the HER2 probes described in Example 4 when used on tissue sections from a breast carcinoma. The DNA probes were labeled with Rhodamine and mixed with either the PNA Oligomer Mixture (FIG. 7A) or Cot-1 DNA (FIG. 7B). For comparison FIG. 7C shows the same experiment without any blocking agent added.

Preferred Procedure for Performing In-Situ Hybridization to Paraffin Embedded Mamma Carcinoma Sections Using Unlabelled PNAs as Blocking Agent:

Mamma carcinoma sections of 4 µm were cut from paraffin embedded tissue blocks. Slides mounted with tissue sections were deparaffinated in Xylene and 96% EtOH according to standard procedures (DAKO's handbook: Immunochemical Staining Methods). The slides were pre-treated in PBS for 10 min. at RT and 10 min. in boiling MES (2-[N-morpholino]ethanesulphonic acid) buffer, pH 6.4 followed by digestion in a 0.05% pepsin solution (0.05% pepsin in 0.02M HCl, 0.9% NaCl) for 10 min. at 37° C. The slides are washed for 3×2 minutes in PBS and dehydrated in chilled (5° C.) ethanol series (70%, 85%, and 96% EtOH, 2 minutes each). The slides were allowed to air-dry. For hybridization, 10 µL DNA hybridization buffer containing the labeled DNA probe and a blocking agent was added to the pre-treated slide and a 18 mm² coverslip was applied to cover the hybridization mixture. The edges of the coverslip were sealed with rubber cement and air-dried until the cement had set (around 5 min). The slide was denatured by incubation at 90° C. for 5 min. The slides were hybridized O.N. at 45° C. After hybridization the coverslip was removed and the slide was rinsed in pre-warmed (55° C.) 0.2×SSC with 0.1% TritonX-100 followed by a wash for 10 minutes in 0.2×SSC with 0.1% TritonX-100 at 55° C. Finally the slide was rinsed in PBS for 2 minutes at RT followed by dehydration in chilled ethanol series (70%, 85%, and 96% EtOH, 2 minutes each) and air-dried as described above. Each slide was mounted with 10 µL anti-fade solution with 0.1 µg/mL 4,6-diamoni-2phenyl-indole (DAPI, Sigma Chemicals) and sealed with a coverslip. Slides were then analyzed using a microscope equipped with a CCD digital camera.

Figure 7A:
FIGS. 7A, 7B and 7C are microscope generated images of paraffin embedded tissue sections of a breast carcinoma treated with detectable HER2 nucleic acid probe and either: 1) a blocking mixture of unlabeled PNA oligomers (7A); 2) Cot-1 DNA blocker (7B) or is otherwise not treated with a blocking reagent (7C).
Figure 7B:
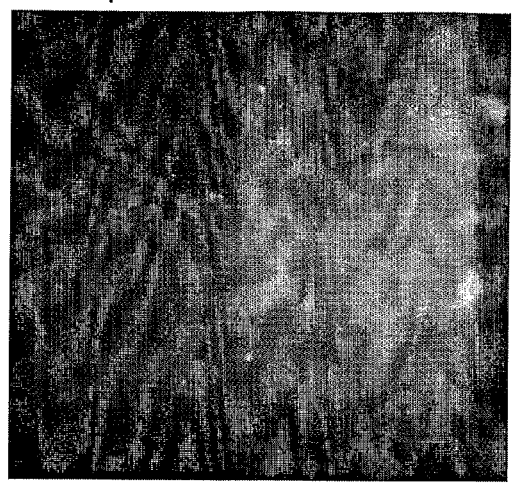
Figure 7C:

Results:

With reference to FIGS. 7A and 7B it is clear that there is very little difference in the performance of the PNA probe mixture vs. the Cot-1 DNA. Moreover, the absence of any blocking agent results in substantial background (FIG. 7C).

Example 6: More Examples of Chromosome Analysis

Synthesis and Labeling of Peptide Nucleic Acid Probes

The chromosome 17 centromere Peptide Nucleic Acids (PNAs) were synthesized at the 2-µmole scale on an Expedite 8900 nucleic acid synthesis system (Applied Biosystems, Foster City, Calif.) using Fmoc chemistry. The Alu PNAs were synthesized at the 5 µmole scale using a 433A nucleic acid synthesis system (Applied Biosystems, Foster City, Calif.) using t-boc chemistry. All of the PNAs were solubility enhanced using compound 4 as described (Gildea et al 1998). Attachment of a linker group while the oligomer was still bound to the column was accomplished by condensation of the expedite PNA linker, Fmoc-8-amino-3,6-dioxaotanoic acid. For 5(6)-carboxyfluorescein labeling the synthesis support was heated at 30° C. for five hours in 250 µL of a solution containing 0.08M dye as an NHS ester, (Molecular Probes, Eugene, Oreg.), 0.25M diisopropylethylamine and 0.2-M lutidine. The crude oligomer samples were then cleaved from the support by the use of standard methods, precipitated and purified by high performance liquid chromatography (HPLC) using 0.1% trifluoroacetic acid and a linear acetonitrile gradient.

Preparation of Chromosome Specific Probes

Chromosome 17 specific PNA probes (18-22 base units) were selected from published data available in public databases (e.g. Genbank). The following seven "Chromosome 17 PNA Probes" specific for the chromosome 17 α-satellite sequences were selected;

1. Flu-OEE-AAC-GAA-TTA-TGG-TCA-CAT-EEO-Lys(Flu)-NH$_2$
(SEQ ID NO: 55)

2. Flu-OEE-GGT-GAC-GAC-TGA-GTT-TAA-EEO-Lys(Flu)-NH$_2$
(SEQ ID NO: 56)

3. Flu-OEE-AAC-GGG-ATA-ACT-GCA-CCT-EEO-Lys(Flu)-NH$_2$
(SEQ ID NO: 57)

4. Flu-OEE-ATC-ACG-AAG-AAG-GTT-CTG-EEO-Lys(Flu)-NH$_2$
(SEQ ID NO: 58)

5. Flu-OEE-TTT-GGA-CCA-CTC-TGT-GGC-EEO-Lys(Flu)-NH$_2$
(SEQ ID NO: 59)

6. Flu-OEE-GAA-TCT-TCA-CAG-GAA-AGC-EEO-Lys(Flu)-NH$_2$
(SEQ ID NO: 60)

7. Flu-OEE-GAT-TCT-ACA-CAA-AGA-GAG-EEO-Lys(Flu)-NH$_2$
(SEQ ID NO: 61)

(Abbreviations are as previously described)

GenBank accession numbers U14567, U14568, U14569, U14570, U14571, U14572, U14573, U14574 representing the Alu consensus sequences were used to select sequences specific for the Alu family of interspersed repeats. The following eleven "Alu PNA Blocking Probes" selected from the consensus sequences were as follows:

1. H-EE-TTG-CAG-TGA-GCC-GAG-AT-EE-NH$_2$
(SEQ ID NO: 62)

2. H-EE-GGC-CGG-GCG-CGG-TGG-CT-EE-NH$_2$
(SEQ ID NO: 63)

3. H-EE-GCT-GGG-ATT-ACA-GGC-GTG-EE-NH$_2$
(SEQ ID NO: 64)

4. H-EE-GGG-AGG-CCG-AGG-CGG-G-EE-NH$_2$
(SEQ ID NO: 65)

5. H-EE-GCC-AGG-CTG-GTC-TCG-AAC-TCC-EE-NH$_2$
(SEQ ID NO: 66)

6. H-EE-GAA-ACC-CCG-TCT-CTA-CTA-AAA-EE-NH$_2$
(SEQ ID NO: 67)

7. H-EE-GCC-GGG-CGT-GGT-GGC-G-EE-NH$_2$
(SEQ ID NO: 68)

8. H-EE-TAG-CTG-GGA-TTA-CAG-GCG-EE-NH$_2$
(SEQ ID NO: 69)

9. H-EE-GGG-AGG-CTG-AGG-CAG-GA-EE-NH$_2$
(SEQ ID NO: 70)

10. H-EE-CCT-CCC-GGG-TTC-AAG-CGA-TTC-EE-NH$_2$
(SEQ ID NO: 71)

11. H-EE-TGC-ACT-CCA-GCC-TGG-GCG-ACA-EE-NH$_2$
(SEQ ID NO: 72)

(Abbreviations are as previously described)

Figure 8B:
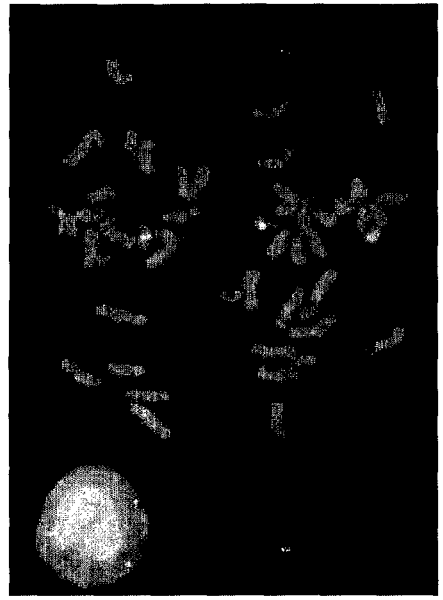
FIGS. 8A, 8B, 8C and 8D are microscope generated images of interphase nuclei and metaphase spreads treated with detectable HER2 nucleic acid probe and either: 1) no other probes (8A); 2) a mixture of Alu PNA Blocking Probes (8B); Chromosome 17 PNA Probes 8C); or Alu PNA Blocking Probes and Chromosome 17 PNA Probes (8D).
Figure 8D:
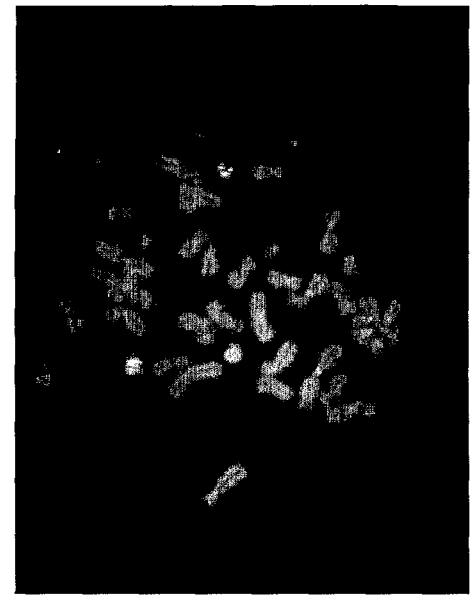
Figure 8A:
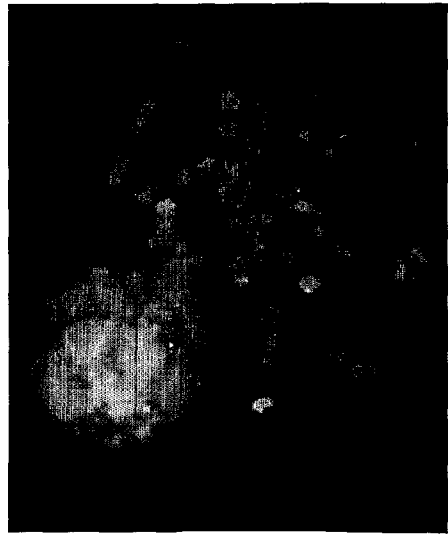
Figure 8C:

In-Situ Hybridization
  (i) Slide Preparation
  Slides containing metaphase spreads were prepared with standard cytogenetic techniques, essentially as previously described herein, and aged overnight then stored at −20° C. Prior to hybridization, the slides were removed from the freezer and allowed to warm to room temperature.
  (ii) Hybridization and Washings
  To 10 µL of hybridization mix containing 45% formamide, 10% dextran sulphate, 300 mM NaCl, 5 mM Na phosphate, 100 ng of rhodamine labeled Her2 DNA probe, and optionally as discussed below either or both of: (a) the Chromosome 17 PNA Probes at 30 nM each and/or (b) Alu PNA Blocking Probes at 5 µM each, were added to the slide. The slides were denatured at 70° C. for six minutes followed by hybridization overnight at 37° C. in a humidified chamber. After removal of the coverslip the slides are washed in a stringent wash solution (0.2×SSC with 0.1% Triton X-100) at 65° C. for 10 minutes. The slides were then rinsed in TBS buffer for 2 minutes. Cells were counterstained with DAPI and mounted in Vectashield anti-fade medium.
  (iii) Digital Imaging Microscopy
  Digital images of metaphase cells after FISH with fluorescein labeled Chromosome 17 PNA Probes and/or Rhodamine labeled Her2 DNA probes were acquired with a cool snap FX 12 bit CCD camera (Roper Scientific, Tucson Ariz.) attached to an Olympus AX 70 microscope using Openlab software (Improvision Inc., Lexington, Mass.). The microscope was equipped with SP100, 41001, SP102, SP102, SP104 and SP105 filter sets for multicolor FISH (Chroma Technology, Brattleboro, Vt.). Images of each fluorescent dye were acquired, avoiding over or under exposure and stored for further analysis. After thresholding and contrast enhancement using Openlab software (Improvision Inc., Lexington, Mass.), pixels above a selected threshold from each fluorescent dye were projected on to the DAPI image.
Results:
  As described above, a series of experiments were designed to establish the usefulness of a mixture of Alu PNA Blocking Probes in the analysis of genomic nucleic acid in FISH experiments. First, the affect of hybridizing a rhodamine labeled genomic DNA probe (rhodamine labeled Her2 DNA) in the absence of Alu PNA Blocking Probes was used as a control. With respect to FIG. 8A, the interphase and metaphase cells were stained bright red with non-specific staining clearly visible. There was little or no differentiation between the specific Her2 signal and the non-specific background staining. In addition, the morphology of the chromosomes was extremely poor.
  By comparison, the affect of hybridizing the same labeled genomic probe (rhodamine labeled Her2 DNA), wherein Alu PNA Blocking Probes were present, was performed. With respect to FIG. 8B, the interphase and metaphase cells contain low non-specific staining and bright specific red Her2 signal on the long arm of chromosome 17. This demonstrates that the presence of the Alu PNA Blocking Probes significantly reduce non-specific hybridization.
  To confirm that the observed signal was present on chromosome 17, and not on another chromosome, in the next series of experiments a mixture of Fluorescein Chromosome 17 PNA Probes were included in the hybridization mix along with the rhodamine labeled Her2 DNA probe, both with (FIG. 8C) and without Alu PNA Blocking Probes (FIG. 8D).
  With reference to FIG. 8C, hybridization of the rhodamine labeled Her2 DNA probe and the Fluorescein Chromosome 17 PNA Probe mix, in the absence of Alu PNA Blocking Probes, produces results that are similar to FIG. 8A, wherein the Fluorescein Chromosome 17 PNA Probe are omitted except there was non-specific binding of the probe to the glass slide. Specifically, there is too much non-specific signal for the assay to be of practical utility. By comparison, FIG. 8D shows the effect of including the Alu blocking probes. In this Figure there is a bright red specific Her2 signal on the long arm of chromosome 17 (as indicated by the arrows) with low non-specific staining of the interphase cells and metaphase chromosomes with little or no non specific hybridization on the glass slide. Because the Fluorescein Chromosome 17 PNA Probes were present in the mix, it is confirmed that the green signal correlates with the red signal, thereby confirming that the DNA probe hybridizes specifically to chromosome 17 and not another chromosome.

Example 7: Detection of Translocation of the CyclinD1 Gene Using Suppression of Undesired Background with the PNA Oligomer Mixture Preparation of DNA Probe/Blocking Agent Mixture:
  Fluorescence labeled BAC based DNA probe was prepare made by culturing the BAC containing *E. coli* and harvesting the human DNA from the cultures. The BAC DNA was purified using Qiagen large construct kit (Qiagen, Kebolab A/S, Copenhagen, Denmark). The clone was checked by restriction enzyme digestion and end sequenced. The clone DNA was labeled by conventional Nick translation using a monomer labeled with fluorescein. In all experiments the labeled DNA probe was mixed with a blocking agent (with or without PNA Oligomer Mixture or Cot-1 DNA) in DNA Hybridization Buffer (45% formamide, 300 mM NaCl, 5 mM NaPO$_4$, 10% Dextran sulphate). The DNA probe was present at a final concentration of 5 ng/µL. The centromeric PNA probe was labeled with Rhodamine and present at a final concentration of 50 nM. When using the PNA Oligomer Mixture as a blocking agent, each PNA oligomer was present at a concentration of 5 µM in the Hybridization Buffer. With the Cot-1 DNA as blocking agent, a 100:1 weight ratio of Cot-1 DNA:total probe DNA was used in the assay.
Preferred Procedure for Performing In-Situ Hybridization Using Unlabelled PNAs as Blocking Agent:
  Slides containing metaphase spreads and interphase nuclei were pre-treated as described above. The slides were immersed in TBS with 3.7% formaldehyde for 2 minutes at RT and PBS for 2 minutes at RT followed by dehydration in chilled (5° C.) ethanol series (70%, 85%, and 96%); 2 minutes each. On each pre-treated slide, 10 µL DNA of Hybridization Buffer with labeled DNA probe and unlabeled blocking agent (PNA Oligomer Mixture or Cot-1 DNA) is added and a 18 mm$^2$ coverslip is applied to cover the hybridization mixture. The edges of the coverslip were sealed with rubber cement before treatment at 80° C. for 5 min. The slides were then hybridized O.N. at 45° C. After hybridization, the coverslip was removed and the slide rinsed at RT in Stringent Wash Buffer (0.2×SSC, 0.1% Triton X-100) followed by wash for 10 minutes in Stringent Wash Buffer at 65° C. Finally the slide was dehydrated in 70%, 85%, and 96% EtOH and air-dried as describe above. Each slide was mounted with 10 µL anti-fade solution, with 0.1 µg/mL 4,6-diamoni-2-phenyl-indole (DAPI, Sigma Chemicals) and sealed with a coverslip. Slides were then analyzed using a microscope equipped with a CCD digital camera.

Experimental Design:

The Alu-banding approach (above) facilitated the identification of nucleobase sequences, within the Alu repeats, that seem to be present in the human genome with a high frequency. If Alu repeats are a major reason for non-target hybridization of large probes of genomic origin, a mixture of the identified PNA oligomer constructs should be able to suppress this undesired hybridization background. Therefore, unlabelled PNA oligomers having the preferred nucleobase sequences, as identified in Table 3, were prepared. These unlabeled and purified probes were mixed together and used in hybridization experiments as previously described.

Figure 9:
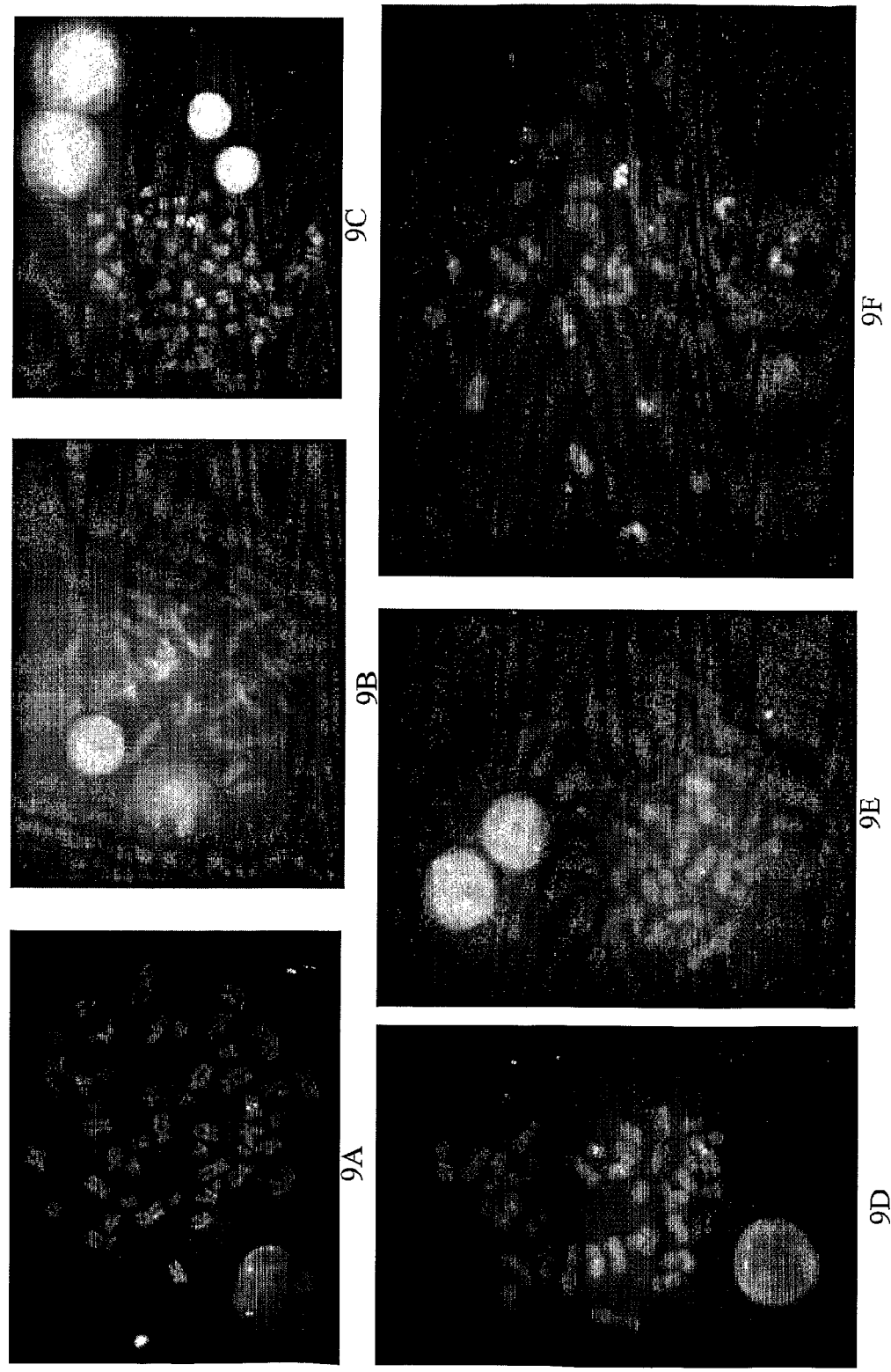
FIGS. 9A, 9B, 9C, 9D, 9E and 9F are microscope generated images of interphase nuclei and metaphase spreads treated to determine the CyclinD1 gene.

Results:

Since the CyclinD1 gene is located on chromosome band 11q23, a PNA mixture for the centromere of chromosome 11 (See U.S. Ser. No. 09/520,760 or U.S. Ser. No. 09/627,796, herein incorporated by reference) was prepared and added to the assay to thereby identify the chromosome to which the CyclinD1 probe hybridizes. The PNA oligomers for the centromere of chromosome 11 were labeled with Rhodamine. FIG. 9A shows both centromeres of chromosome 11 in red, as well as the green CyclinD1 probes. FIG. 9B shows the same probes wherein Cot-1 DNA is used as compared with the PNA Oligomer Mixture. The red centromere signals are not visible as Cot-1 also contains centromeric sequences and thus compete with the PNA in binding to the centromere. FIG. 9C show the same probes without any blocking agent added. It is not possible to identify either of the red or the green signals in the interphase nuclei. In the metaphase spread, only the centromere signals (in red) can be seen.

The CyclinD1 probe and the Centromere 11 PNA was also hybridized to metaphase spreads of the cell line Granta 519 ((Drexler, H. G. (2001) The Leukemia-Lymphoma Cell Line Facts Book. Braunschweig, Germany)) that harbors a translocation of the CyclinD1 gene. The probe was labeled with fluorescein and mixed with either the PNA Oligomer Mixture (FIG. 9D) or Cot-1 DNA (FIG. 9E). For comparison FIG. 9C shows the same experiment without any blocking agent added.

Example 8: Detection of Amplification of the c-MYC Gene Using Suppression of Undesired Background with the PNA Oligomer Mixture The c-MYC DNA probe was prepared as described in example 7. Furthermore, a DNA based centromere probe was used instead of a PNA based centromere probe. The DNA centromere DNA probe was prepare by culturing the centromere DNA plasmid containing E. coli and harvesting the human DNA from the cultures. The plasmid DNA was purified using Qiagen plasmid kit (Qiagen, Kebolab A/S, Copenhagen, Denmark). The clone DNA was labeled by conventional Nick translation using a monomer labeled with fluorescein. The DNA based centromere probe was used at a final concentration of 2 pg/µL. The procedure for performing in-situ hybridization is described in Example 7.

Figure 10:
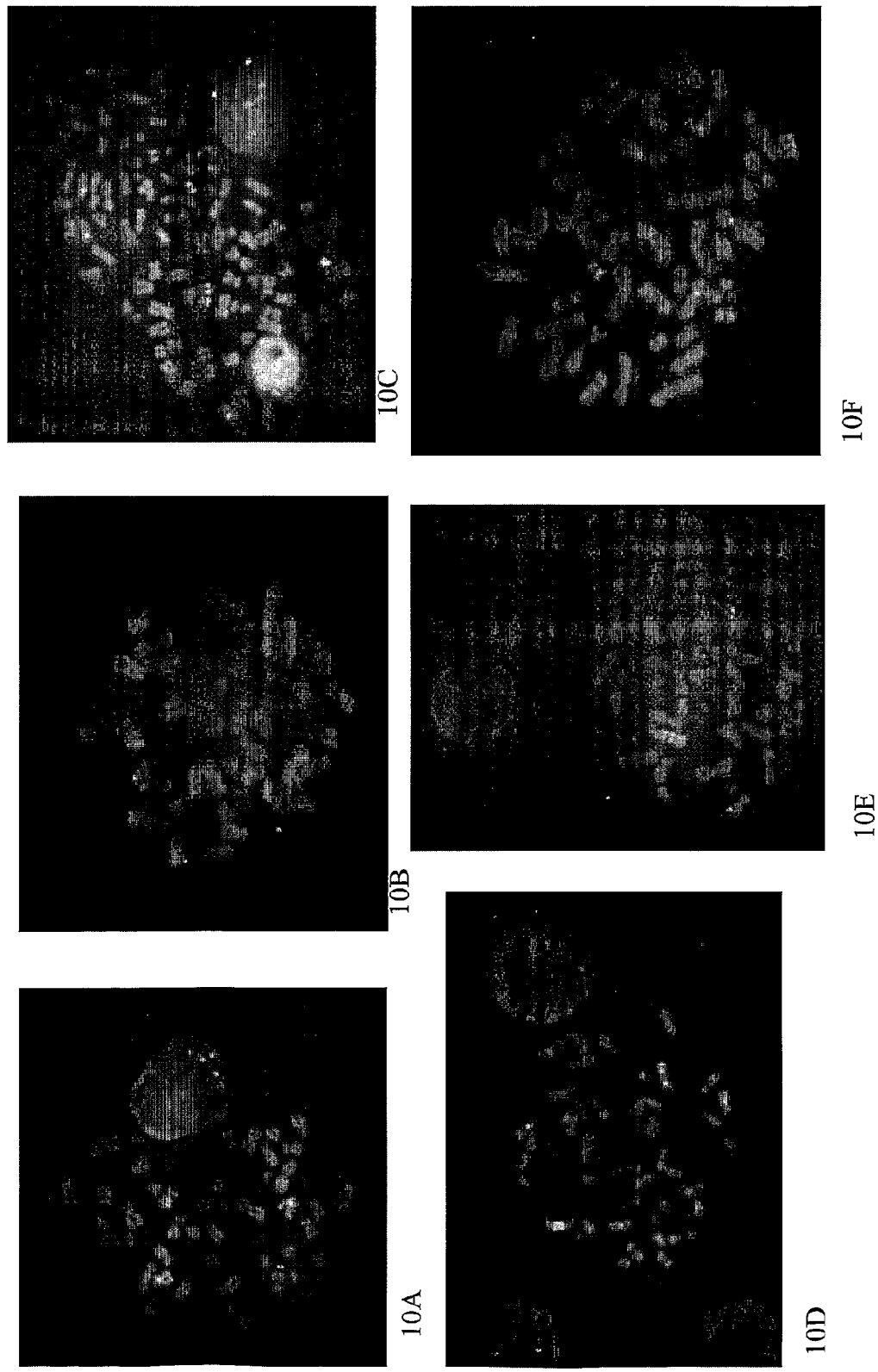
FIGS. 10A, 10B, 10C, 10D, 10E and 10F are microscope generated images of interphase nuclei and metaphase spreads treated to determine the c-MYC gene.

Results:

The PNA Oligomer Mixture was used to suppress the undesired background staining from a c-MYC probe when used on normal metaphase spreads and interphase nuclei. The c-MYC probe was labeled with Texas Red and mixed with either the PNA Oligomer Mixture (FIG. 10A) or Cot-1 DNA (FIG. 10B). For comparison FIG. 10C shows the same experiment without any blocking agent added. Since the c-MYC gene is located on chromosome band 8q24, a DNA probe for the centromere of chromosome 8 was added to identify the chromosome to which the c-MYC probe hybridizes (See discussion above with respect to the preparation of the DNA centromere probe for chromosome 8). The DNA for centromere 8 was labeled with fluorescein. FIG. 10A shows both centromeres clearly and both genes localized on chromosome 8. In the same Figure an interphase nuclei shows two separate red and two separate green signals thereby confirming the determination of the c-MYC gene on chromosome 8. FIG. 10B shows the result when using Cot-1 DNA instead of the PNA Oligomer Mixture. The green centromere signals are not visible as Cot-1 also contains centromeric sequences and thus compete with the DNA in binding to the centromere. FIG. 10C show the same experiment without any blocking agent added (i.e. no PNA Oligomer Mixture and no Cot1-PNA). Only the centromere signals (in green) can be clearly seen. The red signals from the cMYC gene can not be seen due to the high background staining.

The c-MYC probe and the centromere 8 DNA probe were also hybridized to metaphase spreads of the cell line HMT3522 (Nielsen et al., 1997) that has amplification of the c-MYC gene. The c-MYC probe was labeled with Texas Red, the DNA probe for the centromere of chromosome 8 was labeled with fluorescein. These probes were mixed with either the PNA Oligomer Mixture (FIG. 10D) or Cot-1 DNA (FIG. 10E). For comparison, FIG. 10F shows the result of the same experiment performed without any blocking agent added. Using the PNA Oligomer Mixture both the green centromere 8 signals and the amplified c-MYC signals (in red) can be seen. Using Cot-1 DNA only the red c-MYC signals can bee seen. Omitting the blocking agent makes it impossible to discriminate between red signals and background.

Ref: Nielsen K V, Niebuhr E, Ejlertsen 13, Holstebroe S, Madsen M W, Briand P, Mouridsen H T, Bolund L. Molecular cytogenetic analysis of a nontumorigenic human breast epithelial cell line that eventually turns tumorigenic: Validation of an analytical approach combining karyotyping, comparative genomic hybridization, chromosome painting, and single-locus fluorescence in situ hybridization. Genes Chromosomes Cancer. 1997; 20:30-37.

Example 9: Detection of Amplification of the EGFR Gene Using Suppression of Undesired Background with the PNA Oligomer Mixture The PNA blocking mixture was used to suppress the undesired background staining from a EGFR probe when used on normal metaphase spreads and interphase nuclei. The EGFR probe was prepared essentially as described in Example 8. The procedure for in-situ hybridization on tissue was performed essentially as described in Example 5. The procedure for in-situ hybridization on metaphase spreads was performed essentially described in Example 7.

Figure 11:
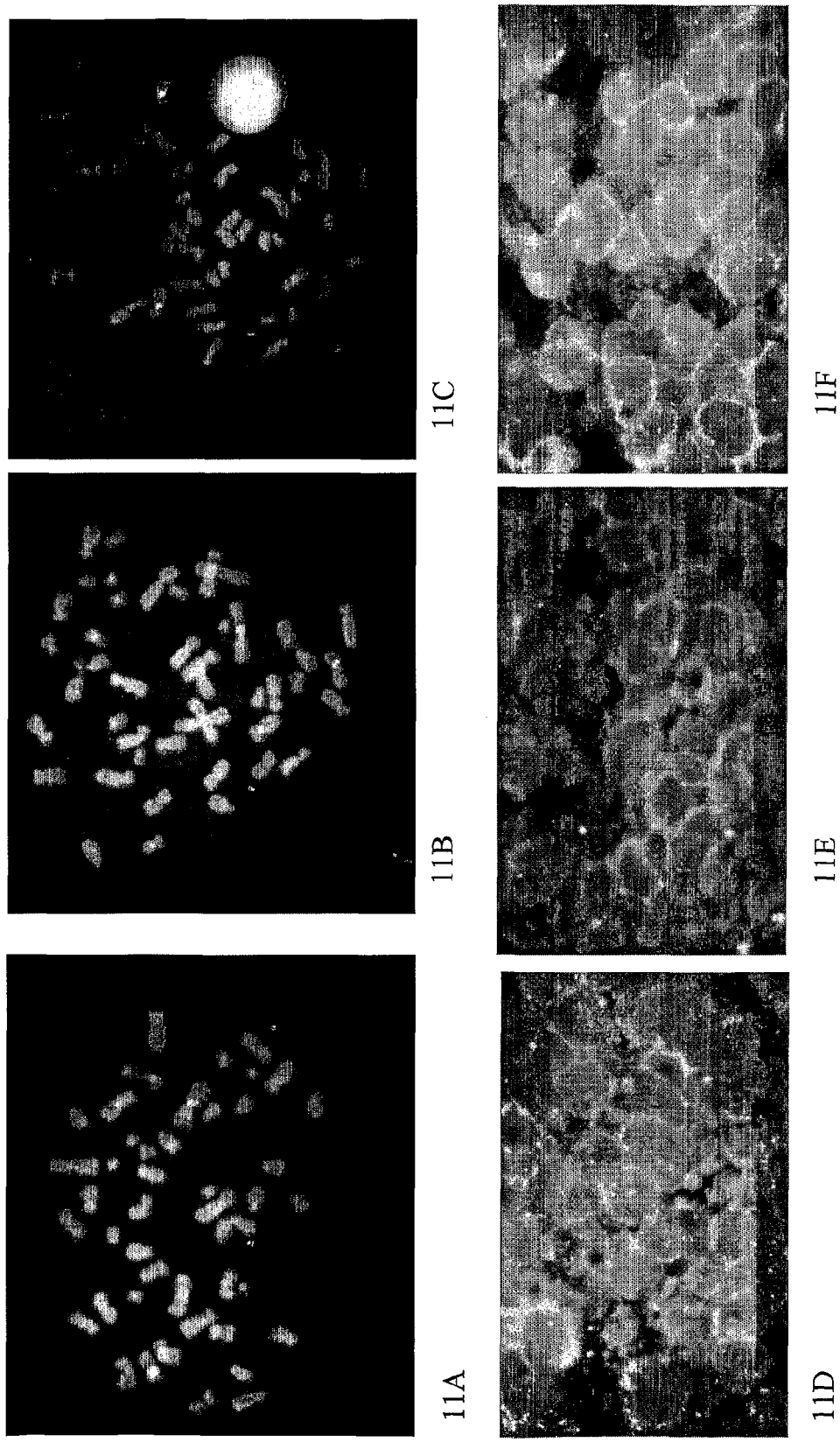
FIGS. 11A, 11B, 11C, 11D, 11E and 11F are microscope generated images of interphase nuclei and metaphase spreads treated to determine the EGFR gene.

Results:

The EGFR gene is located on the short arm of chromosome 7. Therefore a DNA probe for the centromere of chromosome 7 was added to identify the chromosome to which the EGFR probe hybridizes. The DNA for centromere 7 was labeled with fluorescein. The EGFR probe was labeled with Texas Red and mixed with either the PNA Oligomer Mixture (FIG. 11A) or Cot-1 DNA (FIG. 11B). For comparison FIG. 11C shows the result of the same experiment performed without any blocking agent added.

FIG. 11A shows both centromeres clearly and both genes localized on chromosome 7. FIG. 11B shows the same probes except that Cot-1 DNA was substituted for the PNA Oligomer Mixture. The green centromere signals are nearly invisible as Cot-1 also contains centromeric sequences and thus compete with the DNA in binding to the centromere. FIG. 11C shows the result of performing the assay in the absence of any blocking agent. Only the centromere signals (in green) can be seen clearly. The red signals from the EGFR gene are difficult to distinguish from the high background staining.

The EGFR probe and the centromere 7 DNA probe were also hybridized to human lung tissue that has amplification of the EGFR gene. The EGFR probe and the DNA probe for the centromere of chromosome 7 were mixed with either the PNA Oligomer Mixture (FIG. 11D) or Cot-1 DNA (FIG. 11E). For comparison, FIG. 11F shows the result of the same experiment performed without any blocking agent added. Using the PNA Oligomer Mixture both the green centromere 7 signals and the amplified EGFR signals (in red) can be seen. Using Cot-1 DNA only the red EGFR signals can bee seen. Omitting blocking agent interferes marginally with signal recognition, since only a slight increase in background staining is seen.

Example 10: Suppression of Undesired Background Using the PNA Oligomer Mixture in Combination with a TOP2A DNA Probe and a CEN-17 PNA Probe The PNA Oligomer Mixture was used to suppress the undesired background staining from the TOP2A DNA probe and CEN-17 PNA probe. This assay has been launched as a kit by DakoCytomation with the product code no. K5333. The TOP2A DNA probe, labeled with Texas Red and the CEN-17 PNA probe labeled with fluorescein were prepared essentially as described in Example 4. A mixture of the PNA and DNA probes was tested on normal metaphase spreads (FIGS. 12A, 12B and 12C), essentially as described in Example 7 and on formalin fixed, paraffin embedded cells from the cell line MDA-361 (breast cancer cell line with TOP2A deletion (Jarvinen T A, Tanner M, Rantanen V, Barlund M, Borg A, Grenman S, et al. Amplification and deletion of topoisomerase IIalpha associate with ErbB-2 amplification and affect sensitivity to topoisomerase II inhibitor doxorubicin in breast cancer. Am J Pathol 2000; 156: 839-4; FIGS. 12D, 12E and 12F) and a mama carcinoma with borderline amplification (FIGS. 12G, 12H and 12I) essentially as described in Example 5. The TOP2A DNA probe and CEN-17 PNA probe (See U.S. Ser. No. 09/520,760 or U.S. Ser. No. 09/627,796, herein incorporated by reference) were mixed with either the PNA Oligomer Mixture (FIGS. 12A, 12D and 12G) or Cot-1 DNA (FIGS. 12B, 12E and 12H). For comparison FIGS. 12C, 12F and 12I show the result of performing the same assay in the absence of any blocking agent.
Results:

FIGS. 12A, 12B and 12C demonstrates the ability for the PNA Oligomer Mixture to block unspecific background when detecting the TOP2A gene on normal metaphase spreads using the green CEN-17 PNA probe as a reference. Green and red signal are clearly visible using the PNA mixture as a blocking reagent (12A), whereas the green signals are somewhat dimmer when using Cot-1 DNA as a blocking reagent (12B). Specific signals cannot be distinguished from background in the absence of any blocking reagent (12C).

FIGS. 12D, 12E and 12F demonstrates the ability of the PNA Oligomer Mixture to block unspecific background when detecting a TOP2A gene deletion in MDA-361 cells, using CEN-17 as a reference. Green and red signal are clearly visible using either the PNA Oligomer Mixture (12D) or Cot-1 DNA as a blocking reagent (12E). Specific signals cannot be distinguished from background in the absence of any blocking reagent (12F).

FIGS. 12G, 12H and 12I demonstrate the ability for the PNA Oligomer Mixture to block unspecific background when determining the ratio between the TOP2A gene and CEN-17 in a human mama carcinoma. Green and red signal are clearly visible using either the PNA Oligomer Mixture (12G) or Cot-1 DNA (12H) as a blocking reagent. Specific signals cannot be distinguished from background in the absence of any blocking reagent (12I).

Figure 13:
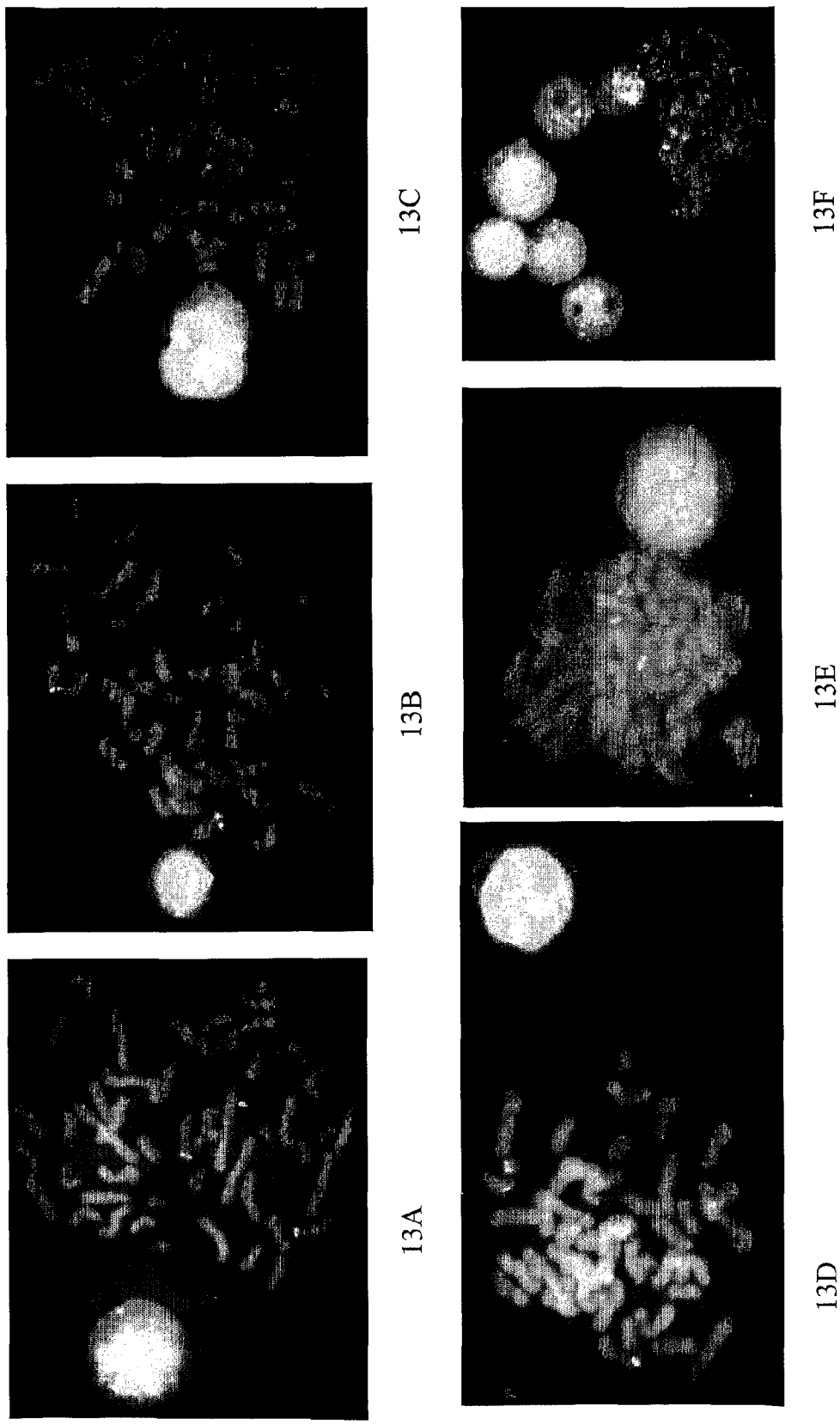
FIGS. 13A, 13B, 13C, 13D, 13E and 13F are microscope generated images of interphase nuclei and metaphase spreads treated to determine the TEL gene.

Example 11: Detection of Translocation of the TEL Gene Using Suppression of Undesired Background with the PNA Oligomer Mixture The PNA Oligomer Mixture was used to suppress the undesired background staining from TEL probes when used on normal metaphase spreads and interphase nuclei. The TEL probes was prepared essentially as described in Example 7, provided however that BAC DNA and PAC DNA were used. The upstream clone DNA was labeled with Texas Red and the downstream clone DNA was labeled with fluorescein by conventional Nick translation using a monomer labeled with Texas Red or fluorescein, as appropriate. The DNA based probes were used at a final concentration of 50 ng/µL. The procedure for performing in-situ hybridization is essentially as described in Example 7. The DNA probes were mixed with either the PNA Oligomer Mixture (FIG. 13A) or Cot-1 DNA (FIG. 13B). For comparison FIG. 13C shows the same experiment without any blocking agent added.

The TEL gene is located on chromosome band 12p13. FIG. 13A shows normal TEL configurations on metaphases with a yellow signal located on both chromosome 12. Two yellow signals in interphase nuclei indicate two normal TEL loci. FIG. 13B shows the result using Cot-1 DNA instead of the PNA Oligomer Mixture. FIG. 13C shows the result of the same assay except that no blocking agent added. It is not possible to identify either the red or the green signals in the interphase nuclei and metaphase spread in the absence of a blocking reagent.

The TEL probes were also hybridized to metaphase spreads of the cell line REH (Drexler, H. G. (2001) The Leukemia-Lymphoma Cell Line Facts Book. Braunschweig, Germany.) that harbors a translocation t(12;21)(p13,q22). The assay was performed with either the PNA Oligomer Mixture (FIG. 13D) or Cot-1 DNA (FIG. 13E). FIG. 13D and FIG. 13E shows one green signals located on der(12) and a red signal on der(21), indicating a split of the upstream TEL and downstream TEL probes. This is indicative of a translocation. A green signal on the other allele of chromosome 12 would indicate a deletion of the upstream TEL. For comparison, FIG. 13F shows the result of performing the same assay in the absence of any blocking agent.

Example 12: Detection of Translocation of the E2A Gene Using Suppression of Undesired Background with the PNA Oligomer Mixture The PNA Oligomer Mixture was used to suppress the undesired background staining from E2A probes when used on normal metaphase spreads and interphase nuclei. The BCR probes was prepared essentially as described in Example 11. In-situ hybridization was performed essentially as described in Example 7.

Figure 14:
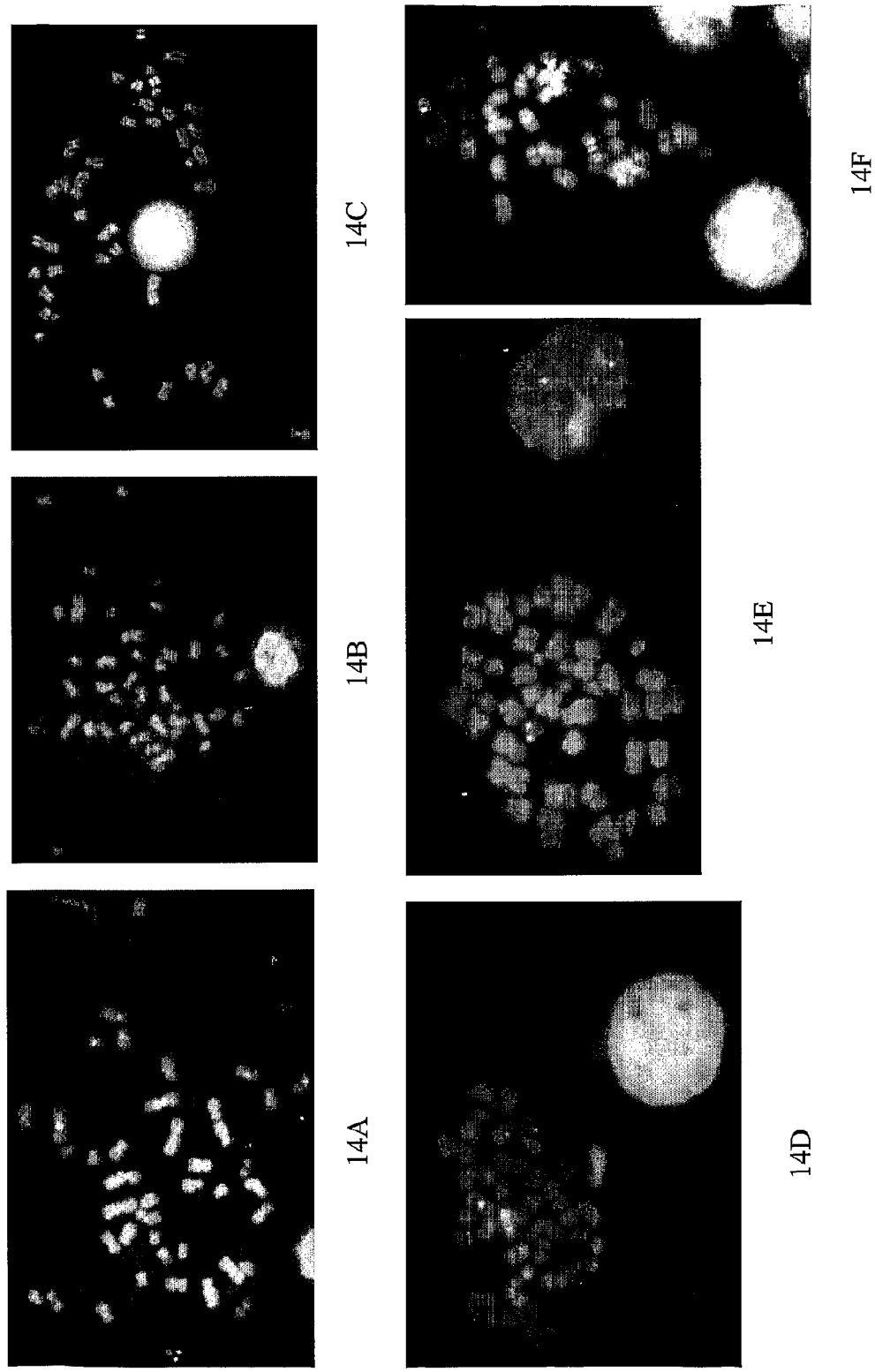
FIGS. 14A, 14B, 14C, 14D, 14E and 14F are microscope generated images of interphase nuclei and metaphase spreads treated to determine the E2A gene.

The upstream E2A probe was labeled with fluorescein and the downstream E2A probe with Texas Red. The E2A gene is located on chromosome band 19p13. FIG. 14A show normal E2A configurations on metaphases with a yellow signal (mixture of red and green signals) located on both chromosome 19. Two yellow signals in interphase nuclei indicate two normal E2A loci. FIG. 14B show the result when the assay is performed with Cot-1 DNA instead of the PNA Oligomer Mixture. FIG. 14C show the result when the assay is performed without any blocking agent. It is not possible to identify neither the red nor the green signals in the interphase nuclei and metaphase spread.

The E2A probes were also hybridized to metaphase spreads of the cell line 697 (Drexler, H. G. (2001) The Leukemia-Lymphoma Cell Line Facts Book. Braunschweig, Germany) that harbors a translocation t(1;19)(q23,p13). The E2A DNA probes were labeled as above and mixed with either the PNA Oligomer Mixture (FIG. 14D) or Cot-1 DNA (FIG. 14E). FIG. 14D and FIG. 14E shows one yellow signal indicating a normal E2A allele and a red signal on der(1) while the der(19) is lost, indicating a split of the upstream BCR and downstream BCR probes. This result is indicative of a translocation. For comparison FIG. 14F shows the result of performing the assay in the absence of any blocking agent.

Example 13: Detection of Translocation of the BCR Gene Using Suppression of Undesired Background with the PNA Oligomer Mixture The PNA Oligomer Mixture was used to suppress the undesired background staining from BCR probes in normal metaphase spreads and interphase nuclei. The upstream BCR DNA probe was labeled with fluorescein and the downstream BCR DNA probe with Texas Red. The BCR probes were prepared essentially as described in Example 11. However, COS DNA was also included as probe. The COS DNA was labeled with Texas Red by conventional Nick translation using a monomer labeled with Texas Red. The procedure for performing in-situ hybridization was performed essentially as described in Example 7.

Figure 15:
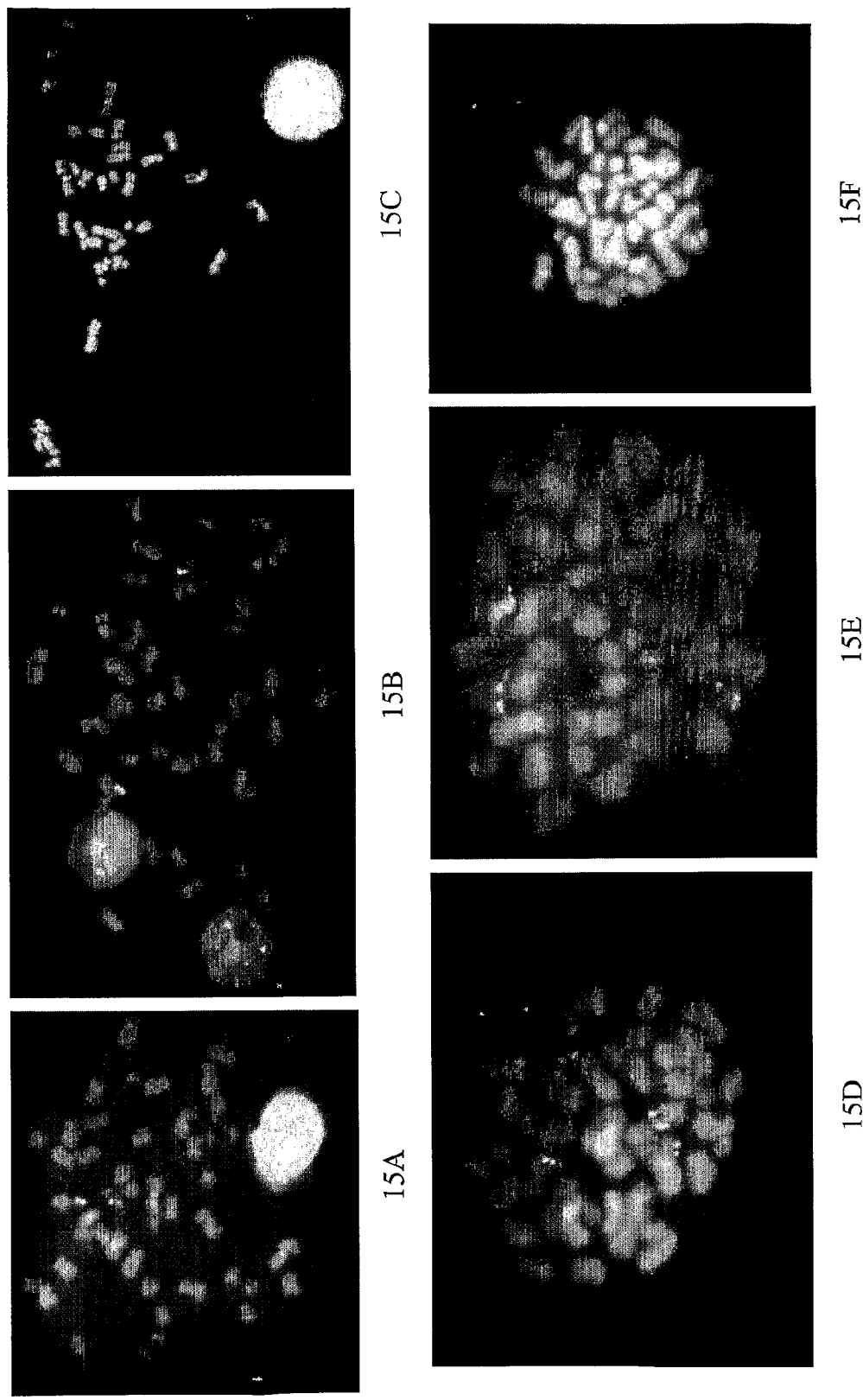
FIGS. 15A, 15B, 15C, 15D, 15E and 15F are microscope generated images of interphase nuclei and metaphase spreads treated to determine the BCR gene.

These DNA probe were mixed with either the PNA Oligomer Mixture (FIG. 15A) or Cot-1 DNA (FIG. 15B). For comparison FIG. 15C shows the result of performing the same assay in the absence of blocking agent.

The BCR gene is located on chromosome band 22q11. FIG. 15A show normal BCR configurations on metaphases with a yellow signal located on both chromosome 22. Two yellow signals in interphase nuclei indicate two normal BCR loci. FIG. 15B show the same probes suppressed with Cot-1 DNA. FIG. 15C show the same probes without any blocking agent added. It is not possible to identify the red or the green signals in the interphase nuclei and metaphase spread in the absence of a blocking reagent.

The BCR probes were also hybridized to metaphase spreads of the cell line BV173 (Drexler, H. G. (2001) The Leukemia-Lymphoma Cell Line Facts Book. Braunschweig, Germany) that harbors a translocation t(9;22)(q34,q11). The BCR probes were labeled as above and mixed with either the PNA Oligomer Mixture (FIG. 15D) or Cot-1 DNA (FIG. 15E). FIG. 15D and FIG. 15E shows one yellow signal, indicating a normal BCR allele, and one green signals located der(9) and a red signal on der(22); indicating a split of the upstream BCR and downstream BCR probes. This result is indicative of a translocation. An additional red signal is indicative of an additional der(22). For comparison, FIG. 15F shows the result of performing the same assay in the absence of blocking agent.

Figure 16:
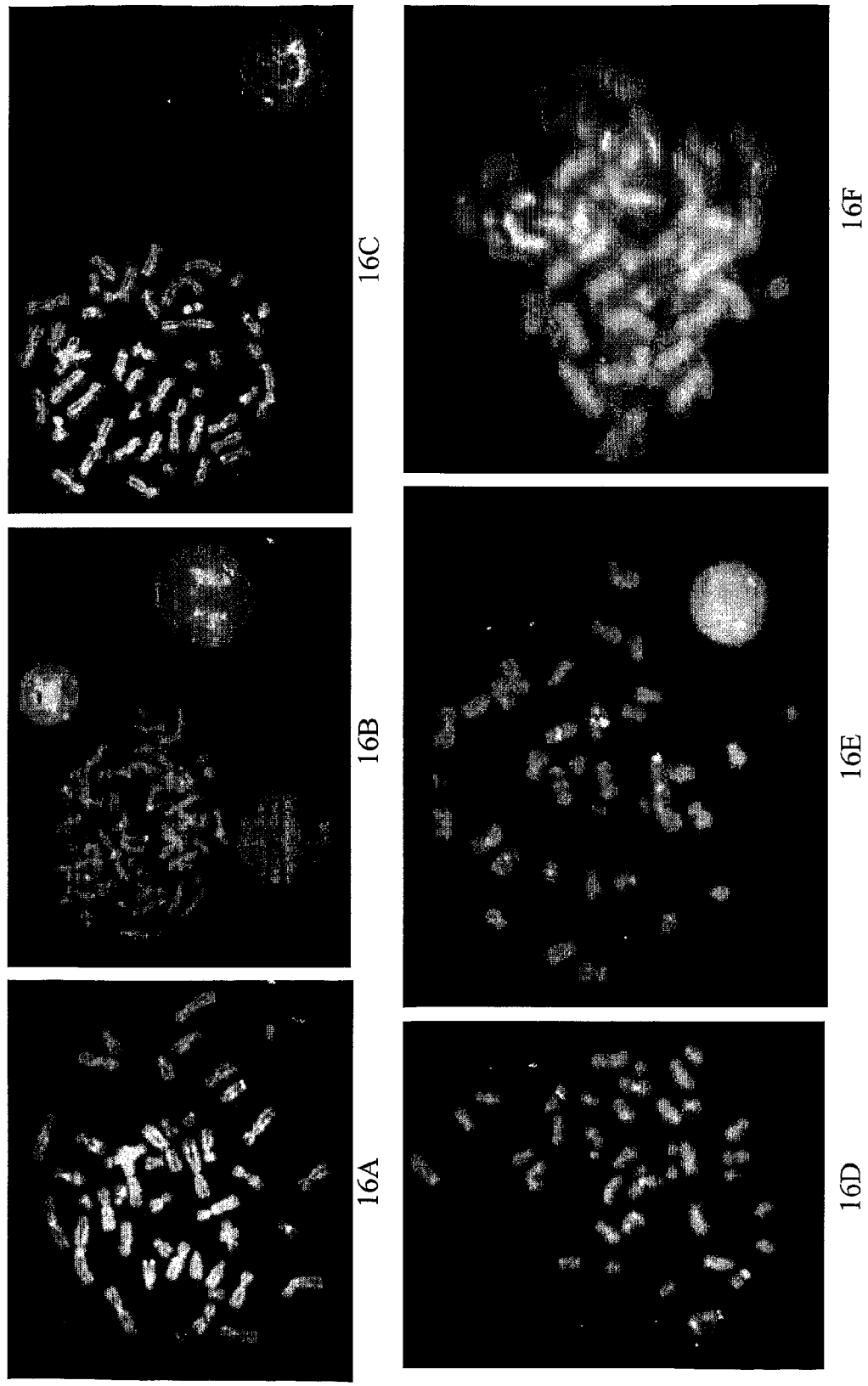
FIGS. 16A, 16B, 16C, 16D, 16E and 16F are microscope generated images of interphase nuclei and metaphase spreads treated to determine the IGH gene.

Example 14: Detection of Translocation of the IGH Gene Using Suppression of Undesired Background with the PNA Oligomer Mixture The PNA Oligomer Mixture was used to suppress the undesired background staining from IGH probes when used on normal metaphase spreads and interphase nuclei. The probes were labeled with fluorescein for the IGHV genes and with Texas Red for the IGHC genes (Poulsen T S, Silahtaroglu A N, Gisselo C G, Gaarsdal E, Rasmussen T, Tommerup N, Johnsen H E. Detection of illegitimate rearrangement within the immunoglobulin locus on 14q32.3 in B-cell malignancies using end-sequenced probes. (2001) Genes Chromosomes Cancer, 32: 265-74), mixed with either the PNA Oligomer Mixture (FIG. 16A) or Cot-1 DNA (FIG. 16B). The IGH probes were prepared as described in Example 11. In-situ hybridization was performed essentially as described in Example 11. However, in this Example 14, the pre-treatment was omitted and hybridization time was lowered to 4 hours, thus showing the robustness of the assay.

The DNA probes were mixed with either the PNA Oligomer Mixture (FIG. 16A) or Cot-1 DNA (FIG. 16B). For comparison FIG. 16C shows the result of performing the same assay in the absence of blocking agent.

The IGH genes are located on chromosome band 14q32. FIG. 16A shows normal IGH configurations on metaphases with a yellow signal located on both chromosome 14, band q32. FIG. 16B shows the result when background is suppressed using Cot-1 DNA. FIG. 16C shows the result of performing the assay in the absence of a blocking agent. It is not possible to identify the red or the green signals in the interphase nuclei and metaphase spread in the absence of a blocking agent.

The IGH probes were also hybridized to metaphase spreads of the cell line Granta 519 (Drexler, H. G. (2001) The Leukemia-Lymphoma Cell Line Facts Book. Braunschweig, Germany) that harbors a translocation t(11;14)(q23,q32). The IGH probes were labeled as above and mixed with either the PNA Oligomer Mixture (FIG. 16D) or Cot-1 DNA (FIG. 16E). FIG. 16D and FIG. 16E shows one yellow signal located on 14q32, indicating a normal IGH configuration on one allele and a split of the IGHV and IGHC probes on the other allele. This result is indicative of a translocation. For comparison FIG. 16F shows the same experiment without any blocking agent added.

Example 15: Detection of Translocation of the IGL Gene Using Suppression of Undesired Background with the PNA Oligomer Mixture The PNA Oligomer Mixture was used to suppress the undesired background staining from IGL probes when used on normal metaphase spreads and interphase nuclei. The probes were labeled with fluorescein for the IGLV genes and with Texas Red for the IGLC genes (Poulsen T S, Silahtaroglu A N, Gisselo C G, Gaarsdal E, Tommerup N, Johnsen H E. Detection of illegitimate rearrangements within the immunoglobulin light chain loci in B-cell malignancies using end sequenced probes. (2002) Leukemia, 16: 2148-2158), mixed with either the PNA Oligomer Mixture (FIG. 17A) or Cot-1 DNA (FIG. 17B). The IGL probes were prepared essentially as described in Example 11. The procedure for performing in-situ hybridization was performed essentially as described in Example 11. However, the hybridization time was lowered to 4 hours, thus showing the robustness of the assay.

The DNA probes were mixed with either the PNA Oligomer Mixture (FIG. 17A) or Cot-1 DNA (FIG. 17B). For comparison FIG. 17C shows the result of performing the same assay in the absence of blocking agent.

The IGL genes are located on chromosome band 22q11. FIG. 17A show normal IGL configurations on metaphases with a yellow signal located on both chromosome 22, band q11. FIG. 17B shows the result of the assay when Cot-1 DNA is used. FIG. 17C shows the result of performing the assay in the absence of a blocking agent. It is not possible to identify the red or the green signals in the interphase nuclei and metaphase spread in the absence of a blocking agent.

Example 16: Detection of Translocation of the IGK Gene Using Suppression of Undesired Background with the PNA Oligomer Mixture The PNA Oligomer Mixture was used to suppress the undesired background staining from IGL probes when used on normal metaphase spreads and interphase nuclei. The probes were labeled with fluorescein for the IGKV genes and with Texas Red for the IGKC genes (Poulsen T S, Silahtaroglu A N, Gisselo C G, Gaarsdal E, Tommerup N, Johnsen H E. Detection of illegitimate rearrangements within the immunoglobulin light chain loci in B-cell malignancies using end sequenced probes. (2002) Leukemia, 16: 2148-2158). The IGK genes are located on chromosome band 2p11. The IGK DNA probes were prepared essentially as described in Example 11. In-situ hybridization was performed essentially as described in Example 11, provided however, that the hybridization time was lowered to 4 hours, thus showing the robustness of the assay.

Figure 18:
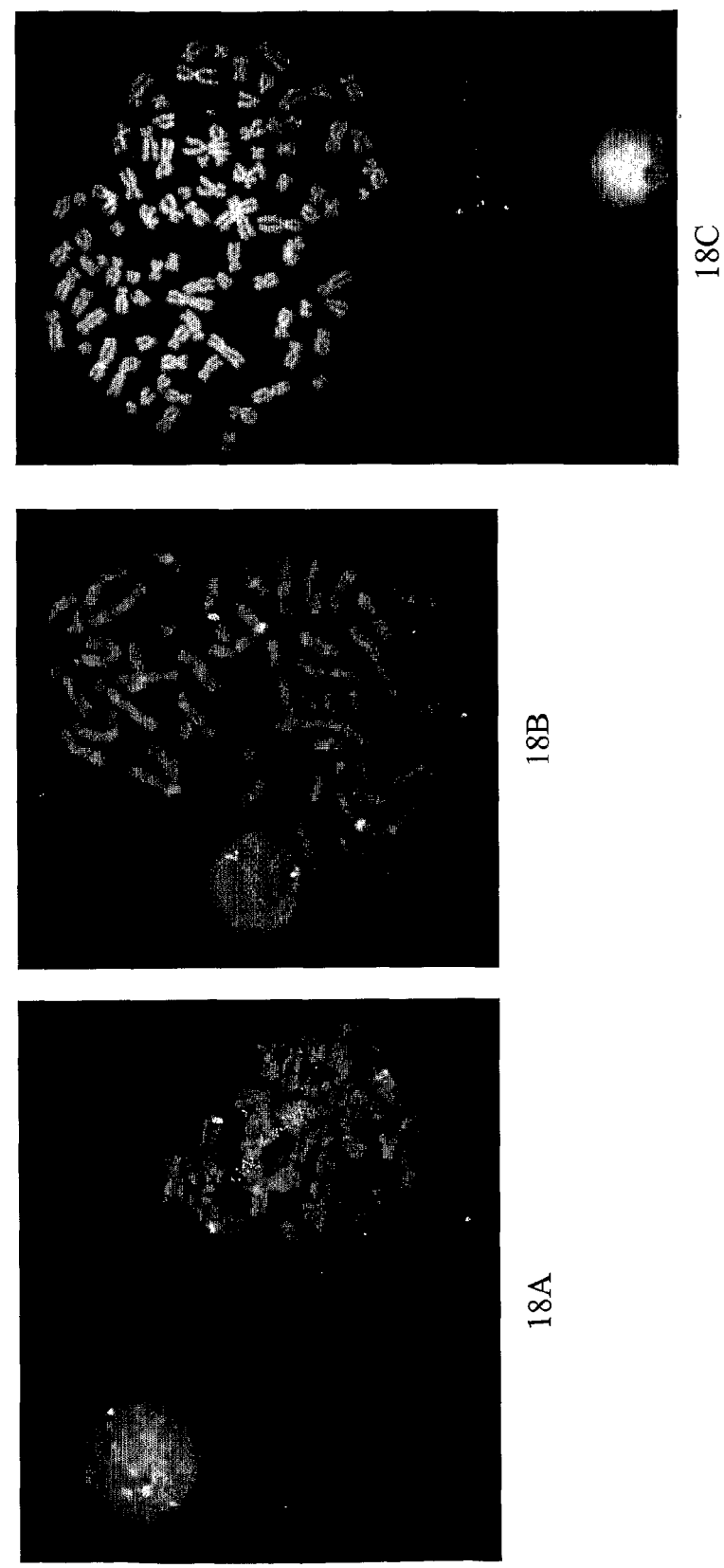
FIGS. 18A, 18B and 18C are microscope generated images of interphase nuclei and metaphase spreads treated to determine the IGK gene.

The DNA probes were mixed with either the PNA Oligomer Mixture (FIG. 18A) or Cot-1 DNA (FIG. 18B). For comparison, FIG. 18C shows the result of performing the assay in the absence of any blocking agent. FIG. 18A show normal IGK configurations on metaphases with a yellow signal located on both chromosome 2, band p11. FIG. 18B show the same probes suppressed with Cot-1 DNA. FIG. 18C show the same probes without any blocking agent added. It is not possible to identify neither the red nor the green signals in the interphase nuclei and metaphase spread.

Summary of Experimental Section

The aforementioned Examples 1-16, when taken together, demonstrate the utility of both the method for production of the PNA Oligomer Mixture as well as for use in suppressing the binding of detectable nucleic acid probes to randomly distributed repeat sequence in genomic nucleic acid.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

REFERENCES

Ausubel F M, Brent R, Kingston R E, Moore D D, Seidman J G, Smith J A, Struhl K. 1996. Current Protocols in Molecular Biology. John Wiley & Sons, Inc., Canada.

Baldini A, Ward D C. 1991. In situ hybridization banding of human chromosomes with Alu-PCR products: a simultaneous karyotype for gene mapping studies. Genomics 9(4):770-774.

Batzer M A, Deininger P L, Hellmann-Blumberg U, Jurka J, Labuda D, Rubin C M, Schmid C W, Zi•tkiewicz E, Zuckerkandl E. 1996. Standardized Nomenclature for Alu Repeats. J Mol Evol 42:3-6.

Boffa C L, Carpaneto E M, Allfrey V G. 1995, Isolation of active genes containing CAG repeats by DNA strand invasion by a peptide nucleic acid. Proc. Nat'l Acad. Sci. USA 92: 1901-1905

Britten R J. 1994. Evidence that most human Alu sequences were inserted in a process that ceased about 30 million years ago. Proc Natl Acad Sci USA 91:6148-6150.

Britten R J, Graham D E, Neufeld B R. 1986. Analysis of repeating DNA sequences by reassociation. Methods Enzymol 29: 363-418.

Britten R J, Kohne D E. 1968. Repeated Sequences in DNA. Hundreds of thousands of copies of DNA sequences have been incorporated into the genomes of higher organisms. Science 161(3841):529-540.

Brosius J. 1991. Retroposons—Seeds of Evolution. Science 251:753.

Choo, K. H. A: The centromere, Oxford University Press (1997) pp. 98-111

Claverie J-M, Makalowski W. 1994. Alu alert. Nature 371: 752.

Dunham I, Shimizu N, Roe B A, Chissoe S, et al. 1999. The DNA sequence of human chromosome 22. Nature 402: 489-495.

Eils R, Uhrig S, Saracoglu K, Sätzler K, Bolzer A, Petersen I, Chassery J-M, Ganser M, Speicher M R. 1998. An optimized, fully automated system for fast and accurate identification of chromosomal rearrangements by multiplex-FISH (M-FISH). Cytogenetics Cell Genet 82: 160-171.

Just T, Burgwald H, Broe M K. 1998. Flow cytometric detection of EBV (EBER snRNA) using peptide nucleic acid probes. J Vir Methods 73: 163-174.

Hattori M, Fujiyama A, Taylor T D et al. 2000. The DNA sequence of human chromosome 21. Nature 405:311-319.

Korenberg J R, Rykowski M C. 1988. Human Genome Organization: Alu, Lines, and the Molecular Structure of Metaphase Chromosome Bands. Cell 53:391-400.

Landegent J E, Jansen in de Wal N, Dirks R W, Baas F, van der Ploeg M. 1987. Use of whole cosmid cloned genomic sequences for chromosomal localization by non-radioactive in situ hybridization. Hum Genet 77:366-370.

Landegent J E, Jansen in de Wal N, van Ommen G-J B, Baas F, de Vijlder J J M, van Duijn P, van der Ploeg M. 1985. Chromosomal localization of a unique gene by non-autoradiographic in situ hybridization. Nature 317:175-177.

Macville M, Veldman T Padilla-Nash H, Wangsa D, O'Brien P, Schröck E, Ried T. 1997. Spectral karyotyping, a 24-colour FISH technique for the identification of chromosomal rearrangements. Histochem Cell Biol 108: 299-305.

Mighell A J, Markham A F, Robinson P A. 1997. Alu sequences. FEBS Letters 417:1-5.
Novick G E, Batzer M A, Deininger P L, Herrera R J. 1996. The Mobile Genetic Element Alu in the Human Genome. BioScience 46(1):32-41.
Rogers J H. 1985. The origin and evolution of retroposons. Int Rev Cyt 93:187-279.
Singer M F. 1982. SINEs and LINEs: Highly repeated short and long interspersed sequences in mammalian genomes. Cell 28: 433-434.
Sherry S T, Harpending H C, Batzer M A, Stoneking M. 1997. Alu Evolution in Human Populations: Using the Coalescent to Estimate Effective Population Size. Genetics 147:1977-1982.
Taneja K L. 1998. Localization Of Trinucleotide Repeat Sequences In Myotonic Dystrophy Cells Using A Single Fluorophore-Labeled PNA Probe. BioTechniques 24: 472-476.
Thisted M, Just T, Pluzek K-J, Hyldig-Nielsen J J, Godtfredsen S E. 1996. Detection of immunoglobulin kappa light chain mRNA in paraffin sections by in situ hybridization using peptide nucleic acid probes. Cell Vision 3: 358-363.
Tkachuk D C, Westbrook C A, Andreeff M, Donlon T A, Cleary M L, Suryanarayan K, Homge M, Redner A, Gray J, Pinkel D. 1990. Detection of bcr-abl fusion in chronic myelogenous leukaemia by in situ hybridisation. Science 250: 559-62.
Ullu E. June 1982. The human Alu family of repeated DNA sequences. TIBS 216-219.
van der Burg M, Beverloo H B, Langerak A W, Wijsman J, van Drunen E, Slater R, van Dongen J J M. 1999, Rapid and sensitive detection of all types of MLL gene translocations with a single FISH probe set. Leukemia 13: 2107-2113.

We claim:

1. A method for suppressing the binding of one or more detectable nucleic acid probes to one or more undesired sequences in an assay for determining target genomic nucleic acid of a sample; said method comprising:
   a) contacting the sample with a mixture of two or more different non-nucleotide probes wherein each probe is 16 to 50 nucleobases in length and each probe comprises a nucleobase sequence identical to one of the nucleobase sequences of the group consisting of: Seq. Id. No. 3, Seq. Id. No. 4, Seq. Id. No. 5, Seq. Id. No. 6, Seq. Id. No. 7, Seq. Id. No. 8, Seq. Id. No. 9, Seq. Id. No. 10, Seq. Id. No. 11, Seq. Id. No. 12, Seq. Id. No. 13, and the complement thereof, wherein the mixture of non-nucleotide probes further comprises at least one probe comprising a nucleobase sequence selected from TT(k)TTTTT(k)TTTLysOLysOTTT(k)TTTTT(k)TT and AA(k)AAAAA(k)AAALysOLysOAAA(k)AAAAA(k)AA, wherein (k) is a D-lysine, Lys is L-lysine, and O is 8-amino-3,6-dioxaoctanoic acid;
   b) contacting the sample with the one or more detectable nucleic acid probes, wherein said one or more detectable nucleic acid probes is 100 bp or greater, is derived from a genomic nucleic acid, and contains one or more segments of randomly distributed repeat sequence selected from the group consisting of SINEs and LINEs; and
   c) determining the target genomic nucleic acid of the sample by determining the hybridization of the one or more detectable nucleic acid probes to the target genomic nucleic acid of the sample.

2. The method of claim 1, wherein the two or more non-nucleotide probes are peptide nucleic acid (PNA) oligomers.

3. The method of claim 2, wherein the PNA subunits of the individual PNA oligomers have the formula:

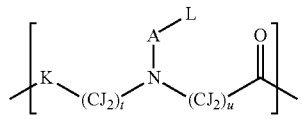

wherein, each J is the same or different and is selected from the group consisting of: H, $R^1$, $OR^1$, $SR^1$, $NHR^1$, $NR^1_2$, F, Cl, Br and I;

each K is the same or different and is selected from the group consisting of: O, S, NH and $NR^1$;

each $R^1$ is the same or different and is an alkyl group having one to five carbon atoms which may optionally contain a heteroatom or a substituted or unsubstituted aryl group;

each A is selected from the group consisting of a single bond, a group of the formula: $-(CJ_2)_s-$ and a group of the formula; $-(CJ_2)_sC(O)-$ wherein, J is defined above and each s is an integer from one to five;

each t is 1 or 2;

each u is 1 or 2; and each L is the same or different and is independently selected from the group consisting of J, dabcyl, fluorescein, adenine, cytosine, guanine, thymine, uracil, 5-propynyl-uracil, 2-thio-5-propynyl-uracil, 5-methylcytosine, 2-aminopurine, 2-amino-6-chloropurine, 2,6-diaminopurine, hypoxanthine, pseudoisocytosine, 2-thiouracil, 2-thiothymidine, N9-(2-amino-6-chloropurine), N9-(2,6-diaminopurine), N9-(7-deaza-guanine), N9-(7-deaza-8-aza-guanine) and N8-(7-deaza-8-aza-adenine), other naturally occurring nucleobase analogs, other non-naturally occurring nucleobases and substituted and unsubstituted aromatic moieties.

4. The method of claim 3, wherein the PNA subunits of the individual PNA probes consist of a naturally or non-naturally occurring nucleobase attached to an aza nitrogen of an N-[2-(aminoethyl)]glycine backbone through a methylene carbonyl linkage.

5. The method of claim 1, wherein the mixture comprises 5 to about 50 different non-nucleotide probes.

6. The method of claim 5, wherein the mixture comprises about 10 to about 25 different probes.

7. The method of claim 1, wherein the one or more detectable nucleic acid probes(s) is labeled with a fluorophore.

* * * * *

```
                         SEQUENCE LISTING

<160> NUMBER OF SEQ ID NOS: 72

<210> SEQ ID NO 1
    <211> LENGTH: 301
    <212> TYPE: DNA
    <213> ORGANISM: Artificial Sequence
    <220> FEATURE:
    <223> OTHER INFORMATION: Alu-repeat consensus sequence.

<400> SEQUENCE: 1
ggcgggcgga ggccgggcgc ggtggctcac gcctgtaatc ccagcacttt gggaggccga    60
ggcgggcgga tcacctgagg tcaggagttc gagaccagcc tggccaacat ggtgaaaccc   120
cgtctctact aaaaatacaa aaattagccg ggcgtggtgg cgcgcgcctg tartcccagc   180
tactcgggag gctgaggcag gagaatcgct tgaacccggg aggcggaggt tgcagtgagc   240
cgagatcgcg ccactgcact ccagcctggg cracaagagc garactccgt ctcaaaaaaa   300
a                                                                  301

<210> SEQ ID NO 2
    <211> LENGTH: 301
    <212> TYPE: DNA
    <213> ORGANISM: Artificial Sequence
    <220> FEATURE:
    <223> OTHER INFORMATION: Combined DNA/RNA sequence; Alu-repeat consensus
          sequence.

<400> SEQUENCE: 2
ttttttttga dacggagtyt cgctcttgty gcccaggctg gagtgcagtg gcgcgatctc    60
ggctcactgc aacctccgcc tcccgggttc aagcgattct cctgcctcag cctcccgagt   120
agctgggayt acaggcgcgc gccaccacgc ccggctaatt tttgtatttt tagtagagac   180
ggggtttcac catgttggcc aggctggtct cgaactcctg acctcaggtg atccgcccgc   240
ctcggcctcc caaagtgctg ggattacagg cgtgagccac cgcgcccggc ctccgcccgc   300
c                                                                  301

<210> SEQ ID NO 3
    <211> LENGTH: 17
    <212> TYPE: DNA
    <213> ORGANISM: Artificial Sequence
    <220> FEATURE:
    <223> OTHER INFORMATION: Peptide nucleic acid probe can be labeled
          and/or modified as follows: 1) N-terminally labeled with
          Lys(Flu); 2) modified with EE at both the N- and
``` the C-termini;
<220> FEATURE:
<223> OTHER INFORMATION: 3) N-terminally labeled and modified with
Flu-OEE and C-terminally modified with EE; or 4)
N-terminally labeled and modified with FluOLysLys
and C-terminally modified with LysLys;
<220> FEATURE:
<223> OTHER INFORMATION: wherein Lys = the amino acid L-lysine, Flu =
5(6)-carboxyfluorescein, E = the modification
resulting from use of compound 4 as described in
Gildea et al., Tett. Lett. 39:7255-7258 (1998),
<220> FEATURE:
<223> OTHER INFORMATION: and O = 8-amino-3,6-dioxaoctanoic acid.

<400> SEQUENCE: 3
ggccgggcgc ggtggct                                                  17

<210> SEQ ID NO 4
<211> LENGTH: 18
<212> TYPE: DNA
<213> ORGANISM: Artificial Sequence
<220> FEATURE:
<223> OTHER INFORMATION: Peptide nucleic acid probe can be labeled
and/or modified as follows: 1) N-terminally labeled with
Lys(Flu); 2) modified with Lys-Lys at both the N-
and the C-termini;
<220> FEATURE:
<223> OTHER INFORMATION: 3) modified with EE at both the N- and the
C-termini; or 4) N-terminally labeled and modified
with Flu-OEE and C-terminally modified with EE;
<220> FEATURE:
<223> OTHER INFORMATION: wherein Lys = the amino acid L-lysine, Flu =
5(6)-carboxyfluorescein, E = the modification
resulting from use of compound 4 as described in
Gildea et al., Tett. Lett. 39:7255-7258 (1998),
<220> FEATURE:
<223> OTHER INFORMATION: and O = 8-amino-3,6-dioxaoctanoic acid.

<400> SEQUENCE: 4
gctgggatta caggcgtg                                                 18

<210> SEQ ID NO 5
<211> LENGTH: 16
<212> TYPE: DNA
<213> ORGANISM: Artificial Sequence
<220> FEATURE:
<223> OTHER INFORMATION: Peptide nucleic acid probe can be labeled
and/or modified as follows: 1) N-terminally labeled and
modified with Flu-O; 2) N-terminally labeled and
modified with FluOLysLys
<220> FEATURE:
<223> OTHER INFORMATION: and C-terminally modified with LysLys; 3)
modified with EE at both the N- and the C-termini; or 4)
N-terminally labeled and modified with Flu-OEE
<220> FEATURE:
<223> OTHER INFORMATION: and C-terminally modified with EE; wherein
Flu = 5(6)-carboxyfluorescein, O = 8-amino-3,6-dioxaoctanoic acid,
Lys = the amino acid L-lysine,
<220> FEATURE:
<223> OTHER INFORMATION: and E = the modification resulting from use of
compound 4 as described in Gildea et al., Tett.
Lett. 39:7255-7258 (1998).

<400> SEQUENCE: 5
gggaggccga ggcggg                                                   16

<210> SEQ ID NO 6
<211> LENGTH: 21
<212> TYPE: DNA
<213> ORGANISM: Artificial Sequence
<220> FEATURE:
<223> OTHER INFORMATION: Peptide nucleic acid probe can be labeled
and/or modified as follows: 1) N-terminally labeled and modified with Lys(Flu); 2) modified with Lys-Lys
        at both the N- and the C-termini;
<220> FEATURE:
<223> OTHER INFORMATION: 3) modified with EE at both the N- and the
        C-termini; or 4) N-terminally labeled and modified
        with Flu-OEE and C-terminally modified with EE;
<220> FEATURE:
<223> OTHER INFORMATION: wherein Lys = the amino acid L-lysine, Flu =
        5(6)-carboxyfluorescein, E = the modification
        resulting from use of compound 4 as described in
        Gildea et al., Tett. Lett. 39:7255-7258 (1998),
<220> FEATURE:
<223> OTHER INFORMATION: and O = 8-amino-3,6-dioxaoctanoic acid.

<400> SEQUENCE: 6
gccaggctgg tctcgaactc c                                              21

<210> SEQ ID NO 7
<211> LENGTH: 21
<212> TYPE: DNA
<213> ORGANISM: Artificial Sequence
<220> FEATURE:
<223> OTHER INFORMATION: Peptide nucleic acid probe can be labeled
        and/or modified as follows: 1) N-terminally labeled and
        modified with Lys(Flu); 2) modified with Lys at
        both the N- and the C-termini;
<220> FEATURE:
<223> OTHER INFORMATION: 3) modified with Lys-Lys at both the N- and the
        C-termini; 4) modified with EE at both the N- and
        the C-termini; or 5) N-terminally labeled and
        modified with Flu-OEE
<220> FEATURE:
<223> OTHER INFORMATION: and C-terminally modified with EE; wherein
        Lys = the amino acid L-lysine, Flu = 5(6)-carboxyfluorescein, E =
        the modification resulting from use of compound 4
<220> FEATURE:
<223> OTHER INFORMATION: as described in Gildea et al., Tett. Lett.
        39:7255-7258 (1998), and O =
        8-amino-3,6-dioxaoctanoic acid.

<400> SEQUENCE: 7
gaaaccccgt ctctactaaa a                                              21

<210> SEQ ID NO 8
<211> LENGTH: 16
<212> TYPE: DNA
<213> ORGANISM: Artificial Sequence
<220> FEATURE:
<223> OTHER INFORMATION: Peptide nucleic acid probe can be labeled
        and/or modified as follows: 1) N-terminally labeled and
        modified with Lys(Flu); 2) modified with EE at
        both the N- and the C-termini;
<220> FEATURE:
<223> OTHER INFORMATION: 3) N-terminally labeled and modified with
        Flu-OEE and C-terminally modified with EE; or 4)
        N-terminally labeled and modified with FluOLysLys
<220> FEATURE:
<223> OTHER INFORMATION: and C-terminally modified with LysLys; wherein
        Lys = the amino acid L-lysine, Flu = 5(6)-carboxyfluorescein, E =
        the modification resulting from use of compound 4
<220> FEATURE:
<223> OTHER INFORMATION: as described in Gildea et al., Tett. Lett.
        39:7255-7258 (1998), and O =
        8-amino-3,6-dioxaoctanoic acid.

<400> SEQUENCE: 8
gccgggcgtg gtggcg                                                    16

<210> SEQ ID NO 9
<211> LENGTH: 18
<212> TYPE: DNA
<213> ORGANISM: Artificial Sequence
<220> FEATURE:

```
<223> OTHER INFORMATION: Peptide nucleic acid probe can be labeled
      and/or modified as follows: 1) C-terminally modified with
      Lys; 2) N-terminally labeled and modified with
      Lys(Flu) and C-terminally modified with Lys;
<220> FEATURE:
<223> OTHER INFORMATION: 3) modified with Lys-Lys at both the N- and the
      C-termini; 4) modified with EE at both the N- and
      the C-termini; or 5) N-terminally labeled and
      modified with Flu-OEE
<220> FEATURE:
<223> OTHER INFORMATION: and C-terminally modified with EE; wherein
      Lys = the amino acid L-lysine, Flu =
      5(6)-carboxyfluorescein, E = the modification
      resulting from use of compound 4
<220> FEATURE:
<223> OTHER INFORMATION: as described in Gildea et al., Tett. Lett.
      39:7255-7258 (1998), and O =
      8-amino-3,6-dioxaoctanoic acid.

<400> SEQUENCE: 9
tagctgggat tacaggcg                                                  18

<210> SEQ ID NO 10
<211> LENGTH: 17
<212> TYPE: DNA
<213> ORGANISM: Artificial Sequence
<220> FEATURE:
<223> OTHER INFORMATION: Peptide nucleic acid probe can be labeled
      and/or modified as follows: 1) C-terminally modified with
      Lys; 2) N-terminally labeled and modified with
      Lys(Flu) and C-terminally modified with Lys;
<220> FEATURE:
<223> OTHER INFORMATION: 3) modified with Lys-Lys at both the N- and the
      C-termini; 4) modified with EE at both the N- and
      the C-termini; or 5) N-terminally labeled and
      modified with Flu-OEE
<220> FEATURE:
<223> OTHER INFORMATION: and C-terminally modified with EE; wherein
      Lys = the amino acid L-lysine, Flu = 5(6)-carboxyfluorescein, E =
      the modification resulting from use of compound 4
<220> FEATURE:
<223> OTHER INFORMATION: as described in Gildea et al., Tett. Lett.
      39:7255-7258 (1998), and O =
      8-amino-3,6-dioxaoctanoic acid.

<400> SEQUENCE: 10
gggaggctga ggcagga                                                   17

<210> SEQ ID NO 11
<211> LENGTH: 21
<212> TYPE: DNA
<213> ORGANISM: Artificial Sequence
<220> FEATURE:
<223> OTHER INFORMATION: Peptide nucleic acid probe can be labeled
      and/or modified as follows: 1) C-terminally modified with
      Lys; 2) N-terminally labeled and modified with
      Lys(Flu) and C-terminally modified with Lys;
<220> FEATURE:
<223> OTHER INFORMATION: 3) modified with EE at both the N- and the
      C-termini; 4) N-terminally labeled and modified
      with Flu-OEE and C-terminally modified with EE; or
      5) N-terminally labeled
<220> FEATURE:
<223> OTHER INFORMATION: and modified with FluOLysLys and C-terminally
      modified with LysLys; wherein Lys =  the amino
      acid L-lysine, Flu = 5(6)-carboxyfluorescein, E =
      the modification resulting from use of compound 4
<220> FEATURE:
<223> OTHER INFORMATION: as described in Gildea et al., Tett. Lett.
      39:7255-7258 (1998), and O =
      8-amino-3,6-dioxaoctanoic acid.

<400> SEQUENCE: 11
cctcccgggt tcaagcgatt c                                              21
```

<210> SEQ ID NO 12
<211> LENGTH: 17
<212> TYPE: DNA
<213> ORGANISM: Artificial Sequence
<220> FEATURE:
<223> OTHER INFORMATION: Peptide nucleic acid probe can be labeled
      and/or modified as follows: 1) N-terminally labeled
      and/or modified with Lys or Lys(Flu); 2)
      N-terminally labeled and modified with FluOLysLys
<220> FEATURE:
<223> OTHER INFORMATION: and C-terminally modified with LysLys; 3)
      modified with EE at both the N- and the C-termini; 4)
      N-terminally labeled and modified with Flu-OEE
<220> FEATURE:
<223> OTHER INFORMATION: and C-terminally modified with EE; 5)
      N-terminally labeled and modified with Flu-OPP and C-terminally
      modified with PP; 6) N-terminally labeled and
      modified with Flu-OOO
<220> FEATURE:
<223> OTHER INFORMATION: and C-terminally modified with OO; or 7)
      N-terminally labeled and modified with Flu-OGluGlu
      and C-terminally modified with GluGlu;
<220> FEATURE:
<223> OTHER INFORMATION: wherein Lys = the amino acid L-lysine, Flu =
      5(6)-carboxyfluorescein, O = 8-amino-3,6-dioxaoctanoic acid, E =
      the modification resulting from use of compound 4
<220> FEATURE:
<223> OTHER INFORMATION: as described in Gildea et al., Tett. Lett.
      39:7255-7258 (1998), P = the product of using
      piperazine-N,N' diacetic
      acid-mono(2-Boc-aminoethylamide)
<220> FEATURE:
<223> OTHER INFORMATION: as a monomer, and Glu = the amino acid glutamic
      acid.

<400> SEQUENCE: 12
ttgcagtgag ccgagat                                                    17

<210> SEQ ID NO 13
<211> LENGTH: 21
<212> TYPE: DNA
<213> ORGANISM: Artificial Sequence
<220> FEATURE:
<223> OTHER INFORMATION: Peptide nucleic acid probe can be labeled
      and/or modified as follows: 1) N-terminally labeled and
      modified with Lys(Flu); 2) modified with Lys-Lys
      at both the N- and the C-termini;
<220> FEATURE:
<223> OTHER INFORMATION: 3) modified with EE at both the N- and the
      C-termini; or 4) N-terminally labeled and modified
      with Flu-OEE and C-terminally modified with EE;
<220> FEATURE:
<223> OTHER INFORMATION: wherein Lys = the amino acid L-lysine, Flu =
      5(6)-carboxyfluorescein, E = the modification
      resulting from use of compound 4 as described in
      Gildea et al., Tett. Lett. 39:7255-7258 (1998),
<220> FEATURE:
<223> OTHER INFORMATION: and O = 8-amino-3,6-dioxaoctanoic acid.

<400> SEQUENCE: 13
tgcactccag cctgggcgac a                                               21

<210> SEQ ID NO 14
<211> LENGTH: 20
<212> TYPE: DNA
<213> ORGANISM: Artificial Sequence
<220> FEATURE:
<223> OTHER INFORMATION: Peptide nucleic acid probe has the sequence
      TTkTTTTTkTTTLysOLysOTTTkTTTTTkTT, which is
      C-terminally modified with Lys and N-terminally
      labeled and/or modified with Lys
<220> FEATURE:
<223> OTHER INFORMATION: or FluOLys, or the sequence

```
      TTkTTTTTkTTTOOOTTTkTTTTTkTT, which is N-terminally
      labeled and modified with FluO,
<220> FEATURE:
<223> OTHER INFORMATION: wherein k = the amino acid D-lysine, Lys =
      the amino acid L-lysine, O = 8-amino-3,6-dioxaoctanoic
      acid, and Flu = 5(6)-carboxyfluorescein.

<400> SEQUENCE: 14
tttttttttt tttttttttt                                                      20

<210> SEQ ID NO 15
<211> LENGTH: 17
<212> TYPE: DNA
<213> ORGANISM: Artificial Sequence
<220> FEATURE:
<223> OTHER INFORMATION: Non-nucleotide probe.

<400> SEQUENCE: 15
agccaccgcg cccggcc                                                         17

<210> SEQ ID NO 16
<211> LENGTH: 18
<212> TYPE: DNA
<213> ORGANISM: Artificial Sequence
<220> FEATURE:
<223> OTHER INFORMATION: Non-nucleotide probe.

<400> SEQUENCE: 16
cacgcctgta atcccagc                                                        18

<210> SEQ ID NO 17
<211> LENGTH: 16
<212> TYPE: DNA
<213> ORGANISM: Artificial Sequence
<220> FEATURE:
<223> OTHER INFORMATION: Non-nucleotide probe.

<400> SEQUENCE: 17
cccgcctcgg cctccc                                                          16

<210> SEQ ID NO 18
<211> LENGTH: 21
<212> TYPE: DNA
<213> ORGANISM: Artificial Sequence
<220> FEATURE:
<223> OTHER INFORMATION: Non-nucleotide probe.

<400> SEQUENCE: 18
ggagttcgag accagcctgg c                                                    21

<210> SEQ ID NO 19
<211> LENGTH: 21
<212> TYPE: DNA
<213> ORGANISM: Artificial Sequence
<220> FEATURE:
<223> OTHER INFORMATION: Non-nucleotide probe.

<400> SEQUENCE: 19
ttttagtaga gacggggttt c                                                    21

<210> SEQ ID NO 20
<211> LENGTH: 16
<212> TYPE: DNA
<213> ORGANISM: Artificial Sequence
<220> FEATURE:
<223> OTHER INFORMATION: Non-nucleotide probe.
```

-continued

```
<400> SEQUENCE: 20
cgccaccacg cccggc                                                    16

<210> SEQ ID NO 21
<211> LENGTH: 18
<212> TYPE: DNA
<213> ORGANISM: Artificial Sequence
<220> FEATURE:
<223> OTHER INFORMATION: Non-nucleotide probe.

<400> SEQUENCE: 21
cgcctgtaat cccagcta                                                  18

<210> SEQ ID NO 22
<211> LENGTH: 17
<212> TYPE: DNA
<213> ORGANISM: Artificial Sequence
<220> FEATURE:
<223> OTHER INFORMATION: Non-nucleotide probe.

<400> SEQUENCE: 22
tcctgcctca gcctccc                                                   17

<210> SEQ ID NO 23
<211> LENGTH: 21
<212> TYPE: DNA
<213> ORGANISM: Artificial Sequence
<220> FEATURE:
<223> OTHER INFORMATION: Non-nucleotide probe.

<400> SEQUENCE: 23
gaatcgcttg aacccgggag g                                              21

<210> SEQ ID NO 24
<211> LENGTH: 17
<212> TYPE: DNA
<213> ORGANISM: Artificial Sequence
<220> FEATURE:
<223> OTHER INFORMATION: Non-nucleotide probe.

<400> SEQUENCE: 24
atctcggctc actgcaa                                                   17

<210> SEQ ID NO 25
<211> LENGTH: 21
<212> TYPE: DNA
<213> ORGANISM: Artificial Sequence
<220> FEATURE:
<223> OTHER INFORMATION: Non-nucleotide probe.

<400> SEQUENCE: 25
tgtcgcccag gctggagtgc a                                              21

<210> SEQ ID NO 26
<211> LENGTH: 20
<212> TYPE: DNA
<213> ORGANISM: Artificial Sequence
<220> FEATURE:
<223> OTHER INFORMATION: Peptide nucleic acid probe has the sequence
      AAkAAAAAkAAALysOLysOAAAkAAAAAkAA, wherein k = the
      amino acid D-lysine, Lys =  the amino acid
      L-lysine, and O = 8-amino-3,6-dioxaoctanoic acid.

<400> SEQUENCE: 26
aaaaaaaaaa aaaaaaaaaa                                                20
```

```
<210> SEQ ID NO 27
<211> LENGTH: 21
<212> TYPE: DNA
<213> ORGANISM: Artificial Sequence
<220> FEATURE:
<223> OTHER INFORMATION: Peptide nucleic acid probe can be N-terminally
      labeled and modified with Lys(Flu), wherein Lys =
      the amino acid L-lysine, and Flu = 5(6)-carboxyfluorescein.

<400> SEQUENCE: 27
gccaggatgg tctcgatctc c                                              21

<210> SEQ ID NO 28
<211> LENGTH: 21
<212> TYPE: DNA
<213> ORGANISM: Artificial Sequence
<220> FEATURE:
<223> OTHER INFORMATION: PNA probe sequence.

<400> SEQUENCE: 28
cctcccgggt tcacgcgatt c                                              21

<210> SEQ ID NO 29
<211> LENGTH: 290
<212> TYPE: DNA
<213> ORGANISM: Homo sapiens
<220> FEATURE:
<223> OTHER INFORMATION: Majority (consensus) of human sequences
      HSU1457.seq Sx, HSU14573.seq Sq, HSU14572.seq Sp,
      HSU14571.seq Sc, and HSU 14567.seq J

<400> SEQUENCE: 29
ggccgggcgc ggtggctcac gcctgtaatc ccagcacttt gggaggccga ggcgggcgga    60
tcacctgagg tcaggagttc gagaccagcc tggccaacat ggtgaaaccc cgtctctact   120
aaaaatacaa aaattagccg ggcgtggtgg cgcgcgcctg taatcccagc tactcgggag   180
gctgaggcag gagaatcgct tgaacccggg aggcggaggt tgcagtgagc cgagatcgcg   240
ccactgcact ccagcctggg cgacagagcg agactccgtc tcaaaaaaaa              290

<210> SEQ ID NO 30
<211> LENGTH: 288
<212> TYPE: DNA
<213> ORGANISM: Homo sapiens

<400> SEQUENCE: 30
cgggcggagg ccgggcgcgg tggctcacgc ctgtaatccc agcactttgg gaggaagatc    60
acctgaggtc aggagttcga gaccagcctg gccaacatgg tgaaacccccg tctctactaa  120 aaatacaaaa attagccggg cgtggtggcg cgcgcctgta atcccagcta ctcgggaggc   180
tgaggcagga gaatcgcttg aacccgggag gcggaggttg cagtgagccg agatcgcgcc   240
actgcactcc agcctgggcg acagagcgag actccgtctc aaaaaaaa                288

<210> SEQ ID NO 31
<211> LENGTH: 291
<212> TYPE: DNA
<213> ORGANISM: Homo sapiens

<400> SEQUENCE: 31
ggccgggcgc ggtggctcac gcctgtaatc ccagcacttt gggaggccga ggcgggtgga    60
tcacctgagg tcaggagttc gagaccagcc tggccaacat ggtgaaaccc cgtctctact   120
aaaaatacaa aaattagccg ggcgtggtgg cgggcgcctg taatcccagc tactcgggag   180
```
gctgaggcag gagaatcgct tgaacccggg aggcggaggt tgcagtgagc cgagatcgcg    240
ccactgcact ccagcctggg caacaagagc gaaactccgt ctcaaaaaaa a            291

<210> SEQ ID NO 32
<211> LENGTH: 291
<212> TYPE: DNA
<213> ORGANISM: Homo sapiens

<400> SEQUENCE: 32 ggcgggcgc ggtggctcac gcctgtaatc ccagcacttt gggaggccga ggcgggcgga    60
tcacctgagg tcgggagttc gagaccagcc tgaccaacat ggagaaaccc cgtctctact   120
aaaaatacaa aaattagccg ggcgtggtgg cgcatgcctg taatcccagc tactcgggag   180
gctgaggcag gagaatcgct tgaacccggg aggcggaggt tgcggtgagc cgagatcgcg   240
ccattgcact ccagcctggg caacaagagc gaaactccgt ctcaaaaaaa a            291

<210> SEQ ID NO 33
<211> LENGTH: 287
<212> TYPE: DNA
<213> ORGANISM: Homo sapiens

<400> SEQUENCE: 33
ggccgggcgc ggtggctcac gcctgtaatc ccagcacttt gggaggccga ggcgggcgga   60
tcacgaggtc aagagatcga gaccatcctg gccaacatgg tgaaacccg tctctactaa    120 aaatacaaaa attagctggg cgtggtggcg cgcgcctgta gtcccagcta ctcgggaggc   180
tgaggcagga gaatcgcttg aacccgggag gcggaggttg cagtgagccg agatcgcgcc   240
actgcactcc agcctggcga cagagcgaga ctccgtctca aaaaaa                  287

<210> SEQ ID NO 34
<211> LENGTH: 290
<212> TYPE: DNA
<213> ORGANISM: Homo sapiens

<400> SEQUENCE: 34
ggccgggcgc ggtggctcac gcctgtaatc ccagcacttt gggaggccga ggcgggagga   60
tcacttgagc ccaggagttc gagaccagcc tgggcaacat agtgaaaccc cgtctctaca   120
aaaaatacaa aaattagccg ggcgtggtgg cgcgcgcctg tagtcccagc tactcggagg   180
gctgaggcag gaggatcgct tgagcccggg aggtcgaggc tgcagtgagc cgtgatcgcg   240
ccactgcact ccagcctggg cgacagagcg agaccctgtc tcaaaaaaaa              290

<210> SEQ ID NO 35
<211> LENGTH: 18
<212> TYPE: DNA
<213> ORGANISM: Artificial Sequence
<220> FEATURE:
<223> OTHER INFORMATION: Peptide nucleic acid probe can be N-terminally
      labeled and modified with Lys(Flu), wherein Lys =
      the amino acid L-lysine, and Flu = 5(6)-carboxyfluorescein.

<400> SEQUENCE: 35
caggccgggt gcagtggc                                                 18

<210> SEQ ID NO 36
<211> LENGTH: 15
<212> TYPE: DNA
<213> ORGANISM: Artificial Sequence
<220> FEATURE:

```
<223> OTHER INFORMATION: Combined DNA/RNA sequence;
<220> FEATURE:
<223> OTHER INFORMATION: Peptide nucleic acid probe is N-terminally
      labeled and/or modified with Bio-OEE, EE or Flu-OEE, and
      C-terminally modified with EE, wherein Bio =
      biotin, O = 8-amino-3,6-dioxaoctanoic acid,
<220> FEATURE:
<223> OTHER INFORMATION: E = the modification resulting from use of
      compound 4 as described in Gildea et al., Tett.
      Lett. 39:7255-7258 (1998), and Flu =
      5(6)-carboxyfluorescein.

<400> SEQUENCE: 36
gccgggcgyg gtggc                                              15

<210> SEQ ID NO 37
<211> LENGTH: 16
<212> TYPE: DNA
<213> ORGANISM: Artificial Sequence
<220> FEATURE:
<223> OTHER INFORMATION: Combined DNA/RNA sequence;
<220> FEATURE:
<223> OTHER INFORMATION: Peptide nucleic acid probe is N-terminally
      labeled and modified with Bio-OEE and C-terminally
      modified with EE, wherein Bio = biotin, O =
      8-amino-3,6-dioxaoctanoic acid,
<220> FEATURE:
<223> OTHER INFORMATION: and E = the modification resulting from use of
      compound 4 as described in Gildea et al., Tett.
      Lett. 39:7255-7258 (1998).

<400> SEQUENCE: 37
gctgggayta caggcg                                             16

<210> SEQ ID NO 38
<211> LENGTH: 17
<212> TYPE: DNA
<213> ORGANISM: Artificial Sequence
<220> FEATURE:
<223> OTHER INFORMATION: Peptide nucleic acid probe can be N-terminally
      labeled and modified with Lys(Flu), wherein Lys =
      the amino acid L-lysine, and Flu = 5(6)-carboxyfluorescein.

<400> SEQUENCE: 38
tgtaatccca gcacttt                                            17

<210> SEQ ID NO 39
<211> LENGTH: 15
<212> TYPE: DNA
<213> ORGANISM: Artificial Sequence
<220> FEATURE:
<223> OTHER INFORMATION: Peptide nucleic acid probe is N-terminally
      labeled and modified with Lys(Flu)-Lys(Flu), wherein Lys =
      the amino acid L-lysine, and Flu = 5(6)-carboxyfluorescein.

<400> SEQUENCE: 39
gcactttggg aggcc                                              15

<210> SEQ ID NO 40
<211> LENGTH: 15
<212> TYPE: DNA
<213> ORGANISM: Artificial Sequence
<220> FEATURE:
<223> OTHER INFORMATION: Peptide nucleic acid probe is N-terminally
      labeled and modified with Lys(Flu)-Lys(Flu), wherein Lys =
      the amino acid L-lysine, and Flu = 5(6)-carboxyfluorescein.

<400> SEQUENCE: 40
ggcctcccaa agtgc                                              15
```

<210> SEQ ID NO 41
<211> LENGTH: 12
<212> TYPE: DNA
<213> ORGANISM: Artificial Sequence
<220> FEATURE:
<223> OTHER INFORMATION: Peptide nucleic acid has the sequence
      CCTCCC-EOE-CCCTCC, which is N-terminally labeled
      and modified with Bio-OEE and C-terminally
      modified with EE,
<220> FEATURE:
<223> OTHER INFORMATION: wherein E = the modification resulting from use
      of compound 4 as described in Gildea et al., Tett.
      Lett. 39:7255-7258 (1998), O = 8-amino-3,6-dioxaoctanoic acid, and
      Bio = biotin.

<400> SEQUENCE: 41 cctccccct cc                                                          12

<210> SEQ ID NO 42
<211> LENGTH: 15
<212> TYPE: DNA
<213> ORGANISM: Artificial Sequence
<220> FEATURE:
<223> OTHER INFORMATION: Combined DNA/RNA sequence;
<220> FEATURE:
<223> OTHER INFORMATION: Peptide nucleic acid probe is N-terminally
      labeled and modified with Bio-OEE and C-terminally
      modified with EE, wherein Bio = biotin, O =
      8-amino-3,6-dioxaoctanoic acid,
<220> FEATURE:
<223> OTHER INFORMATION: and E = the modification resulting from use of
      compound 4 as described in Gildea et al., Tett.
      Lett. 39:7255-7258 (1998).

<400> SEQUENCE: 42
gggaggcyga ggcgg                                                      15

<210> SEQ ID NO 43
<211> LENGTH: 20
<212> TYPE: DNA
<213> ORGANISM: Artificial Sequence
<220> FEATURE:
<223> OTHER INFORMATION: Peptide nucleic acid probe can be N-terminally
      labeled and modified with Flu-Lys, wherein Flu =
      5(6)-carboxyfluorescein, and Lys = the amino acid
      L-lysine.

<400> SEQUENCE: 43
actttgggag gaagatcacc                                                 20

<210> SEQ ID NO 44
<211> LENGTH: 15
<212> TYPE: DNA
<213> ORGANISM: Artificial Sequence
<220> FEATURE:
<223> OTHER INFORMATION: Peptide nucleic acid probe can be N-terminally
      labeled and modified with Flu-OE and C-terminally
      modified with E, wherein Flu = 5(6)-carboxyfluorescein,
<220> FEATURE:
<223> OTHER INFORMATION: O = 8-amino-3,6-dioxaoctanoic acid, and E = the
      modification resulting from use of compound 4 as
      described in Gildea et al., Tett. Lett.
      39:7255-7258 (1998).

<400> SEQUENCE: 44
cacctgaggt cagga                                                      15

<210> SEQ ID NO 45
<211> LENGTH: 15
<212> TYPE: DNA

```
<213> ORGANISM: Artificial Sequence
<220> FEATURE:
<223> OTHER INFORMATION: Peptide nucleic acid probe can be N-terminally
      labeled and modified with Flu-OE and C-terminally
      modified with E, wherein Flu = 5(6)-carboxyfluorescein,
<220> FEATURE:
<223> OTHER INFORMATION: O = 8-amino-3,6-dioxaoctanoic acid, and E = the
      modification resulting from use of compound 4 as
      described in Gildea et al., Tett. Lett.
      39:7255-7258 (1998).

<400> SEQUENCE: 45
tggccaacat ggtga                                                          15

<210> SEQ ID NO 46
<211> LENGTH: 15
<212> TYPE: DNA
<213> ORGANISM: Artificial Sequence
<220> FEATURE:
<223> OTHER INFORMATION: Peptide nucleic acid probe can be N-terminally
      labeled and modified with Lys(Flu), wherein Lys =
      the amino acid L-lysine, and Flu = 5(6)-carboxyfluorescein.

<400> SEQUENCE: 46
gaggctgagg cagga                                                          15

<210> SEQ ID NO 47
<211> LENGTH: 21
<212> TYPE: DNA
<213> ORGANISM: Artificial Sequence
<220> FEATURE:
<223> OTHER INFORMATION: Peptide nucleic acid probe can be N-terminally
      labeled and modified with Lys(Flu), wherein Lys =
      the amino acid L-lysine, and Flu = 5(6)-carboxyfluorescein.

<400> SEQUENCE: 47
cctcccgggt tcacgccatt c                                                   21

<210> SEQ ID NO 48
<211> LENGTH: 17
<212> TYPE: DNA
<213> ORGANISM: Artificial Sequence
<220> FEATURE:
<223> OTHER INFORMATION: Combined DNA/RNA sequence;
<220> FEATURE:
<223> OTHER INFORMATION: Peptide nucleic acid probe is N-terminally
      labeled and modified with Lys(Flu) and C-terminally
      modified with Lys, wherein Lys = the amino acid
      L-lysine, and Flu = 5(6)-carboxyfluorescein.

<400> SEQUENCE: 48
ducucggcuc dcugcdd                                                        17

<210> SEQ ID NO 49
<211> LENGTH: 17
<212> TYPE: DNA
<213> ORGANISM: Artificial Sequence
<220> FEATURE:
<223> OTHER INFORMATION: Combined DNA/RNA sequence;
<220> FEATURE:
<223> OTHER INFORMATION: Peptide nucleic acid probe is N-terminally
      labeled and modified with Lys(Flu) and C-terminally
      modified with Lys, wherein Lys = the amino acid
      L-lysine, and Flu = 5(6)-carboxyfluorescein.

<400> SEQUENCE: 49
uugcdgugdg ccgdgdu                                                        17

<210> SEQ ID NO 50
```

```
<211> LENGTH: 25
<212> TYPE: DNA
<213> ORGANISM: Artificial Sequence
<220> FEATURE:
<223> OTHER INFORMATION: Peptide nucleic acid probe can be N-terminally
      labeled and modified with Lys(Flu), wherein Lys =
      the amino acid L-lysine, and Flu = 5(6)-carboxyfluorescein.

<400> SEQUENCE: 50
ccactgcact ccagcctggg cgaca                                              25

<210> SEQ ID NO 51
<211> LENGTH: 17
<212> TYPE: DNA
<213> ORGANISM: Artificial Sequence
<220> FEATURE:
<223> OTHER INFORMATION: Peptide nucleic acid probe is N-terminally
      labeled and/or modified with Lys or Lys(Flu), wherein Lys
      = the amino acid L-lysine, and Flu = 5(6)-carboxyfluorescein.

<400> SEQUENCE: 51
tgcactccag cctgggc                                                       17

<210> SEQ ID NO 52
<211> LENGTH: 18
<212> TYPE: DNA
<213> ORGANISM: Artificial Sequence
<220> FEATURE:
<223> OTHER INFORMATION: Peptide nucleic acid probe can be N-terminally
      labeled and modified with Lys(Flu), wherein Lys =
      the amino acid L-lysine, and Flu = 5(6)-carboxyfluorescein.

<400> SEQUENCE: 52
tttgagacag agtctcgc                                                      18

<210> SEQ ID NO 53
<211> LENGTH: 20
<212> TYPE: DNA
<213> ORGANISM: Artificial Sequence
<220> FEATURE:
<223> OTHER INFORMATION: Peptide nucleic acid probe is C-terminally
      modified with Lys and is optionally N-terminally
      labeled and modified with Lys(Flu),
<220> FEATURE:
<223> OTHER INFORMATION: wherein Lys = the amino acid L-lysine, and
      Flu = 5(6)-carboxyfluorescein.

<400> SEQUENCE: 53
tttgagacgg agtctcgctc                                                    20

<210> SEQ ID NO 54
<211> LENGTH: 14
<212> TYPE: DNA
<213> ORGANISM: Artificial Sequence
<220> FEATURE:
<223> OTHER INFORMATION: Peptide nucleic acid probe is C-terminally
      modified with Lys and has the sequence
      TTTTTTT-O-Lys-O-Lys-O-TTTTTTT,
<220> FEATURE:
<223> OTHER INFORMATION: which is N-terminally labeled and modified with
      FluLys(Flu)OO, or has the sequence
      TTkTTTTT-O-Lys-O-Lys-O-TTkTTTTT,
<220> FEATURE:
<223> OTHER INFORMATION: which is N-terminally labeled and modified with
      FluLysOO or FluLys(Flu)OO,
<220> FEATURE:
<223> OTHER INFORMATION: wherein Lys = the amino acid L-lysine, O =
      8-amino-3,6-dioxaoctanoic acid, Flu =
      5(6)-carboxyfluorescein, and k = the amino acid
      D-lysine.
```

```
<400> SEQUENCE: 54
tttttttttt tttt                                                    14

<210> SEQ ID NO 55
<211> LENGTH: 18
<212> TYPE: DNA
<213> ORGANISM: Artificial Sequence
<220> FEATURE:
<223> OTHER INFORMATION: Peptide nucleic acid probe is labeled and
      modified N-terminally with Flu-OEE and C-terminally with
      EEO-Lys(Flu)-NH2, wherein Flu = 5(6)-carboxyfluorescein,
<220> FEATURE:
<223> OTHER INFORMATION: O = 8-amino-3,6-dioxaoctanoic acid, E = the
      modification resulting from use of compound 4 as
      described in Gildea et al., Tett. Lett.
      39:7255-7258 (1998),
<220> FEATURE:
<223> OTHER INFORMATION: Lys = the amino acid L-lysine, and NH2 =
      amidation.

<400> SEQUENCE: 55
aacgaattat ggtcacat                                                18

<210> SEQ ID NO 56
<211> LENGTH: 18
<212> TYPE: DNA
<213> ORGANISM: Artificial Sequence
<220> FEATURE:
<223> OTHER INFORMATION: Peptide nucleic acid probe is labeled and
      modified N-terminally with Flu-OEE and C-terminally with
      EEO-Lys(Flu)-NH2, wherein Flu = 5(6)-carboxyfluorescein,
<220> FEATURE:
<223> OTHER INFORMATION: O = 8-amino-3,6-dioxaoctanoic acid, E = the
      modification resulting from use of compound 4 as
      described in Gildea et al., Tett. Lett.
      39:7255-7258 (1998),
<220> FEATURE:
<223> OTHER INFORMATION: Lys = the amino acid L-lysine, and NH2 =
      amidation.

<400> SEQUENCE: 56
ggtgacgact gagtttaa                                                18

<210> SEQ ID NO 57
<211> LENGTH: 18
<212> TYPE: DNA
<213> ORGANISM: Artificial Sequence
<220> FEATURE:
<223> OTHER INFORMATION: Peptide nucleic acid probe is labeled and
      modified N-terminally with Flu-OEE and C-terminally with
      EEO-Lys(Flu)-NH2, wherein Flu = 5(6)-carboxyfluorescein,
<220> FEATURE:
<223> OTHER INFORMATION: O = 8-amino-3,6-dioxaoctanoic acid, E = the
      modification resulting from use of compound 4 as
      described in Gildea et al., Tett. Lett.
      39:7255-7258 (1998),
<220> FEATURE:
<223> OTHER INFORMATION: Lys = the amino acid L-lysine, and NH2 =
      amidation.

<400> SEQUENCE: 57
aacgggataa ctgcacct                                                18

<210> SEQ ID NO 58
<211> LENGTH: 18
<212> TYPE: DNA
<213> ORGANISM: Artificial Sequence
<220> FEATURE:
<223> OTHER INFORMATION: Peptide nucleic acid probe is labeled and
      modified N-terminally with Flu-OEE and C-terminally with
      EEO-Lys(Flu)-NH2, wherein Flu = 5(6)-carboxyfluorescein,
```

```
<220> FEATURE:
<223> OTHER INFORMATION: O = 8-amino-3,6-dioxaoctanoic acid, E = the
      modification resulting from use of compound 4 as
      described in Gildea et al., Tett. Lett.
      39:7255-7258 (1998),
<220> FEATURE:
<223> OTHER INFORMATION: Lys = the amino acid L-lysine, and NH2 =
      amidation.

<400> SEQUENCE: 58
atcacgaaga aggttctg                                                      18

<210> SEQ ID NO 59
<211> LENGTH: 18
<212> TYPE: DNA
<213> ORGANISM: Artificial Sequence
<220> FEATURE:
<223> OTHER INFORMATION: Peptide nucleic acid probe is labeled and
      modified N-terminally with Flu-OEE and C-terminally with
      EEO-Lys(Flu)-NH2, wherein Flu = 5(6)-carboxyfluorescein,
<220> FEATURE:
<223> OTHER INFORMATION: O = 8-amino-3,6-dioxaoctanoic acid, E = the
      modification resulting from use of compound 4 as
      described in Gildea et al., Tett. Lett.
      39:7255-7258 (1998),
<220> FEATURE:
<223> OTHER INFORMATION: Lys = the amino acid L-lysine, and NH2 =
      amidation.

<400> SEQUENCE: 59
tttggaccac tctgtggc                                                      18

<210> SEQ ID NO 60
<211> LENGTH: 18
<212> TYPE: DNA
<213> ORGANISM: Artificial Sequence
<220> FEATURE:
<223> OTHER INFORMATION: Peptide nucleic acid probe is labeled and
      modified N-terminally with Flu-OEE and C-terminally with
      EEO-Lys(Flu)-NH2, wherein Flu = 5(6)-carboxyfluorescein,
<220> FEATURE:
<223> OTHER INFORMATION: O = 8-amino-3,6-dioxaoctanoic acid, E = the
      modification resulting from use of compound 4 as
      described in Gildea et al., Tett. Lett.
      39:7255-7258 (1998),
<220> FEATURE:
<223> OTHER INFORMATION: Lys = the amino acid L-lysine, and NH2 =
      amidation.

<400> SEQUENCE: 60
gaatcttcac aggaaagc                                                      18

<210> SEQ ID NO 61
<211> LENGTH: 18
<212> TYPE: DNA
<213> ORGANISM: Artificial Sequence
<220> FEATURE:
<223> OTHER INFORMATION: Peptide nucleic acid probe is labeled and
      modified N-terminally with Flu-OEE and C-terminally with
      EEO-Lys(Flu)-NH2, wherein Flu = 5(6)-carboxyfluorescein,
<220> FEATURE:
<223> OTHER INFORMATION: O = 8-amino-3,6-dioxaoctanoic acid, E = the
      modification resulting from use of compound 4 as
      described in Gildea et al., Tett. Lett.
      39:7255-7258 (1998),
<220> FEATURE:
<223> OTHER INFORMATION: Lys = the amino acid L-lysine, and NH2 =
      amidation.

<400> SEQUENCE: 61
gattctacac aaagagag                                                      18
```

<210> SEQ ID NO 62
<211> LENGTH: 17
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 62
ttgcagtgag ccgagat                                               17

<210> SEQ ID NO 63
<211> LENGTH: 17
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 63
ggccgggcgc ggtggct                                               17

<210> SEQ ID NO 64
<211> LENGTH: 18
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 64
gctgggatta caggcgtg                                              18

<210> SEQ ID NO 65
<211> LENGTH: 16
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 65
gggaggccga ggcggg                                                16

<210> SEQ ID NO 66
<211> LENGTH: 21
<212> TYPE: DNA
<213> ORGANISM: Artificial Sequence
<220> FEATURE:
<223> OTHER INFORMATION: Peptide nucleic acid probe is modified

```
            N-terminally with EE and C-terminally with EE-NH2,
            wherein E = the modification resulting from use of
            compound 4
<220> FEATURE:
<223> OTHER INFORMATION: as described in Gildea et al., Tett. Lett.
      39:7255-7258 (1998), and NH2 = amidation.

<400> SEQUENCE: 66
gccaggctgg tctcgaactc c                                            21

<210> SEQ ID NO 67
<211> LENGTH: 21
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 67
gaaaccccgt ctctactaaa a                                            21

<210> SEQ ID NO 68
<211> LENGTH: 16
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 68
gccgggcgtg gtggcg                                                  16

<210> SEQ ID NO 69
<211> LENGTH: 18
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 69
tagctgggat tacaggcg                                                18

<210> SEQ ID NO 70
<211> LENGTH: 17
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.
```

```
<400> SEQUENCE: 70
gggaggctga ggcagga                                                   17

<210> SEQ ID NO 71
<211> LENGTH: 21
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 71
cctcccgggt tcaagcgatt c                                              21

<210> SEQ ID NO 72
<211> LENGTH: 21
<212> TYPE: DNA
<213> ORGANISM: Artificial Sequence
<220> FEATURE:
<223> OTHER INFORMATION: Peptide nucleic acid probe is modified
      N-terminally with EE and C-terminally with EE-NH2,
      wherein E = the modification resulting from use of
      compound 4
<220> FEATURE:
<223> OTHER INFORMATION: as described in Gildea et al., Tett. Lett.
      39:7255-7258 (1998), and NH2 = amidation.

<400> SEQUENCE: 72
tgcactccag cctgggcgac a                                              21
```